United States Patent [19]

Harada et al.

[11] Patent Number: 5,021,439
[45] Date of Patent: Jun. 4, 1991

[54] CEREBRAL FUNCTION AMELIORATING AGENTS RELATED TO TAN-950 A

[75] Inventors: Setsuo Harada; Akinobu Nagaoka, both of Kawanishi; Katsumi Itoh; Shinji Terao, both of Toyonaka, all of Japan

[73] Assignee: Takeda Chemical Industries, Ltd., Osaka, Japan

[21] Appl. No.: 408,389

[22] Filed: Sep. 18, 1989

[30] Foreign Application Priority Data

Oct. 31, 1988 [JP] Japan ............................ 63-276919
Apr. 14, 1989 [JP] Japan ............................ 1-095595
Aug. 29, 1989 [JP] Japan ............................ 1-222241
Sep. 11, 1989 [JP] Japan ............................ 1-235123

[51] Int. Cl.$^5$ ............... A61K 31/42; A61K 31/445; A61K 31/495; C07D 261/12
[52] U.S. Cl. .................... 514/380; 514/210; 514/212; 514/236.8; 514/252; 514/315; 514/326; 514/340; 540/200; 540/529; 544/137; 544/367; 546/209; 546/243; 546/275; 548/243
[58] Field of Search ............. 548/243; 514/380, 340, 514/236.8, 252, 326; 546/275, 209; 544/137, 367

[56] References Cited

U.S. PATENT DOCUMENTS 4,298,744 11/1981 Kelly et al. .................. 548/243
4,455,430 6/1984 Kelly et al. .................. 548/243

FOREIGN PATENT DOCUMENTS 0289354 11/1988 European Pat. Off. .

Primary Examiner—Cecelia Shen
Attorney, Agent, or Firm—Wegner, Cantor, Mueller & Player

[57] ABSTRACT

A compound having the formula (I) or (II)

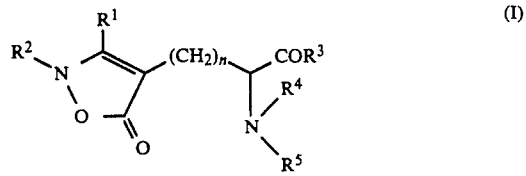

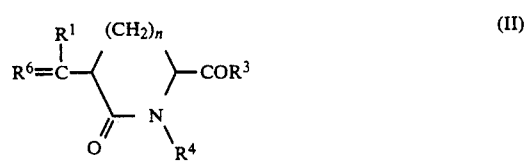

wherein $R^1$ is a hydrogen atom or an organic residue bonded via a carbon atom, $R^2$ is a hydrogen atom or a N-protecting group, $-COR^3$ is an optionally esterified or amidated carboxyl group, $R^4$ and $R^5$ are the same or different and respectively a hydrogen atom or an acyl group or a chain or alicyclic hydrocarbon group optionally having an aryl substituent, $R^6$ is NOH or O, n is an integer of 0 to 3, or $R^4$ and $R^5$ together with the adjacent nitrogen atom may form a ring or an optionally substituted benzylidene amino group, which is useful therapeutics of brain dysfunction.

15 Claims, 8 Drawing Sheets

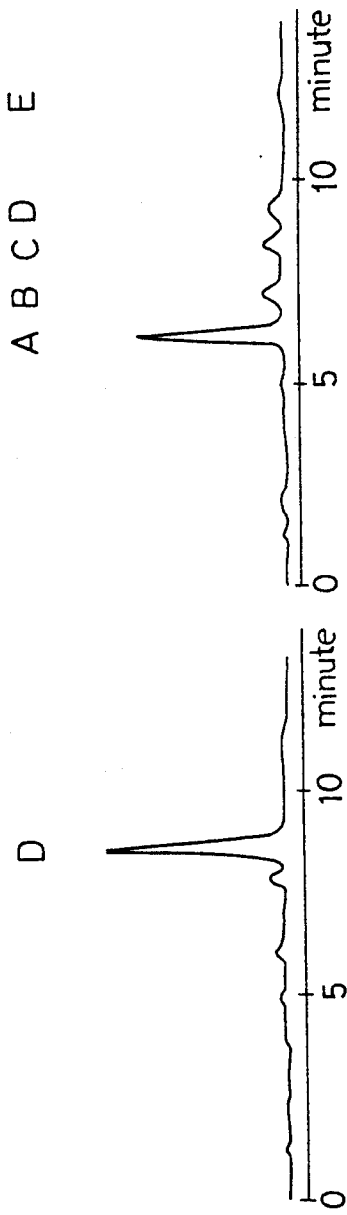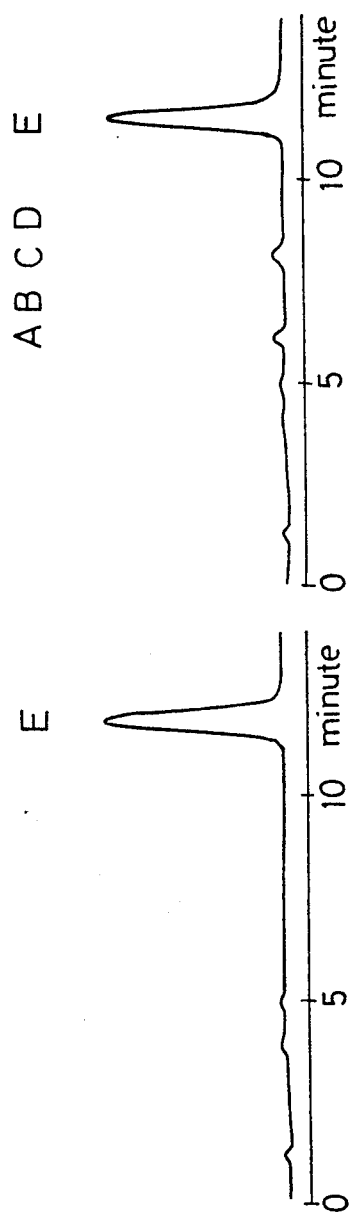

CEREBRAL FUNCTION AMELIORATING AGENTS RELATED TO TAN-950 A

BACKGROUND OF THE INVENTION
1. Field of the Invention

The present invention relates to new heterocyclic compounds, production and use thereof. The compounds are especially useful as therapeutics of brain dysfunction.

2. Description of the Prior Art

A profile of diseases is changing greatly due to a rapid increasing population of an old-age people. A senile dementia among various gerontodiseases is one of the most important study subjects from both of the social and medical viewpoints One of the medical measures for this senile dementia is to develop therapeutic drugs. Cerebral vasodilators and metabolism enhancers or agents for improving the function of cerebral neuronal transmitters have been used as therapeutic agents for senile dementia.

However, therapeutic agents for senile dementia which have been used so far could not give a satisfactory clinical efficacy. One of the biggest reasons for it was that these therapeutic agents either have an insufficient effect or have no efficacy at all against memory disorder which is the main symptom of a senile dementia. It makes it more difficult to create truly effective agents in this field that the cause of senile dementia (particularly Alzheimer's type of dementia) and the critical mechanism for memory disorder have not yet been sufficiently clarified.

However, the physiological study of brain made it clear that there is a close relation between functional disorder of cerebral cholinergic neuron and memory disorder, and a possibility was suggested that an activator for cerebral cholinergic function may become the therapeutic agent for dementia but nobody has succeeded so far in developing the drugs while the clinical trials are ongoing.

Other physiological findings to overcome the aforesaid subject is that an intracerebral amino acid, particularly glutamate, has a very important role to form a memory. Intracerebral receptors of glutamate are mainly classified into three sub-types and those are NMDA (N-methyl-D-aspartate)-type, quisqualate-type and kainate-type. It is presumed that the action of glutamate on the NMDA-type receptor among these receptors is important to form a memory. This presumption is based upon the very important new medical finding that the stimulation by glutamate of the NMDA-type receptor participates in the mechanism to form a physiological phenomenon of long term potentiation at the hippocampus in the brain [Teyler, T. J. and Discenna, P., Ann. Rev. Neurosci., 10:131-161, 1987; Cotman, C. W. and Monagham, D. T. Ann Rev. Neurosci., 11:61-80, 1988]. However, it is considered that a participation of the other sub- type receptors can not be denied completely.

SUMMARY OF THE INVENTION

The inventors of this invention have established a test system to prove an affinity to the intracerebral glutamate-receptors including those three sub-type receptors, activation of the hippocampus neuro cell and the effectiveness on the model of defects of memory. Also, we have isolated TAN-950 having antifungal activity from a fermentation broth of Actinomycetes, determined its chemical structure and synthesized various derivatives of isoxazole which is the basic nucleus of the said compound.

By testing these compounds in our own test system, it was found that they possessed potent improving effects on cerebral dysfunctions, especially memory impairment.

Thus, according to the present invention, it provides a compound of the following general formula (I) or (II):

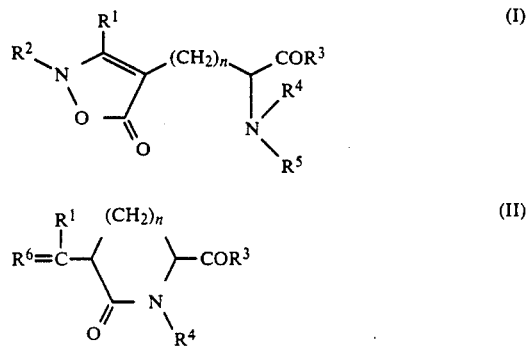

, wherein $R^1$ is a hydrogen atom or an organic residue bonded via a carbon atom, $R^2$ is a hydrogen atom or a N-protecting group, $-COR^3$ is an optionally esterified or amidated carboxyl group, $R^4$ and $R^5$ are the same or different and, respectively a hydrogen atom or an acyl group or a chain or alicyclic hydrocarbon group optionally having an aryl substituent, $R^6$ is NOH or O, n is an integer of 0 to 3, or $R^4$ and $R^5$ together with the adjacent nitrogen atom may form a ring or an optionally substituted benzylidene amino group, and salt thereof, and also a cerebral function ameliorator containing the same.

In the formulae (I) and (II), a compound where $R^1$, $R^2$, $R^4$ and $R^5$ are all hydrogen atoms, $-COR^3$ is carboxyl, and where n is 1, and the configuration of the asymmetric carbon atom to which the α-amino group is bonded is an S-configuration is known as the abovementioned TAN-950A. However, all other compounds represented by the formulae (I) and (II) are novel compounds. These novel compounds are representable by the following formula (I') and (II'):

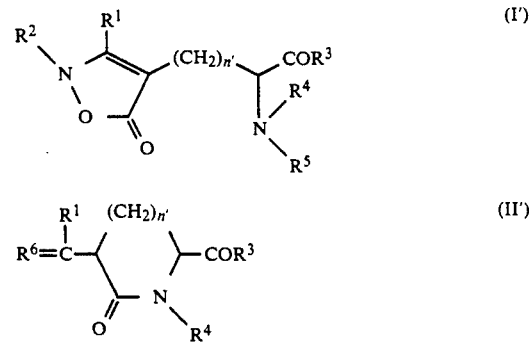

, wherein $R^1$ is a hydrogen atom or an organic residue bonded via a carbon atom, $R^2$ is a hydrogen atom or a N-protecting group, $-COR^3$ is an optionally esterified or amidated carboxyl group, $R^4$ and $R^5$ are the same or different and, respectively a hydrogen atom or an acyl group or a chain or alicyclic hydrocarbon group optionally having an aryl substituent, R⁶ is NOH or O, n' is an integer of 0 to 3, or $R^4$ and $R^5$ together with the adjacent nitrogen atom may form a ring or an optionally substituted benzylidene amino group, provided that when $R^1$, $R^2$, $R^4$ and $R^5$ are hydrogen atoms, —$COR^3$ is carboxyl group and the configuration of the asymmetric carbon atom to which α-amino group is bonded is S, n' is 0, 2 or 3.

PREFERRED EMBODIMENT OF THE INVENTION

Figure 1:
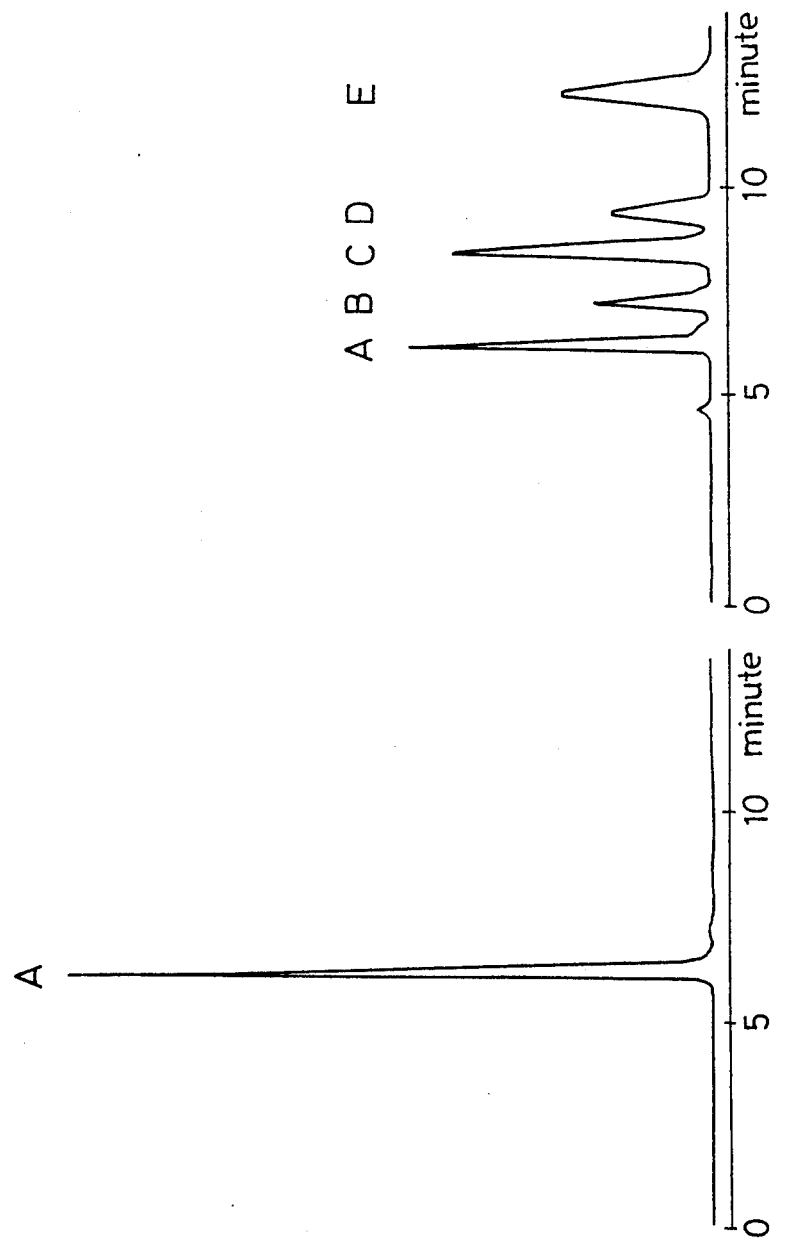
FIG. 1 shows the HPLC pattern of each of the ingredients of TAN-950.

Examples of the organic residues bonded via a carbon atom represented by $R^1$ in the aforesaid formula are alkyl, alkenyl, alkynyl, aryl, heteroaryl, aralkyl and cycloalkyl group.

The alkyl groups may be preferably those containing 1 to 6 carbon atoms, such as methyl, ethyl, n-propyl, isopropyl, n-butyl, isobutyl, sec-butyl, tert-butyl, 1,1-dimethylpropyl, n-pentyl, isopentyl, n-hexyl and isohexyl, more preferably those containing 1 to 4 carbon atoms.

The alkenyl groups may be preferably those containing 2 to 6 carbon atoms, such as allyl, 1,3-butadienyl, 2,4-pentadienyl and 1,3,5-hexatrienyl.

The alkynyl groups may be preferably those containing 2 to 6 carbon atoms, such as ethynyl, 1-propynyl and 1-pentynyl.

Examples of the aryl groups are phenyl, 1-naphthyl, 2-naphthyl, biphenyl, anthryl and indenyl, among which phenyl, 1-naphthyl and 2-naphtyl are especially preferable.

The heteroaryl groups may be preferably those having a five or six membered ring containing one of nitrogen, oxygen or sulfur atom, such as 2-pyridyl, 3-pyridyl, 4-pyridyl, 2-pyrrolyl, 3-pyrrlyl, 2-furyl, 3-furyl, pyranyl, 2-thienyl and 3-thienyl, among which 2-furyl, 2-pyridyl, 3-pyridyl and 4-pyridyl are especially preferable.

The aralkyl groups may be preferably phenyl-$C_{1-4}$ alkyl groups, such as benzyl, phenethyl and phenylpropyl, among which benzyl is most preferable.

The cycloalkyl groups may be preferably those containing 3 to 7 carbon atoms, such as cyclopropyl, cyclobutyl, cyclopentyl, cyclohexyl and cycloheptyl.

Especially, $R^1$ is preferred to be hydrogen atom, $C_{1-3}$ alkyl groups and $C_{3-5}$ cycloalkyl groups.

Examples of the N-protecting groups represented by $R^2$ in the above formula are a $C_{1-4}$ alkyl group such as methyl, ethyl, n-propyl, isopropyl, n-butyl, sec-butyl or tert-butyl; an aromatic acyl group such as p-nitrobenzoyl, p-tert-butylbenzoyl, p-tert-butylbenzenesulfonyl, benzenesulfonyl or toluenesulfonyl; an aliphatic acyl group such as formyl, acetyl, propionyl, monocholoroacetyl, dichloroacetyl, trichloroacetyl, methanesulfonyl, ethanesulfonyl or trifluoroacetyl; an esterified carboxy group to be mentioned later with respect to —$COR^3$ group; a methylene group such as (hexahydro-1H-azepin-1-yl)methylene; a sulfonyl group such as α-amino-2-carboxyethylsulfonyl; an aralkyl group such as trityl, benzyl, phenethyl, phenylpropyl, p-nitrobenzyl, α-methylbenzyl, α-methylphenylpropyl or p-methoxybenzyl; other N-protecting groups than acyl group, such as 2-nitro-phenylthio or di- or trialkylsilyl. The preferable examples are methyl, acetyl, benzoyl, t-butoxycarbonyl, p-nitrobenzyl, benzyloxycarbonyl and p-methoxybenzyloxycarbonyl.

Besides, the most preferable $R^2$ is hydrogen atom.

Examples of the esterified carboxy group in the optionally esterified or amidated carboxyl group represented by —$COR^3$ in the above formula are methoxycarbonyl, ethoxycarbonyl, tert-butoxycarbonyl, isopropoxycarbonyl, 2-cyanoethoxycarbonyl, 2,2,2,-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl or phenyloxycarbonyl, among which methoxycarbonyl, ethoxycarbonyl, tert-butoxycarbonyl and p-nitrobenzyloxycarbonyl are preferable.

Examples of $R^3$ in the amidated carboxyl group within the optionally esterified or amidated carboxyl group represented by —$COR^3$ are amino, a $C_{1-10}$ alkyl (e.g. in addition to the examples referred to in $R^1$, heptyl, octyl, nonanyl, decanyl) amino, a $C_{3-7}$ cycloalkyl (e.g., the same with those exemplified in $R^1$), an aralkyl [e.g. benzyl, phenethyl, α-methylbenzyl, 3-phenylpropyl, 1-(1-naphthyl)ethyl]amino, a cyclic amino (e.g. morpholino, piperidino, 4-phenyl-1piperazinyl), an amino acid residue (e.g. alanino, β-alanino, glycino, Nα-histidino, isoleucino, leucino, lysino, methionino, norleucino, norvalino, ornitino, prolino, sarcosino, serino, tyrosino, valino, tryptophano, asparto, asparagino, glutamino, glutamo, β-aminoalanino, α-amino-β-alanino, thialysino, 4-oxalysino, 3-carboxypropylamino, 4-carboxybutylamino, 4-carboxybenzylamino, 4-carboxypiperidino, 3-carboxypiperidino, 2-carboxypiperidino or 1-carboxycyclopentyl-2-amino). In case where $R^3$ is an amino acid residue which has a carboxy group therein, this carboxy group may be esterified and in case where the amino acid residue has an amino group, this amino group may be acylated. Examples of the carboxyl groups optionally esterified are carboxyl, an alkoxycarbonyl such as $C_{1-4}$ alkoxycarbonyl (e.g. methoxycarbonyl, ethoxycarbonyl, tert-butoxycarbonyl) or a phenyl-$C_{1-4}$ alkoxycarbonyl (e.g. benzyloxycarbonyl, phenethyloxycarbonyl). Examples of the aforesaid amino group optionally acylated are amino, a $C_{2-15}$ alkanoylamino (e.g. acetylamino, propionylamino, lauroylamino), benzoylamino, a phenyl-$C_{1-4}$ alkoxycarbonylamino (e.g. benzyloxycarbonylamino), a $C_{1-4}$ alkoxycarbonylamino (e.g. tert-butoxycarbonylamino), 4-methoxyfumaroylamino and 4-aminofumaroylamino.

Examples of the acyl groups represented by $R^4$ or $R^5$ in the above formula are an aromatic acyl group, an aliphatic acyl group and an amino acid residue.

Examples of the aromatic acyl groups are benzoyl, 4-nitrobenzoyl, 4-tert-butylbenzoyl, 4-tert-butylbenzene-sulfonyl, benzenesulfonyl and toluenesulfonyl.

Examples of the aliphatic acyl groups are formyl, acetyl, propionyl, butyryl, monochloroacetyl, dichloroacetyl, trichloroacetyl, methanesulfonyl, ethanesulfonyl, trifluoroacetyl, a phenyl-$C_{1-4}$-alkoxycarbonyl (e.g. benzyloxycarbonyl) and a $C_{1-4}$ alkoxycarbonyl (e.g. tert-butoxycarbonyl).

Examples of the amino acid residues are phenylalanyl, alanyl, $\beta$-alanyl, glycyl, histidyl, isoleucyl, leucyl, lysyl, methionyl, norleucyl, norvalyl, ornityl, prolyl, sarcosyl, seryl, tyrosyl, valyl, triptophyl, $\alpha$-aspartyl, $\beta$-aspartyl, asparginyl, $\alpha$-glutamyl, $\gamma$-glutamyl, glutaminyl, $\beta$-aminoalanyl, 4- thialysyl, 3-(2-aminoethyl)sulfinylalanyl and 4-oxalysyl. In case where these amino acid residues contain a carboxyl group, said carboxyl group may be esterified, and in case where those amino acid residues contain an amino group, said amino group may be the acylated one. Examples of the carboxyl group optionally esterified and the amino group optionally acylated are those exemplified in the aforesaid $R^3$.

Examples of the hydrocarbon groups in the chain or alicyclic hydrocarbon residues optionally having aryl substituents represented by $R^4$ or $R^5$ are alkyl, alkenyl, alkynyl, aralkyl and cycloalkyl groups and the examples of these groups are those exemplified for the organic residues bonded via a carbon atom in $R^1$.

Examples of said aryl group are phenyl, 1-naphtyl, 2-naphtyl, biphenyl, anthryl or indenyl, among which phenyl, 1-naphtyl and 2-naphtyl are preferable The most preferable examples of the chain or alicyclic hydrocarbon groups optionally having aryl substituent are benzyl and phenethyl.

Also, examples of these cases where $R^4$ and $R^5$ may form a ring together with an adjacent nitrogen atom are phthalimido, succinimido and malanimido. Also, $R^4$ and $R^5$ together with an adjacent nitrogen atom may form benzylidenamino and p-nitrobenzylidenamino.

Both of $R^4$ and $R^5$ are most preferable hydrogen atoms. The integer represented by n is preferably 0 or 1.

The following is explained on the manufacturing methods of the compounds of the present invention.

Out of the compounds of the present invention, TAN-950 A to E can be obtained by culturing a TAN-950 producing strain belonging to Streptomyces in a medium and recovering the said compounds from the cultured broth.

As the TAN-950 producing strains, any organism can be used as far as it can produce TAN-950. The strains isolated and named by the inventors of the present invention as Streptomyces platensis A-136 and its family of strains (hereinafter this strain is sometime called as A-136 strain) is an example to be used most efficiently.

The following are the morphological characteristics and observation in the cultural medium for classification of the said strain.

This strain forms aerial mycelium in the conventional culture medium used for classification, which shows monopodial branch. The spore-forming hyphae shows spiral shape, and the spore forms a chain of more than 10, the surface thereof is smooth and the size thereof is 0.8 -1.2 $\mu m \times 0.9$ -1.3 $\mu m$. The formation of sporangium, flagellum spore and sclerotium was not observed in the conventional culture medium for classification.

Table 1 shows the growing status of this strain in the cultural medium for classification.

Unless specifically otherwise described, the following is morphological observation of the culture made for 21 days at 28° C.

In the table, ( ) indicates the name of color according to Color Harmony Manual, 4th Edition (Container Corporation of America, 1958).

TABLE 1

The Cultural Observation in Medium for Classification of A-136 Strain

| Media | Degree of growth | Color of surface of colony | Color of back of Elolony | Disseminating color into medium |
|---|---|---|---|---|
| Sucrose-nitrate agar medium | Moderate disseminating growth | week pearl (3ba) pale gray (3dc) | pearl (3ba) | none |
| Glucose-asparagine agar medium | Moderate limitative growth | week pearl (3ba) | pale yellow (2ca) - yellow (2ea) | none |
| Glycerine asparagine agar medium | Excellent disseminating growth | rich white - pale gray (3dc) | pale yellow (2ca) - beige (3ec) | none |
| Starch inorganic salt agar medium | Excellent | rich white - pale gray (3dc) - bright brownish gray (3fe), black and wet | yellow (2ea) - yellow brown (2gc) - black | none |
| Tyrosine agar medium | Moderate limitative growth | week pearl (3ba) | pearl (3ba) | none |
| Nutrition agar medium | Moderate limitative growth | week pearl (3ba) | pale (3ba) - beige (3ec) | none |
| Yeat malt agar mesium | Excellent disseminating growth | rich white - bright brown (3fe) - gray (5fe), black and wet | pale yellow (2ca) - mud yellow (2ng) | none |
| Oatmeal agar mediu, | Excellent | rich pearl (3ba) - bright brown (3fe), black and wet gary (3fe) - black and wet | pearl (3ba) - pale yellow (2ca) | none |

The physiological characteristics of A-136 strain are as follows.

(1) Temperature range for growth:
  10-36° C. and preferably
  28-32° C.
(2) Liquefaction of gelatin: positive
(3) Hydrolysis of starch: positive
(4) Coagulation and peptonization of skin milk: negative
(5) Formation of melanoid-pigment: negative (peptone-yeast-iron agar medium and tyrosine agar medium)
(6) Reduction of nitric acid salt: negative (International Streptomyces Project No. 8 medium)
(7) Assimilation of carbon source (Pridham Gottlieb agar medium):
  Carbon source to be well assimilated inositol, D-mannitol, D-xylose, D-glucose, D-fructose, raffinose
  Carbon source to be moderately assimilated L-arabinose
  Carbon source not to be assimilated rhamnose, sucrose From the fact that LL-diaminopimeric acid was detected in the HCl-hydrolyzate of A-136 strain mycelia, it was considered that this strain belongs to Genus Streptomyces.

As the results of comparison of this strain with the existing known strains based on the morphological, cultural and physiological characteristics, this strain was identified as Streptomyces platensis and named as *Streptomyces platensis* A-136. The *Streptomyces platensis* A-136 to be used in the present invention was deposited on Apr. 22, 1987 at the Institute of Fermentation, Osaka (IFO), IFO No. 14603 and on Apr. 30, 1987 at the Fermentation Research Institute, Agency of Industrial Science and Technology (FRI), FERM No. P-9358. The latter deposit was changed to the deposit under the Budapest Treaty and kept at the said institute FERM No. BP-1786.

The bacteriological properties are, as the general properties of the strains belonging to Streptomyces, very variable, and *Streptomyces platensis* A-136 is not an exception therefrom. Therefore, the properties of this strain are, as mentioned above, not necessarily stable and various mutants are easily obtained. However, these mutants can be also used in the present invention as far as they do not lose the capability to produce TAN-950. It is not material whether these mutants were obtained by a natural cause or an artificial cause (e.g. ultraviolet rays, X-rays, radiation, nitroguanidine).

In addition to the aforesaid A-136 strain, other known strains belonging to Streptomyces can be also used in the present invention, such as *Streptomyces hygroscopicus* A-300 (cf., FERM No. 1312, Japanese Patent Publication No. 54–43600); *Streptomyces hygroscopicus* subsp. angustmyceticus, IFO No. 3934 and IFO No. 3935; *Streptomyces hygroscopicus* subsp. hygroscopicus, IFO No. 14012.

According to the present invention, culturing is carried out in a medium containing assimilable sources of carbon and digestible sources of nitrogen and of inorganic salt. It is possible to add to the medium a trace effective substance such as micronutrients, growth promoters or precursors. Examples of the assimilable sources of carbon are glucose, sucrose, molasses, starch, dextrin and glycerine, and examples of the digestible sources of nitrogen are meat extract, bean meal, corn steep liquor, peptone, casein and cotton seed meal, as well as inorganic compounds such as nitrates and ammonium compounds. Surface culture is possible but submerged aerobic culture is preferable. In case of submerged aerobic culture, it is desirable to culture in a neutral medium at about 20°36° C., preferably about 24–36° C.

However, the culture conditions such as the components of the medium, the liquid properties of the medium, the culturing temperature and agitating number may be adjusted and chosen depending upon the kind of the strain used and the outer conditions so that the most desirable effect can be obtained.

In order to obtain the desired TAN-950 from the culture broth, the conventional methods normally used in order to isolate the metabolites produced by the microorganisms from the cultured broths can be used. A water-soluble amphoteric TAN-950 contained mainly in the cultured broth is isolated by at first filtrating the cultured broth after addition of a filtration auxiliary agent thereto or eliminating the mycelia by centrifugation, having the active component in the filtrate absorbed by containing the filtrate with a carrier, and then dissolving the active component in an appropriate solvent form the carrier. Examples of the carriers are those which utilize different absorbability of compounds such as activated carbon, silica gel, cellulose powder, adsorptive resin, those which utilize different functional groups of compound such as ion exchange resin, ion exchange cellulose, ion exchange Sephadex and those which utilize different molecular weights of compounds such as molecular sieve carriers. Examples of the solvents to be used in order to liquate out the desired compound from these carriers are an aqueous solution of a water-soluble organic solvent, such as hydrous acetone or hydrous alcohols, an acid, an alkali, a buffer or an aqueous solution containing an inorganic or organic salt, while the combination thereof differs depending upon the types and properties of the carriers.

In more details, in case of utilizing as the carriers cation exchange resins such as Amberlite IR-120 (made by Rohm & Haas, Co., U.S.A.), Dowex 50W (made by Dow Chemical Co., U.S.A.), Diaion SK 1A (made by Mitsubishi Chemical Industries, Japan) or anion exchange resins such as Amberlite IRA-402, IRA-68, (made by Rohm & Haas, Co., U.S.A.), Dowex 1 (made by Dow Chemical Co., U.S.A.), Diaion SA10B, PA-404, WA-30 (made by Mitsubishi Chemical Industries, Japan), the objective substance in the filtrate is absorbed and liquated out by an aqueous solution containing salt, alkali or acid or by a buffer solution. It is also possible to have the objective substance absorbed with the carriers such as ion-exchange molecular sieve resins such as QAE or CM-sephadex (made by Pharmacia, Sweden) and then to liquate it out by an aqueous solution containing salt, alkali or acid, or a buffer solution. In order to eliminate salts and colored substances in the eluate, activated carbon for chromatographic use (made by Takeda Chemical Industries, Japan), adsorptive resins such as Diaion HP-20 and SP 207 (made by Mitsubishi chemical Industries, Japan), Amberlite XAD-II (made by Rohm & Haas Co., U.S.A.), molecular sieve resin, Sephadex (made by Pharmacia, Sweden) or crystalline cellulose (made by Asahi Chemicals, Japan) are used. In order to eliminate the fat-soluble substances in the filtrates or eluate, a column chromatography containing activated carbon or adsorptive resin or extraction by non-aqueous organic solvents such as dichloroethane, ethyl acetate or methylisobutylketone as well as the combination thereof is used. The high performance liquid chromatography (HPLC) is also effectively used for final purification of the compound. In applying this method, a reversed phase type resin such as YMC gel (made by Yamamura Chemicals, Japan) or TSK gel (made by Toyo Soda, Japan) is used and solvent comprising buffer solution and ion paired reagent such as tetrabutylammoniumhydroxide is used as mobile phase. From the eluate thus purified and graduated, TAN-950A is recovered as powders or crystals after processes of concentration, lyophilization and crystallization. While TAN-950A was obtained as mono-sodium salt, the free form of this compound is also obtained by the following method: monosodium salt of TAN-950A is dissolved in water and an equivalent of hydrochloric acid is added thereto. The solution is applied to a crystalline cellulose column chromatography and the column is developed by a hydrous alcohol such as hydrous methanol or hydrous propanol and then TAN-950 (free form) is obtained. It can be also possible to apply the solution containing TAN-950 to the chromatography of Amberlite IR-120 ($H^+$ type) and then elute by an aqueous ammonium.

The pharmacologically acceptable salts (e.g. potassium salt, calcium salt, etc.) of TAN-950 can be also obtained from its free form by per se known methods.

The following is the relation between TAN-950A and TAN-950B, C, D and E. FIG. 1 shows the elution pattern of the analytical HPLC under the following conditions of the mixture of TAN-950A and TAN-950A - E obtained in Example 2 mentioned below.

Carrier: YMC-Pack AQ-312 (made by Yamamura Chemicals, Japan)

Mobile Phase 0.0025M Tetrabutylammoniumhydroxide/0.02M phosphoric acid buffer solution (pH 6.0)

Detection method: UV absorption (214 nm)

Flow speed: 2 ml/min

The mixture showed 4 peaks in addition to the one of TAN-950A and the Rt values and area percentages thereof were as follows:

| Compound | Rt (min) | Area percentage (%) |
|---|---|---|
| TAN-950A | 6.2 | 22.1 |
| TAN-950B | 7.2 | 10.9 |
| TAN-950C | 8.5 | 27.4 |
| TAN-950D | 9.4 | 13.1 |
| TAN-950E | 12.3 | 24.7 |
| Total | | 98.2 |

Figures 1, 2:
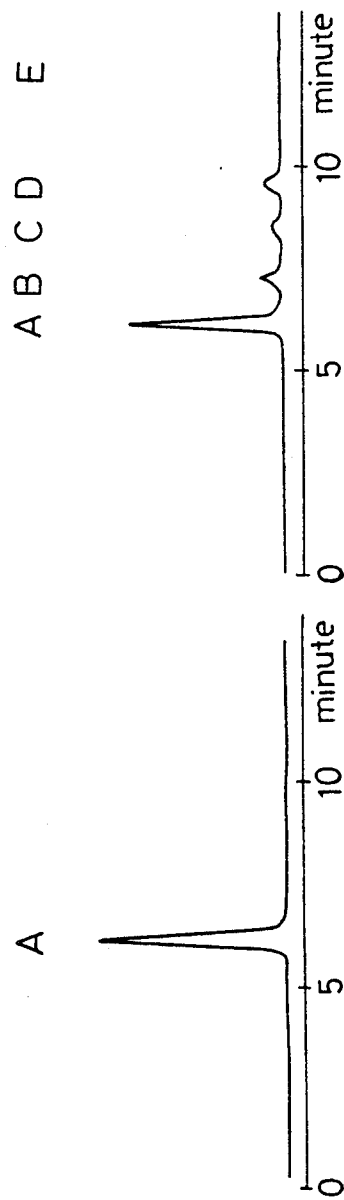
FIG. 2 shows the HPLC pattern showing a conversion of each of the ingredients of TAN-950 in its aqueous solution.
Figure 2:
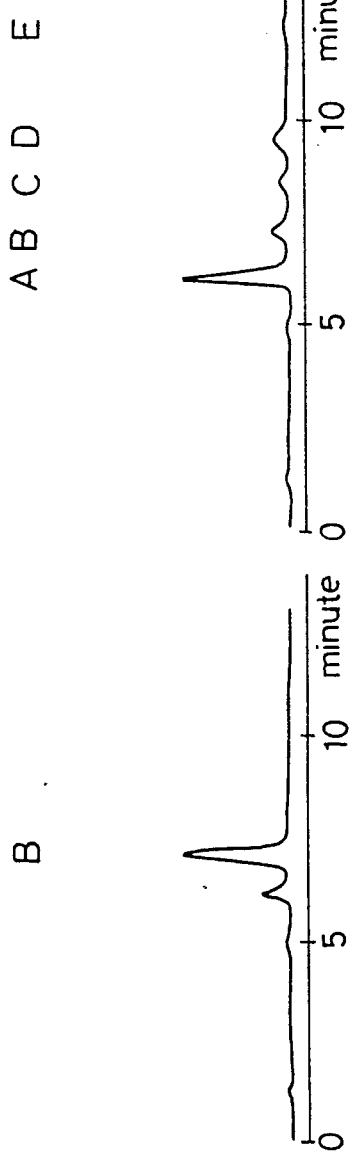

The mixture of TAN-950A - E was applied to HPLC in order to isolate each component thereof and each component was isolated as approximately single peak compound. However, the conversion of the components to the other components was observed by heating the eluate at 60° C. and then applying it to HPLC again 1 hour later (cf. FIG. 2). Table 2 shows the summary of the above data.

TABLE 2

| Conversion of each component of TAN-950 in aqueous solution (60° C.) | | | |
|---|---|---|---|
| Starting material (%)* | | Resulting substance (%)* | |
| TAN-950A | (96.3) | TAN-950A | (63.8) |
| | | TAN-950B | (13.0) |
| | | TAN-950C | (5.7) |
| | | TAN-950D | (12.1) |
| | | TAN-950E | (3.1) |
| TAN-950B | (71.0) | TAN-950A | (55.0) |

TABLE 2-continued

| Conversion of each component of TAN-950 in aqueous solution (60° C.) | | | |
|---|---|---|---|
| Starting material (%)* | | Resulting substance (%)* | |
| (TAN-950A | 17.1) | TAN-950B | (12.5) |
| | | TAN-950C | (7.7) |
| | | TAN-950D | (11.3) |
| | | TAN-950E | (4.3) |
| TAN-950C | (90.9) | TAN-950A | (12.3) |
| (TAN-950A | 1.7) | TAN-950B | (2.8) |
| | | TAN-950C | (72.1) |
| | | TAN-950D | (3.4) |
| | | TAN-950E | (5.2) |
| TAN-950D | (76.4) | TAN-950A | (53.6) |
| (TAN-950A | 4.5 | TAN-950B | (11.3) |
| TAN-950C | 5.4) | TAN-950C | (12.7) |
| | | TAN-950D | (11.2) |
| | | TAN-950E | (2.7) |
| TAN-950E | (89.4) | TAN-950A | (2.5) |
| | | TAN-950B | (1.2) |
| | | TAN-950C | (3.4) |
| | | TAN-950D | (1.2) |
| | | TAN-950E | (85.9) |

*Area percentage by HPLC

Almost the same results were obtained in water or in phosphoric acid buffer solution.

As shown clearly in Table 2, TAN-950B and D are converted to TAN-950A faster than TAN-950C and E, and TAN-950A is on the contrary converted mainly to TAN-950B and D, but slightly to TAN-950C and E. These data show that TAN-950A, B, C, D and E constitute an equilibrium mixture in an aqueous solution. TAN-950C and E which are not easily convertible are promptly converted to TAN-950A in an aqueous alkaline solution at room temperature. In case that the same mixture was reacted with tert-butoxycarbonyl compound (Boc), only the N-Boc compound of TAN-950A was obtained, but in case that the mixture of TAN-950B E was reacted with p-nitrobenzyl compound (PNB), 4 kinds of PNB-ester compounds were obtained. Only one pure ester compound was obtained by chromatography of these esters but the other three ester compounds were not isolated. The physicochemical data of said pure substance supported the following formula and taking into consideration these data totally the following relation of TAN-950A to E is determined.

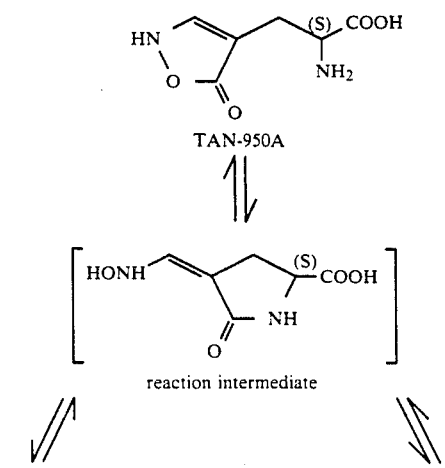

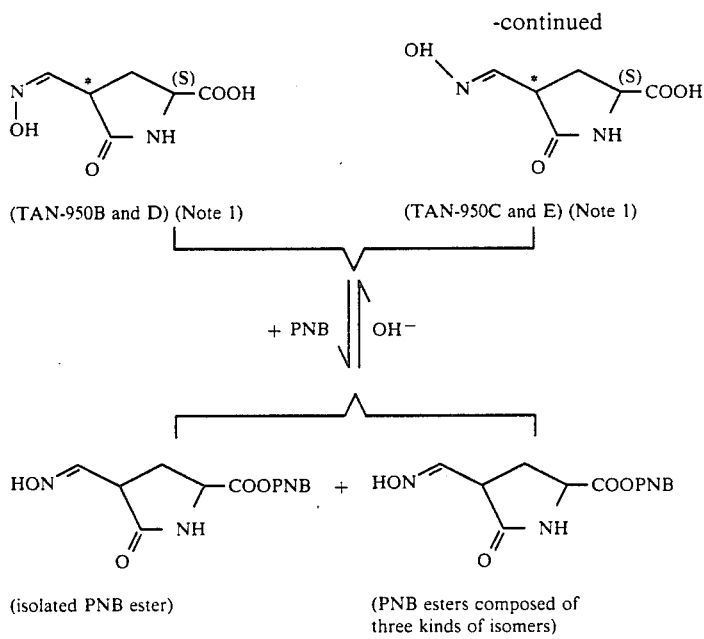

(TAN-950B and D) (Note 1)     (TAN-950C and E) (Note 1)

(isolated PNB ester)     (PNB esters composed of three kinds of isomers)

Notes: TAN-950B and D, as well as C and E have different steric configurations at asterisked position.

The following shows physiocochemical properties of TAN-950A (mono sodium salt) obtained in Example 2 mentioned below.

1) Appearance: white solid
2) Optical rotation: $[\alpha]_D^{23} -70° \pm 10°$ (C=0.524, in water)
3) Elemental analysis (%):

| Found | Theoretical value* |
|---|---|
| C, 33.64 | C, 33.97 |
| H, 4.31 | H, 4.28 |
| N, 12.72 | N, 13.21 |
|  | O, 37.82 |
| Na, 11.0 | Na, 10.66 |

*Calculation was made as containing 1 mole of water

4) Molecular weight: SI-MS method

| m/z | 195 | $(M + H)^+$, |
|---|---|---|
|  | 217 | $(M + Na)^+$, |
|  | 239 | $(M + 2 Na)^+$ |

Figures 2, 3:
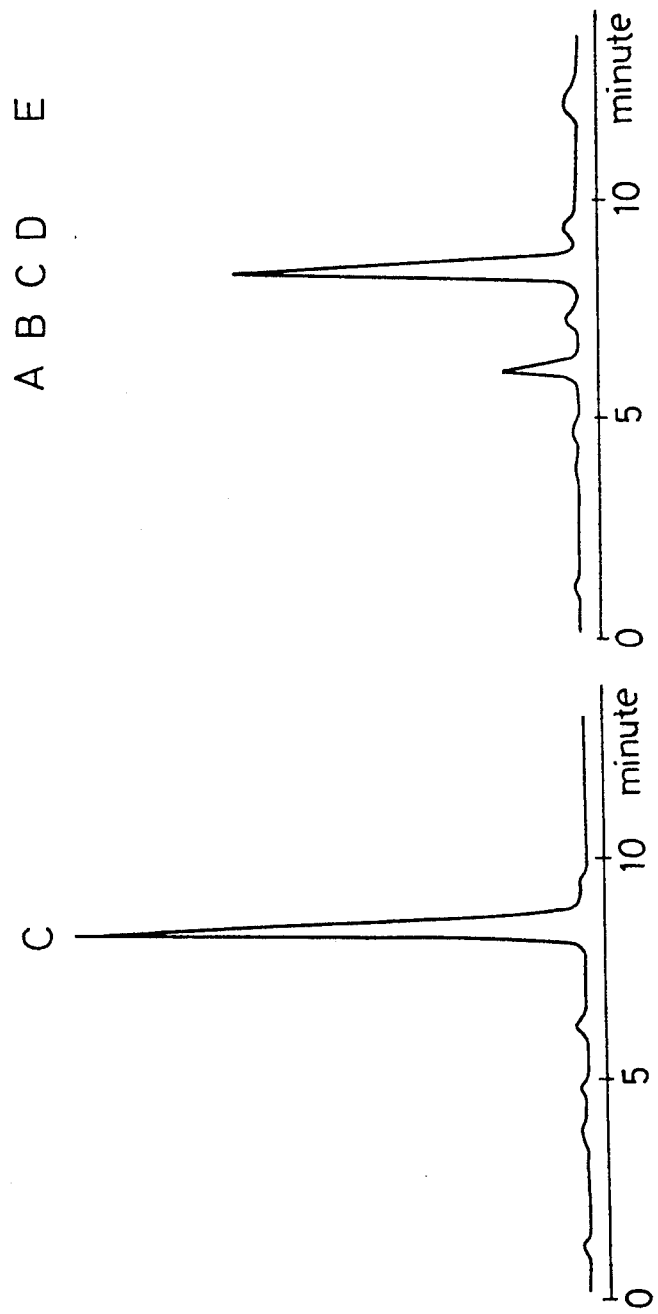
FIG. 3 shows the ultraviolet absorption spectrum in water of TAN-950A (mono-sodium salt) obtained in Example 2.
Figure 3:
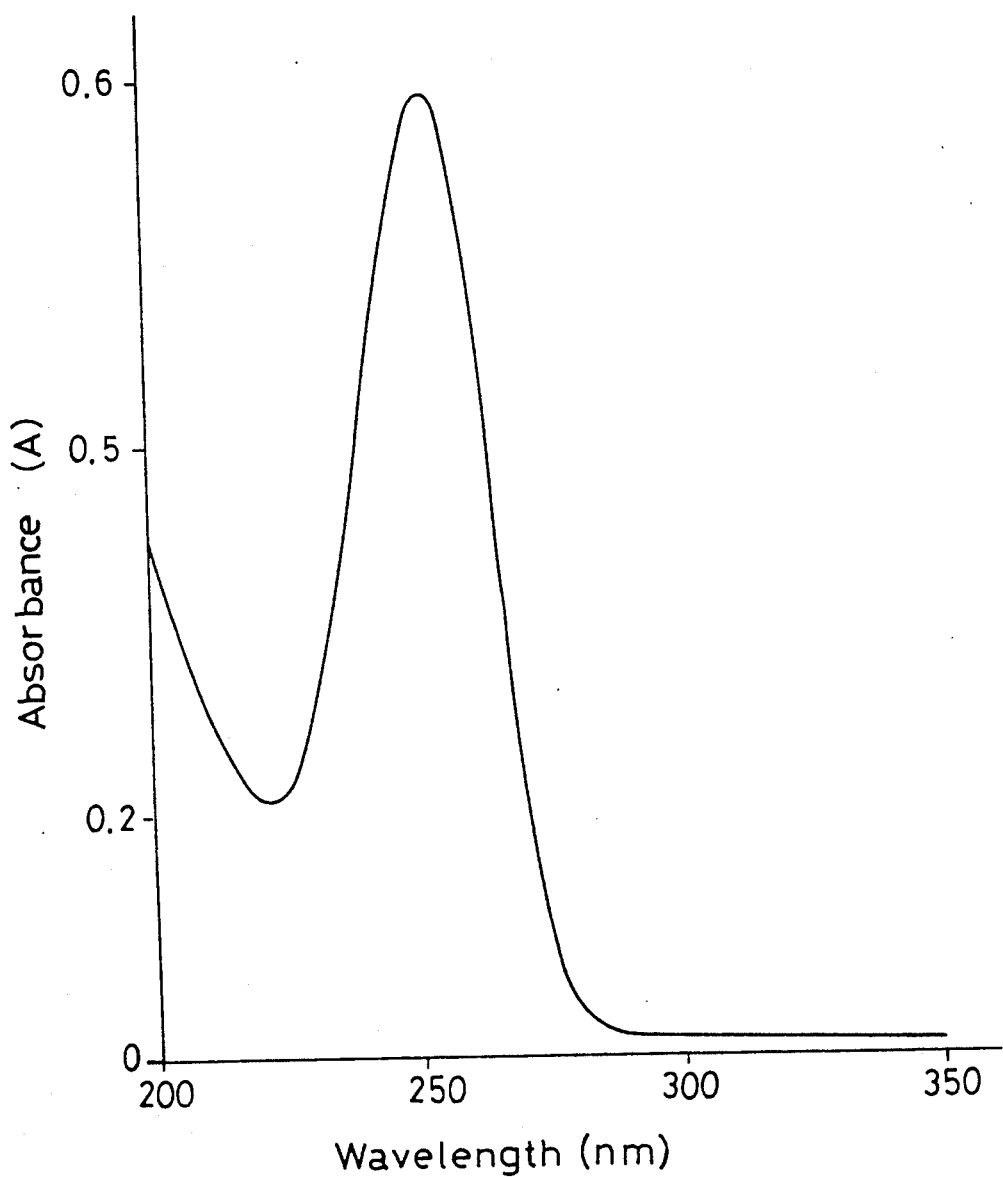

5) Molecular formula: $C_6H_7N_2O_4NA$
6) Ultraviolet absorption spectrum: In water (cf. FIG. 3)

| $\lambda_{max}$ 253 ± 3 nm ($E_{1cm}^{1\%}$ = 380 ± 50) (in water) |
| $\lambda_{max}$ 259 ± 3 nm ($E_{1cm}^{1\%}$ = 421 ± 50) (in N/10 HCl) |
| $\lambda_{max}$ 255 ± 3 nm ($E_{1cm}^{1\%}$ = 373 ± 50) (in N/10 NaOH) |

Figure 4:
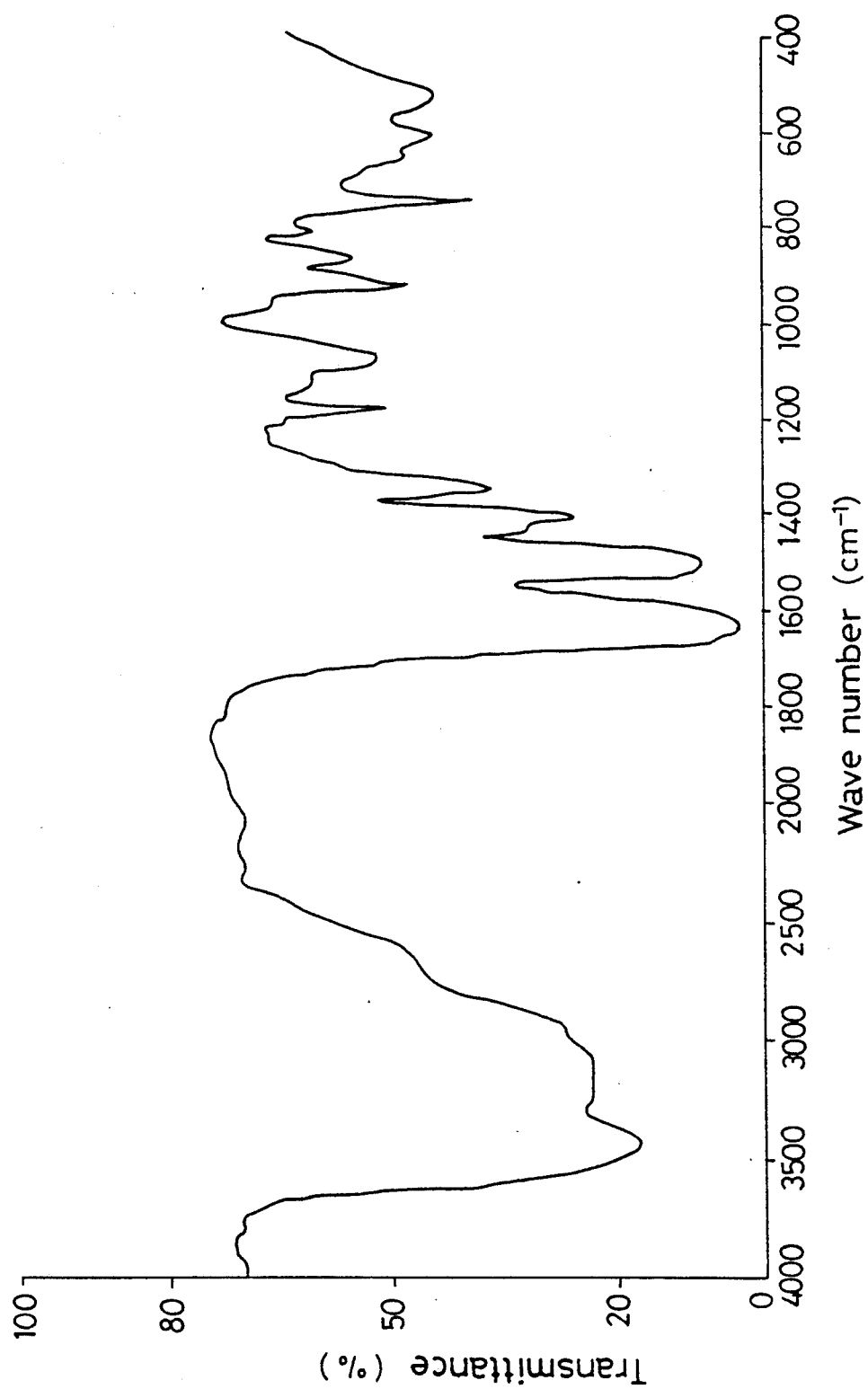
FIG. 4 shows the infrared absorption spectrum (KBr method) of TAN-950A.

7) Infrared absorption spectrum: KBr Tablet (cf. FIG. 4)

Major waves (cm$^{-1}$) 3430, 1640, 1500, 1410, 1350, 1180, 1070, 930, 870, 750, 610, 530

Figure 5:
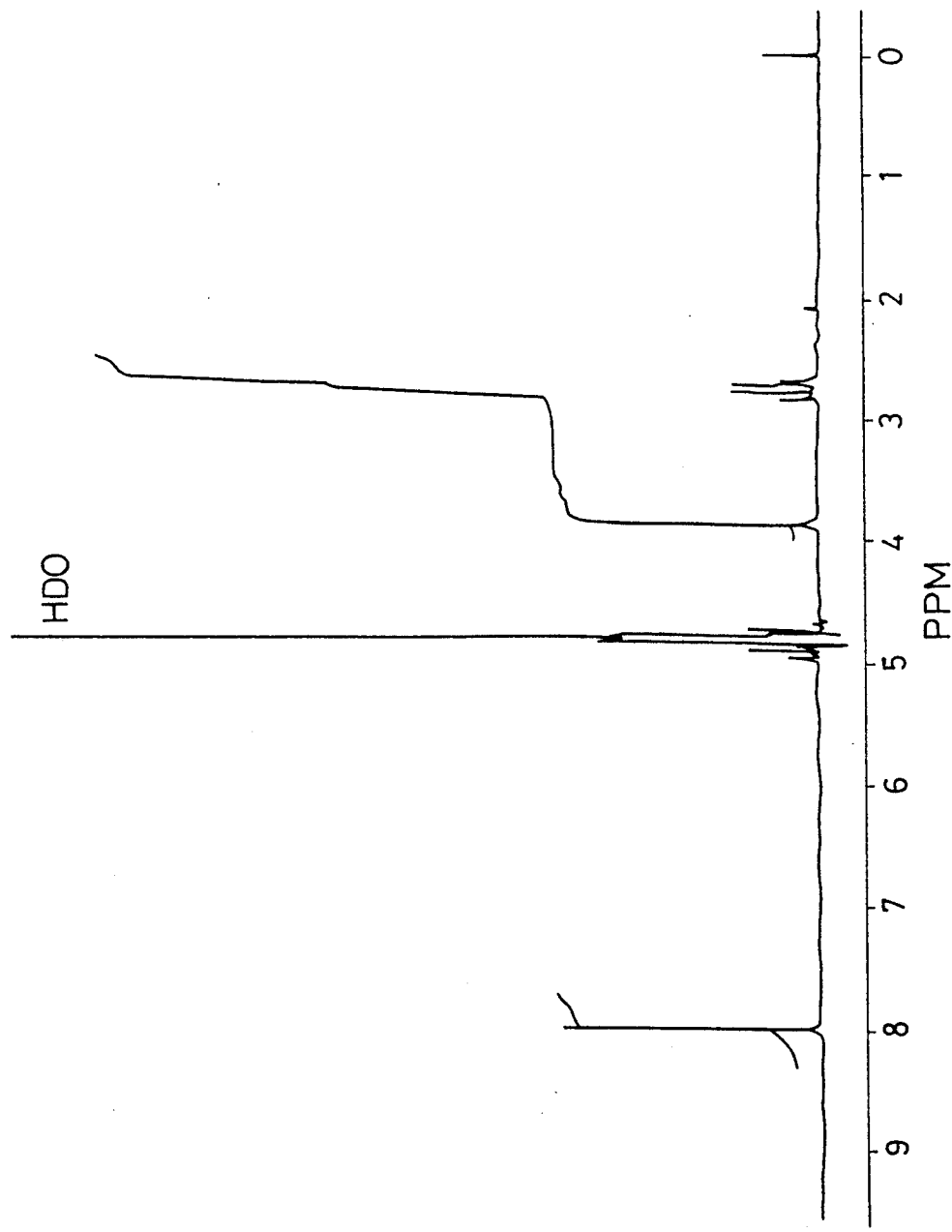
FIG. 5 shows the $^1H$ nuclear magnetic resonance spectrum (at 400 MHz, in deuterated water) of TAN-950A.

8) $^1$H-Nuclear magnetic resonance spectrum: 400 MHz, in deuterated water (cf. FIG. 5)
The following signals were observed

| $[\delta_{ppm}\ ^J(Hz)]$ |
|---|
| 2.70 (1H, dd, J=7.3, 15.6), |
| 2.80 (1H, dd, J=4.4, 15.6), |
| 3.86 (1H, dd, J=4.4, 7.3), |
| 7.98 (1H, s) |

Note:
dd: double doublet, s: singlet

Figure 6:
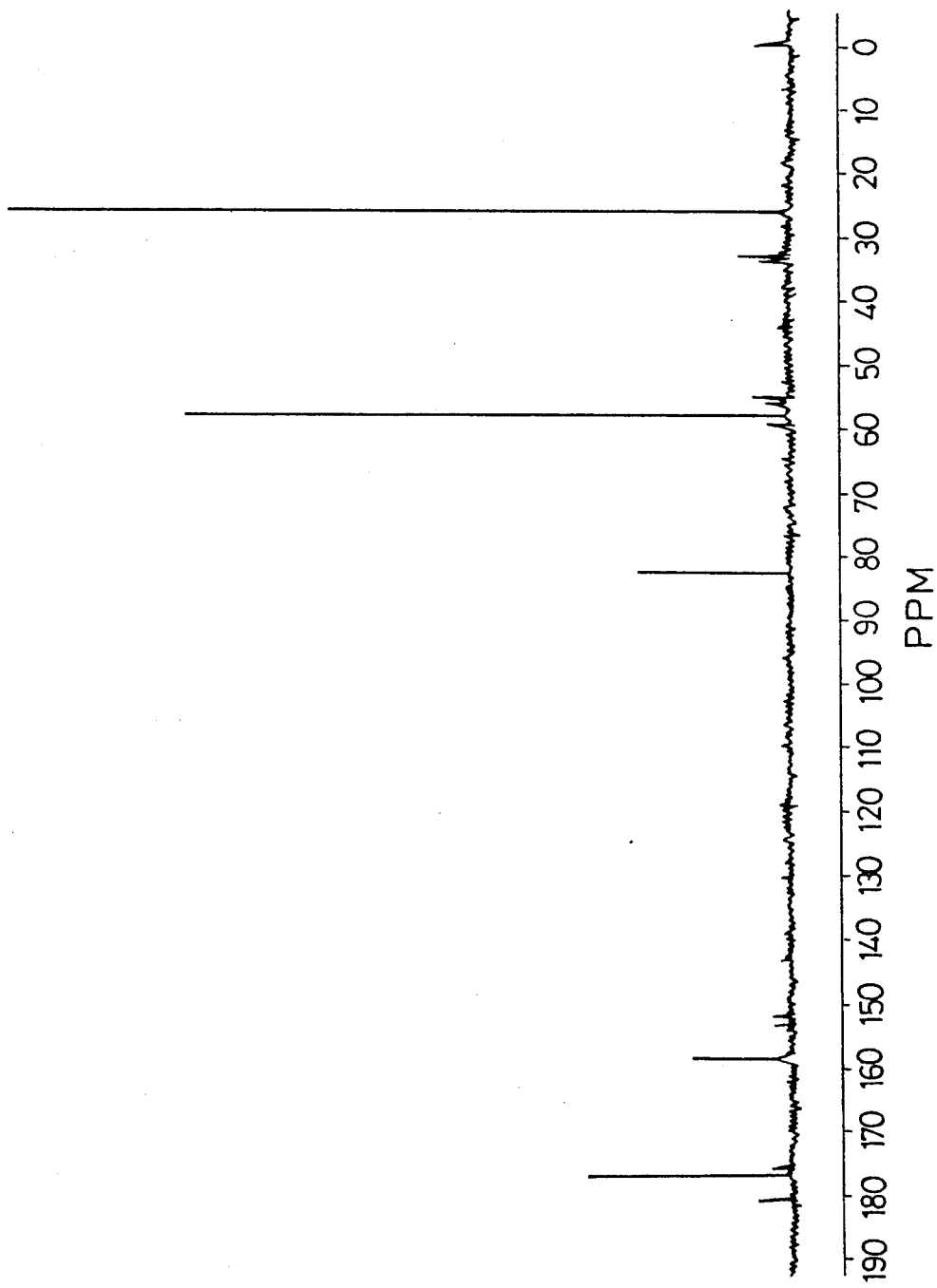
FIG. 6 shows the $^{13}C$ nuclear magnetic resonance spectrum (at 100 MHz, in deuterated water) of TAN-950A.

9) $^{13}$C-Nuclear magnetic resonance spectrum: 100 MHz, in deuterated water (cf. FIG. 6)
The following signals were observed

| $(\delta_{ppm})$ | | |
|---|---|---|
| 180.6 (s), | 177.1 (s), | 158.5 (d), |
| 82.9 (s), | 58.5 (d), | 26.5 (t) |

Note:
s: singlet, d: doublet, t: triplet

10) Solubility:
Soluble:
water, dimethylsulfoxide, methanol
Sparingly soluble:
ethyl acetate, acetone, chloroform 11) Color reaction:
Positive: Ninhydrin, Ehrlich's (acidic) Phosphomolybdate and Diethylaminobenzaldehyde reactions
Negative: Grag-Laybach and Dragendorff's reaction.

12) Thin layer chromatography (TLC):

| Carrier | Solvent system | Rf |
|---|---|---|
| Cellulose f*[1] | Acetonitrile:Water (4:1) | 0.11 |
| Silica gel GF$_{254}$*[2] | n-Butanol:Acetic acid:Water (2:1:1) | 0.17 |

*[1]Tokyo Chemicals, Ltd., Japan
*[2]E. Merck, W. Germany

13) High Performance Liquid Chromatography (HPLC):
Carrier; yMC-Pack AM-324 (Made by Yamamura Chemical, Japan), Mobile phase; 0.005M tetrabutylammonium hydroxyide/0.02M phosphoric acid buffer (pH 6.0), Flow speed; 2 ml/min., Rt=4.8 (min.)

14) Property of substance: Amphoteric substance

15) Amino acid analysis: TAN-950 A was heated in 6N hydrochloric acid at 100° C. for 16 hours and glutamic acid was detected by amino acid analysis.

The compounds of the aforesaid formulae (I) and (I') wherein $R^2$ is hydrogen can be also represented as enol-type compounds as shown below.

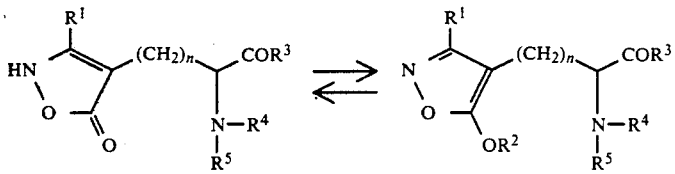

The enol-type compounds as shown above are also included in the concept of the present invention.

The compounds represented by the aforementioned formulae (I), (II), (I') and (II') contain one or more asymmetric carbons in their molecule, and both configurations of R and S and the mixture thereof are also included in the present invention Examples of the salts of the compounds (I), (II), (I') and (II') are inorganic salts such as hydrochloride, hydrobromide, sulfate, nitrate and phosphate; organic salts such as acetate, tartarate, citrate, fumarate, maleate, toluensulfonate and methanesulfonate; metallic salts such as sodium salt, potassium salt, calcium salt and aluminum salt; salts with bases such as triethyl- amine salt, guanidine salt, ammonium salt, hydrazine salt, quinine salt and cinchonine salt. And these salts can be obtained by the known methods.

In the following description on the process for the production, generic reference to "I" and "II" as the representatives of the objective compound includes reference to "I'" and "II'" respectively. Accordingly, reference to "n" includes reference to "n'".

The compound represented by the formula (I-1) of the present invention

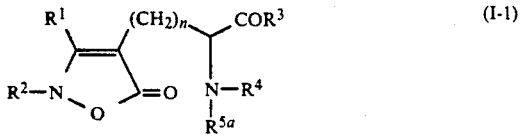

wherein $R^1$, $R^2$, —$COR^3$, $R^4$ and n have the same meanings as mentioned above, $R^{5a}$ is a chain or alicyclic hydrocarbon residue optionally having aryl substituent, can be obtained by condensing a compound represented by the formula (I-2)

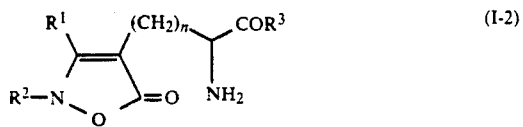

, wherein $R^1$, $R^2$, —$COR^3$ and n have the same meanings mentioned above, with a carbonyl compound under a reductive condition.

The chain or alicylic hydrocarbon residues optionally having aryl substituent as stated with respect to $R^5$ are applicable to those of the above $R^{5a}$.

Examples of the carbonyl compounds to be used in the said reaction are acetone, methyl ethyl ketone, methyl benzyl ketone, methyl phenyl ketone, formaldehyde, acetaldehyde, propionaldehyde, butyraldehyde, benzaldehyde, phenylacetaldehyde, phenylpropionaldehyde, cyclopropanecarbaldehyde, cyclobutanone, cyclopentanone, cyclohexanone, cycloheptanone and cyclohexanecarbaldehyde. It is preferable to use in this reaction the carbonyl compound of 1 to 50 equivalents and more preferaly 1 to 10 equivalents to the compound (I-2).

As to the reductive condition, it is preferable to use the reducing reagent such as lithium aluminum hydride, sodium borohydride, lithium borohydride, lithium cyanoborohydride or sodium cyanoborohydride. The reaction is normally conducted in water or an organic solvent (such as methanol, ethanol, dioxane or chloroform) or in the mixture thereof. The reaction temperature varies depending upon the type of the reducing agent. However, it is generally preferable to carry out the reaction at $-20°$ C. to room temperature and the preferable reaction time is approximately 30 minutes to 24 hours.

The compound represented by the formula (I-3) of the present invention

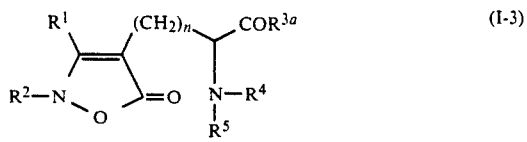

, wherein $R^1$, $R^2$, $R^4$, $R^5$ and n have the same meanings as those mentioned above, and —$COR^{3a}$ is an esterified or amidated carboxyl group, can be obtained by condensing a compound represented by the formula (I-4)

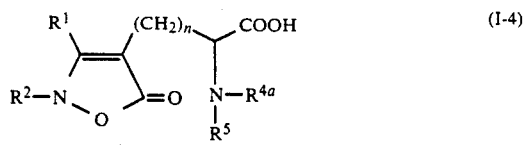

, wherein $R^1$, $R^2$, $R^5$ and n have the same meanings as mentioned above, and $R^{4a}$ is an acyl, with a compound represented by the formula (III)

, wherein $R^{3b}$ is an amine residue, alcohol residue or amino acid residue optionally being protected, and, if desired, by removing the protecting group.

Examples of the esterified or amidated carboxyl groups represented by —COR$^{3a}$ are those exemplified as the esterified or amidated carboxyl groups with respect to —COR$^3$.

Examples of the acyl groups represented by R$^{4a}$ are those exemplified as the acyl group represented by R$^4$.

Examples of the amine residues represented by R$^{3b}$ are such amino, C$_{1-10}$ alkylamino, C$_{3-7}$ cycloalkyl amino, aralkylamino and cyclic amino as mentioned above with respect to R$^3$ of —COR$^3$ group.

Examples of the alcohol residues represented by R$^{3b}$ are methoxy, ethoxy, tert-butoxy, isopropoxy, 2-cyanoethoxy, 2,2,2-trichloroethoxy, benzyloxy, p-nitrobenzyloxy, p-methoxybenzyloxy, diphenylmethyloxy, methoxymethyloxy, acetylmethyloxy, isobornyloxy or phenoxy, among which methoxy, ethoxy, tert-butoxy and p-nitrobenzyloxy are preferable.

Examples of the optionally protected amino acid residues represented by R$^{3b}$ are amino acid residues as mentioned above with respect to R$^3$ and, in case that R$^{3b}$ has a carboxyl or amino group, those may be the esterified carboxyl group or acylated amino group similarly to that mentioned above with respect to R$^3$.

In the condensation reaction, the compound (III) can be used preferably in 0.5 to 20 equivalents, more preferably 0.5 to 5 equivalents, to the compound (I-3).

The condensation reaction can be accelerated by using a condensing agent such as dicyclohexylcarbodiimide, carbonyldiimidazole, diethyl cyanophosphonate or diphenylphosphoryl azide and adding preferably an organic base such as quaternary ammonium salts or tertiary amines (e.g., triethylamine, N-methylpiperidine or N-methylmorpholine). The reaction is carried out normally at a temperature of approximately −20 to 50° C. and preferably at room temperature. Examples of the solvents to be used are dioxane, tetrahydrofuran, acetonitrile, N,N-dimethylformamide, N,N-dimethylacetamide, dimethylsulfoxide, N-methyl-pyrrolidone, chloroform and methylenechloride, and the reaction time is preferably about 30 minutes to 24 hours.

When R$^{3b}$ is an alcohol residue, an acid catalyst such as hydrogen chloride, hydrogen bromide or p-teluenesulfonic acid can be also used in the condensing reaction. The reaction is preferably carried out in an appropriate solvent or mixed solvents or without any solvent at a temperature in the range of about 0° C. to 50° C. for about 1 to 24 hours.

The removal for the protecting groups can be conducted by a method using an acid or a base, which is suitably selected depending upon the kind of the protecting group. Examples of the acids in the method using an acid are inorganic acids such as hydrogen chloride, hydrogen bromide, hydrogen fluoride, hydrogen iodide, methanesulfonic acid, p-toluenesulfonic acid, trifluoromethanesulfonic acid, sulfuric acid and phosphoric acid; organic acids such as formic acid, acetic acid, trifluoroacetic acid and propionic acid; or acid ion exchange resins while a suitable acid may be selected in consideration of the kind of the protecting group and other conditions. Examples of the bases in the method using a base are inorganic bases such as hydroxide or carbonate of an alkali metal (e.g., sodium or potassium) or alkaline earth metal (e.g., calcium or magnesium); metal alkoxides; organic bases such as organic amines or organic tertiary ammonium salts; or basic ion exchange resins, while a suitable one may be selected depending on the kind of the protecting groups and other conditions. When a solvent is used in the above mentioned method using acid or base, it may be water, methanol, ethanol, ethyl acetate, chloroform, tetrahydrofuran, dioxane, pyridine, acetic acid, acetone or methylene chloride. These solvents can be used singly or in mixture thereof. In case of the method which uses an acid and a metal, water or acetone is frequently used but if the acid is liquid, it can be used as solvent. In the method using an acid or a base, the reaction is normally carried out under cooling through warming condition for about 30 minutes through 20 hours.

Of the compounds in the present invention, the compound represented by the formula (I-5)

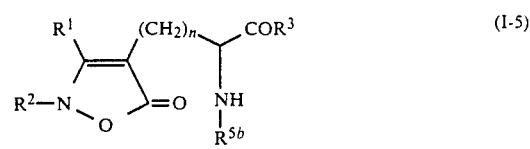
(I-5)

, wherein R$^1$, R$^2$, R$^3$ and n have the same meanings as those mentioned above and R$^{5b}$ is an amino acid residue, can be obtained by condensing a compound represented by the formula (I-6)

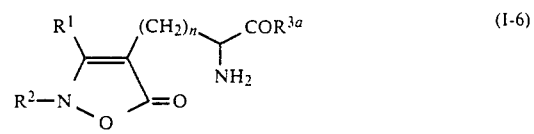
(I-6)

, wherein R$^1$, R$^2$, —COR$^{3a}$ and n have the same meanings as those mentioned above, and a compound represented by the formula (IV)

(IV)

, wherein R$^{5c}$ is a protected amino acid residue, and, if desired, removing the protecting group.

Examples of the amino acid residues in the protected amino acid residue represented by R$^{5c}$ are those similar to the amino acid residues mentioned above with respect to R$^5$. Examples of the protecting groups in the amino acid residue are acyl groups such as a C$_{2-15}$ alkanoyl (e.g., acetyl, propionyl, lauroyl), benzoyl, a phenyl-C$_{1-4}$ alkoxycarbonyl (e.g., benzyloxycarbonyl), a C$_{1-4}$ alkoxycarbonyl (e.g., tert-butoxycarbonyl), 4-methoxyfumaroyl and 4-aminofumaroyl.

In the aforementioned condensation reaction, the compound (IV) is used in approximately 0.5 to 10 equivalents, preferably 0.5 to 3 equivalents, to the amount of the compound (I-6).

As the reaction condition of the aforesaid condensation reaction, it is preferable either to use a condensing agent (e.g., dicyclohexylcarbodiimide, carbonyldiimdazole, diethyl cyanophosphonate, diphenylphosphoryl azide) or for obtaining the active ester form of the compound (IV) to condense the compound (IV) with a phenol (e.g., 2,4,5-trichlorophenol, pentachlorophenol, pentafluorophenol, 2-nitrophenol or 4-nitrophenol) or a N-hydroxy compound (e.g., N-hydroxysuccinimide, N-hydroxy-5-norbornene-2,3-dicarboximide, 1-hydroxybenzotriazole or N-hydroxypiperidine) in the present of a catalyst such as dicyclohexylcarbodiimide, and then to react the resulting active ester with the compound (I-6). It is also possible for obtaining the mixed acid anhydride to react at first the compound (IV) with, for example, methyl chlorocarbonate, ethyl chlorocarbonate or isobutyl chlorocarbonate, preferably in the presence of an organic base (e.g., triethylamine or N-methylmorpholine) and then to react the resulting mixed anhydride with the compound (I-6). This reaction is normally carried out at a temperature of about −30° C. to 50° C. Examples of the solvents to be used are dioxane, tetrahydrofuran, acetonitrile, diethyl ether, N,N-dimethylformamide, N,N-dimethylacetamide, dimethylsulfoxide, N-methylpyrrolidone, chloroform and ethylene chloride, which may be used singly or in mixture thereof.

The removal for the protecting group in the protected amino acid residue for $R^{5c}$ can be conducted in the same way as those described with respect to $R^{3b}$ in the condensation reaction of the compound (I-4) and the compound (III).

Of the compounds of the present invention, the compound represented by the formula (I-7)

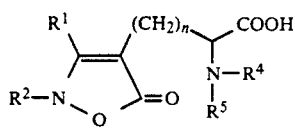

(I-7)

[wherein $R^1$, $R^2$, $R^4$, $R^5$ and n have the same meanings as those mentioned above] is obtained by removing a protecting group of a compound represented by the formula (I-8)

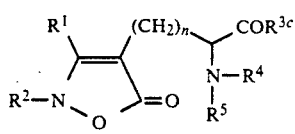

(I-8)

[wherein $R^1$, $R^2$, $R^4$, $R^5$ and n have the same meanings as those mentioned above and $R^{3c}$ is an esterified carboxyl group].

The esterified carboxyl groups, described with respect to —$COR^3$ are applicable to those for —$COR^{3c}$.

The removal for the protecting group can be conducted by using a method using an acid or a base. Examples of the acids are hydrochloric acid, hydrogen-bromide and trifluoroacetic acid and examples of the bases are sodium hydroxide, potassium hydroxide and potassium carbonate. The reaction is carried out in water or in an organic solvent such as methanol, ethanol, dioxane or tetrahydrofuran, or in a mixed solvent thereof at a temperature of approximately 0° C. to 30° C.

The amount of the acid or base to be used for the removal for the protecting group is 1 to 50 equivalents, preferably 1 to 10 equivalents to the compound (1–8).

Of the compounds belonging to this invention, the compound represented by the formula (I-9)

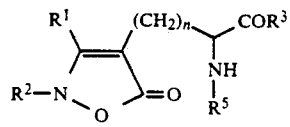

(I-9)

[wherein $r^1$, $R^2$, —$COR^3$, $R^5$ and n have the same meanings as those mentioned above] is obtained by removing a protecting group of a compound represented by the formula (I-10)

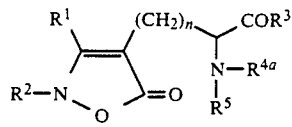

(I-10)

[wherein $R^1$, $R^2$, —$COR^3$, $R^{4a}$, $R^5$ and n have the same meanings as those mentioned above].

The removal for the protecting group in the compound (I-10) can be conducted in the same way as those described with respect to $R^{3b}$ *in the reaction of the compound* (I-4) and the compound (III).

Of the compounds in the invention, the compound represented by the formula (II-1)

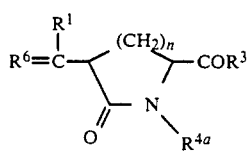

(II-1)

, wherein $R^1$, —$COR^3$, $R^{4a}$, $R^6$ and n have the same meanings as those mentioned above, can be obtained by acylating a compound represented by the formula (V)

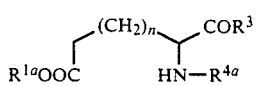

(V)

, wherein —$COR^3$, $R^{4a}$ and n have the same meanings as those mentioned above and —$COOR^{1a}$ is an esterified carboxyl group, or a compound represented by the formula (VI)

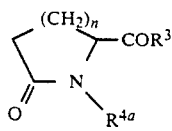

(VI)

, wherein —$COR^3$, $R^{4a}$ and n have the same meanings as those mentioned above, and then if necessary oximating the resultant.

By removing the protecting group of the compound of the formula (II-1) thus obtained, the compound of the formula (II) can be obtained.

Examples of $R^{1a}$ in the esterified carboxy group represented by —$COOR^{1a}$ are an alkyl, alkenyl, alkynyl, aryl, heteroaryl, aralkyl or cycloalkyl group and their specific examples are those similar to those indicated with respect to $R^1$.

The compound (II-1) in which $R^1$ is hydrogen atom or a $C_{1-3}$ alkyl group and $R^6$ is 0 [hereinafter referred to as the compound (II-2)] can be synthesized as follows. The compound (V) or (VI) is dissolved in an organic solvent such as tetrahydrofuran, ethyl ether or n-hexane or in a mixed solvent thereof, to which an activating reagent such as lithium diisopropylamide or lithium bistrimethylsilylamide is added at -100° C. to 40° C., preferably at −78° C. to 0° C. After the reaction mixture is kept for about 5 minutes to 2 hours and preferably for about 10 minutes to an hour, it is reacted with an acylating reagent such as ethyl formate, isopropyl formate, isobutyl formate, tert-butyl formate, acetylimidazole, propionylimidazole or butyrylimidazole at about −78° C. to room temperature, preferably at about −40° C. to 0° C. for 0.5 to 10 hours, preferably for about 1 to 4 hours.

In case of using the compounds (V) wherein n is zero [hereinafter referred to the compound (V-1)] as the starting compound in order to produce the compound (II-1), the compound represented by the formula (VII) is obtained,

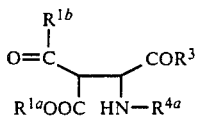  (VII)

wherein $R^{1b}$ is hydrogen or $C_{1-3}$ alkyl, and —COOR$^{1a}$, —COR$^3$ and R$^{4a}$ have the same meanings as those mentioned above.

In this reaction, the acylating agent is used in about 1 to 5 equivalents, preferably 1 to 2 equivalents, to the compound (V-1) or (VI-1) out of the compound (V) or (VI) in which n is zero.

The compound represented by the formula (VIII)

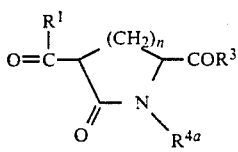  (VIII)

, wherein R$^1$, —COR$^{3,}$ R$^{4a}$ and n have the same meanings as those mentioned above and the compound represented by the formula (IX)

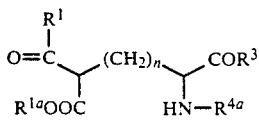  (IX)

, wherein R$^1$, —COOR$^{1a}$, —COR$^3$, R$^{4a}$ and n have the same meanings as those mentioned above, can be prepared by the following methods.

The methylene group adjacent to the carbonyl group in the compound (V) or (VI) is activated and is reacted with an aldehyde derivative, followed by an oxidation, preferably Swern's oxidation. That is: the compound (V) or (VI) is dissolved in an organic solvent such as tetrahydrofuran, ethyl ether or n-hexane or in a mixed solvent thereof and reacted with an activating reagent such as lithium diisopropylamide or lithium bistrimethylsilylamide at about −100° C. to 40° C., preferably at about −78° C. to 0° C. for about 5 minutes to 2 hours, preferably for about 10 minutes to an hour. Then, the mixture is further reacted, at about −78° C. to room temperature, preferably about −40° C. to 0° C. for about 0.5 to 10 hours, preferably about 1 to 4 hours, with an aldehyde such as formaldehyde, and an alkylaldehyde (e.g., acetaldehyde, propionaidehyde, butyraldehyde, isobutyraldehyde, valeraldehyde or isovaleraldehyde), an arylaldehyde (e.g., benzaldehyde, 1-naphthaldehyde, 2-naphthaldehyde), an aralkylaldehyde (e.g., phenylacetaldehyde, phenylpropionaldehyde or phenylbutyraldehyde), a heteroarylaldehyde (e.g., nicotinaldehyde, isonicotinaldehyde, 3-furancarbaldehyde, 2-thiophenecarbaldehyde or 3-thiophenecarbaldehyde), a cycloalkylcarbaldehyde (e.g., cyclopropanecarbaldehyde, cyclobutanecarbaldehyde, cyclopentanecarbaldehyde, cyclohexanecarbaldehyde or cycloheptanecarbaldehyde).

In the reaction, the aldehyde derivative is used in about 1 to 5 equivalents, preferably 1 to 2 equivalents, to the compound (V) or (VI).

The reaction affords a compound represented by the formula (X)

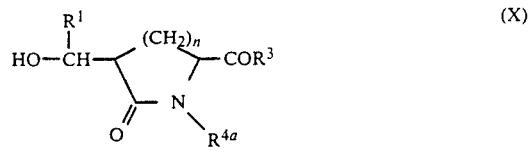  (X)

, wherein R$^1$, —COR$^{3,}$ R$^{4a}$ and n have the same meanings as those mentioned above, and a compound represented by the formula (XI) oxalyl chloride

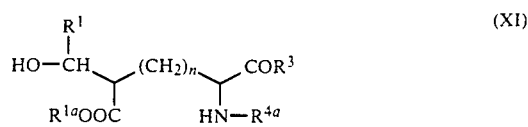  (XI)

, wherein R$^1$, —COOR$^{1a}$, —COR$^3$, R$^{4a}$ and n have the same meanings as those mentioned above.

The oxidation of the compound (X) or (XI) is carried out as follows: oxalylchloride or trifluoroacetic anhydride of about 1 to 2 equivalents to the compound (X) or (XI) is dissolved in an organic solvent (e.g., a single solvent of ethylene chloride, chloroform, tetrahydrofuran and dimethyl ether or a mixed solvent thereof) and dimethylsulfoxide is dropped therein at −100° C. to 0° C. After about one minute to an hour, preferably 2 to 10 minutes, the compound (X) or (XI) is added to the reaction mixture and kept at about −100° C. to room temperature, preferably at about −78° C. to 0° C. for about 5 minutes to an hour, preferably about 10 to 30 minutes. Then, an organic amine (e.g, triethylamine, N-methylmorpholine, diethylisopropylamine, etc.) is added to the reaction mixture and kept at about −100° C. to room temperature, preferably at about −78° C. to room temperature, to obtain the compound (VIII) or (IX).

The compound (II-1) in which R$^6$ is —NOH [hereinafter referred to as compound (II-3)] is obtained by oximation of the compound (VIII).

The oximation reaction is carried out by dissolving the compound (VIII) in an aqueous solution such as aqueous dioxane, aqueous tetrahydrofuran, aqueous methanol or aqueous ethanol, and hydroxylamine or its salt of about 1 to 3 equivalents, preferably of 1.2 to 2.0 equivalents is added thereto and the reaction is continued for 10 minutes to 5 hours at 0° C. to reflux temperature.

The compound thus obtained (II-3) is dissolved in an alcohol such as methanol and an alkaline solution of about 1 equivalent is added thereto, or an alkaline solution is added to the reaction mixture of said oximation reaction, and preferably after adjusting it at pH 7, the reaction is continued with stirring at about −20° C. to 40° C., preferably 0° C. to room temperature for about 10 minutes to 4 hours, preferably for about 30 minutes to 2 hours. This reaction affords the compound (I-11) in the formula (I) in which R$^2$ and R$^5$ are both hydrogen atoms and R$^4$ is an acyl group or a chain or alicyclic hydrocarbon residue optionally having an aryl substituent. In this reaction, the compound (I-11) can be also obtained from the compound (VIII) without isolation of the intermediate compound (II-3).

Moreover, the compound (I-11) can be also obtained by subjecting the compound (IX) to the same oximation reaction as that described above.

The salt of the compounds (I) or (II) can be obtained directly through the reaction of producing the compounds (1) and (II), but obtained by adding an acid or base to the compounds (I) or (II).

The compounds (I) and (II) of this invention thus formed can be isolated and purified from the reaction mixture by a conventional method such as extraction, concentration, neutralization, filtration, recrystallization, column chromatography and thin layer chromatography.

The compounds (I) or (II) may exist as at least two stereoisomers. If desired, individual stereoisomers of the compound (I) or (II) can be obtained. For example, it is possible to obtain one isomer of the compound (I) or (II) by conducting the reaction using as the starting compound a single isomer of the respective compound. Alternatively, when the product is in the mixture of two or more of isomers, the respective isomer can be obtained by the conventional separation methods such as the formation of salt with an optically active acid (e.g., camphor sulfonic acid, tartaric acid or benzol tartaric acid), an optically active base (e.g., cinchonine, cinchonidine, quinine, quinidine, α-methylbenzylamine, dehydro- or abiethylamine), various chromatographies or fractional recrystallization or the like.

The structural formulae of TAN-950A, other TAN-950 group and the derivatives thereof obtained in accordance with Examples as disclosed later are as follows.

Herein, the following abbreviations are used.

φ: phenyl,
Boc: t-butoxycarbonyl,
Bu$^t$: t-butyl,
Cbz: benzyloxycarbonyl,
PNB: p-nitrobenzyl.

| Compound No. | Sample name | Chemical structure |
|---|---|---|
| 1 | TAN-950A | |
| 2 | TAN-950B | |
| 3 | TAN-950C | |
| 4 | TAN-950D | |
| 5 | TAN-950E | 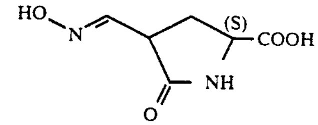 |
| 6 | TAN-950A-E | Mixture of Compounds 1-5 |
| 7 | N-benzoyl TAN-950A | 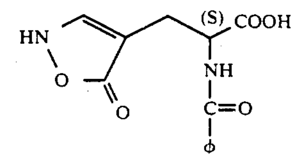 |
| 8 | N-acetyl TAN-950A | 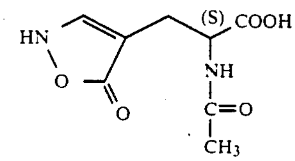 |
| 9 | N—Boc TAN-950A | 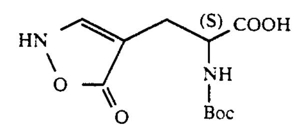 |
| 10 | N'-methyl TAN-950A | 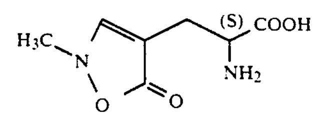 |
| 11 | N—Boc—N'-acetyl TAN-950A | 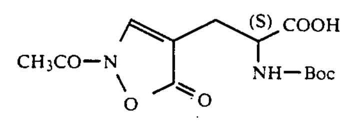 |
| 12 | TAN-950A methyl ester | 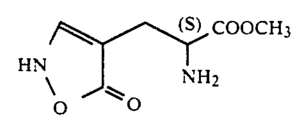 |
| 13 | O-methyl N-benzoyl TAN-950A methyl ester | 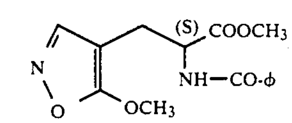 |
| 14 | N'-methyl N-benzoyl TAN-950A methyl ester | 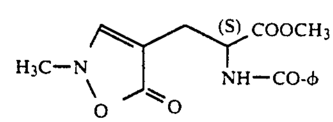 |
| 15 | TAN-950A tri-(p-nitrobenzyl) ester | 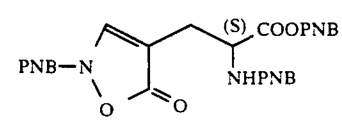 |
| 16 | any one of TAN-950A-E p-nitrobenzyl ester | 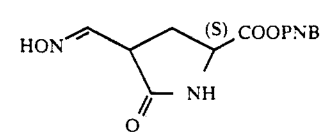 |

-continued

| Compound No. | Sample name | Chemical structure |
|---|---|---|
| 17 | γ-formyl-N-Boc—L-pyroglutamic acid methyl ester | OHC—[(S) pyrrolidinone ring]—COOCH$_3$, N-Boc |
| 18 | oxime of Compound 17 | HON=CH—[(S) pyrrolidinone ring]—COOCH$_3$, N-Boc |
| 19 | N—Boc-TAN-950A methyl ester | [isoxazolone ring, HN-O, =O]—CH$_2$—CH(S)(COOCH$_3$)(NH—Boc) |
| 20 | N,N'-di Boc TAN-950A | [isoxazolone ring, Boc-N-O, =O]—CH$_2$—CH(S)(COOH)(NH—Boc) |

TABLE 3

$$\text{Structure: } R^1\text{-[isoxazolone ring, HN-O, =O]-CH}_2\text{-C*H(COR}^3\text{)(NR}^4R^5)$$

| Compound No. | Configuration C* | R$^1$ | NR$^4$R$^5$ | R$^3$ |
|---|---|---|---|---|
| 21 | S | H | N(CH$_3$)$_2$ | OH |
| 22 | S | H | NHCH(CH$_3$)(CH$_2$)$_2$—C$_6$H$_5$ | OH |
| 23 | S | H | NHCH(CH$_3$)$_2$ | OH |
| 24 | S | H | NHC(O)—CH(S)(NHBoc)(CH$_3$) | OCH$_3$ |
| 25 | S | H | NHC(O)—CH(S)(NHBoc)(CH$_3$) | OH |
| 26 | S | H | NHC(O)—CH(S)(NH$_2$)(CH$_3$) | OH |
| 27 | S | H | NHC(O)—CH(S)(NHBoc)((CH$_2$)$_2$CH$_3$) | OCH$_3$ |
| 28 | S | H | NHC(O)—CH(S)(NHBoc)((CH$_2$)$_2$CH$_3$) | OH |
| 29 | S | H | NHC(O)—CH(S)(NH$_2$)((CH$_2$)$_2$CH$_3$) | OH |

TABLE 3-continued $$\text{Structure: R}^1\text{-isoxazolone-CH}_2\text{-C*H(COR}^3\text{)-N(R}^4\text{)(R}^5\text{)}$$

| Compound No. | Configuration C* | R$^1$ | N(R$^4$)(R$^5$) | R$^3$ |
|---|---|---|---|---|
| 30 | S | H | NHC(O)—C(S)H(NHBoc)(CH$_2$)$_3$CH$_3$ | OCH$_3$ |
| 31 | S | H | NHC(O)—C(S)H(NHBoc)(CH$_2$)$_3$CH$_3$ | OH |
| 32 | S | H | NHC(O)—C(S)H(NH$_2$)(CH$_2$)$_3$CH$_3$ | OH |
| 33 | S | H | NHC(O)—C(S)H(NHBoc)CH$_2$CH(CH$_3$)$_2$ | OCH$_3$ |
| 34 | S | H | NHC(O)—C(S)H(NHBoc)CH$_2$CH(CH$_3$)$_2$ | OH |
| 35 | S | H | NHC(O)—C(S)H(NH$_2$)CH$_2$CH(CH$_3$)$_2$ | OH |
| 36 | S | H | NHC(O)—C(S)H(NHBoc)(CH$_2$)$_2$SCH$_3$ | OCH$_3$ |
| 37 | S | H | NHC(O)—C(S)H(NHBoc)(CH$_2$)$_2$SCH$_3$ | OH |
| 38 | S | H | NHC(O)—C(S)H(NH$_2$)(CH$_2$)$_2$SCH$_3$ | OH |
| 39 | S | H | NHC(O)—C(S)H(NHC(O)(CH$_2$)$_{10}$CH$_3$)CH$_3$ | OCH$_3$ |
| 40 | S | H | NHC(O)—C(S)H(NHC(O)(CH$_2$)$_{10}$CH$_3$)CH$_3$ | OH |
| 41 | S | H | NHC(O)—C(S)H(NHCbz)CH$_2$NHBoc | OCH$_3$ |

TABLE 3-continued

Structure:
$$R^1\text{-isoxazolone-CH}_2\text{-}{}^*\text{CH}(COR^3)\text{-N}(R^4)(R^5)$$

| Compound No. | Configuration C* | $R^1$ | $N(R^4)(R^5)$ | $R^3$ |
|---|---|---|---|---|
| 42 | S | H | NHC(O)-(S)CHNHCbz-CH₂NHBoc | OH |
| 43 | S | H | NHC(O)-(S)CHNHCbz-CH₂NH₂ | OH |
| 44 | S | H | NHC(O)-(S)CHNHBoc-CH₂NHBoc | OCH₃ |
| 45 | S | H | NHC(O)-(S)CHNHBoc-CH₂NHBoc | OH |
| 46 | S | H | NHC(O)-(S)CHNH₂-CH₂NH₂ | OH |
| 47 | S | H | NHBoc | (S) NHCHCOOBu$^t$ / CH₃ |
| 48 | S | H | NH₂ | (S) NHCHCOOH / CH₃ |
| 49 | S | H | NHBoc | (S) NHCHCOOPNB / (CH₂)₂CH₃ |
| 50 | S | H | NHBoc | (S) NHCHCOOH / (CH₂)₂CH₃ |
| 51 | S | H | NH₂ | (S) NHCHCOOH / (CH₂)₂CH₃ |
| 52 | S | H | NHBoc | (S) NHCHCOOPNB / (CH₂)₃CH₃ |
| 53 | S | H | NHBoc | (S) NHCHCOOH / (CH₂)₃CH₃ |
| 54 | S | H | NH₂ | (S) NHCHCOOH / (CH₂)₃CH₃ |

TABLE 3-continued

Structure: R¹ group attached to isoxazolone (HN-O-C(=O)-C=) with CH₂-C*H(COR³)(NR⁴R⁵) substituent

| Compound No. | Configuration C* | R¹ | N(R⁴)(R⁵) | R³ |
|---|---|---|---|---|
| 55 | S | H | NHBoc | (S) NHCHCOOBu$^t$ / CH₂CH(CH₃)₂ |
| 56 | S | H | NH₂ | (S) NH₂CHCOOH / CH₂CH(CH₃)₂ |
| 57 | S | H | NHBoc | (S) NHCHCOOC₂H₅ / (CH₂)₂SCH₃ |
| 58 | S | H | NHBoc | (S) NHCHCOOH / (CH₂)₂SCH₃ |
| 59 | S | H | NH₂ | (S) NHCHCOOH / (CH₂)₂SCH₃ |
| 60 | S | H | NH₂ | (S) NHCHCOOC₂H₅ / (CH₂)₂SCH₃ |
| 61 | S | H | NHBoc | (S) NHCH₂CHNHCbz / COOCH₃ |
| 62 | S | H | NHBoc | (S) NHCH₂CHNHCbz / COOH |
| 63 | S | H | NH₂ | (S) NHCH₂CHNHCbz / COOH |
| 64 | S | H | NHBoc | NHCH₂COOC₂H₅ |
| 65 | S | H | NHBoc | NHCH₂COOH |
| 66 | S | H | NH₂ | NHCH₂COOH |
| 67 | S | H | NHBoc | NH(CH₂)₂ / COOC₂H₅ |
| 68 | S | H | NHBoc | NH(CH₂)₂COOH |
| 69 | S | H | NH₂ | NH(CH₂)₂COOH |
| 70 | R | H | NHBoc | OCH₃ |
| 71 | R | H | NHBoc | OH |
| 72 | R | H | NH₂ | OH |
| 73 | S | CH₃ | NHBoc | OCH₃ |
| 74 | S | CH₃ | NHBoc | OH |
| 75 | S | CH₃ | NH₂ | OH |
| 76 | R | CH₃ | NHBoc | OCH₃ |
| 77 | R | CH₃ | NHBoc | OH |
| 78 | R | CH₃ | NH₂ | OH |
| 79 | S | CH₂CH₃ | NHBoc | OCH₃ |
| 80 | S | CH₂CH₃ | NHBoc | OH |
| 81 | S | CH₂CH₃ | NH₂ | OH |
| 82 | S | CH(CH₃)₂ | NHBoc | OCH₃ |
| 83 | S | CH(CH₃)₂ | NHBoc | OH |
| 84 | S | CH(CH₃)₂ | NH₂ | OH |

TABLE 3-continued
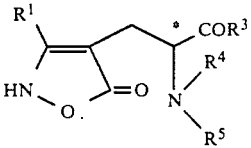
| Compound No. | Configuration C* | R¹ | NR⁴R⁵ | R³ |
|---|---|---|---|---|
| 85 | S | phenyl | NHBoc | OCH₃ |
| 86 | S | phenyl | NHBoc | OH |
| 87 | S | phenyl | NH₂ | OH |
| 88 | S | H | NHBoc | piperidinyl |
| 89 | S | H | NH₂ | piperidinyl |
| 90 | S | H | NHC(O)—CH(S)(NHBoc)(CH₂Ph) | OCH₃ |
| 91 | S | H | NHC(O)—CH(S)(NHBoc)(CH₂Ph) | OH |
| 92 | S | H | NHC(O)—CH(S)(NH₂)(CH₂Ph) | OH |

TABLE 4

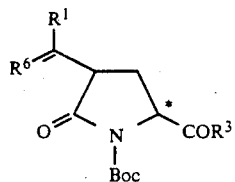

| Compound No. | Configuration C* | R¹ | R³ | R⁶ |
|---|---|---|---|---|
| 93 | R | H | OCH₃ | O |
| 94 | R | H | OCH₃ | NOH |
| 95 | S | CH₃ | OCH₃ | O |
| 96 | R | CH₃ | OCH₃ | O |
| 97 | S | CH₂CH₃ | OCH₃ | O |
| 98 | S | CH(CH₃)₂ | OCH₃ | O |
| 99 | S | ⟨phenyl⟩ | OCH₃ | O |
| 100 | S | H | OBuᵗ | O |
| 101 | S | H | OBuᵗ | NOH |
| 102 | | ⟨isoxazolone-CH(NHBoc)COOCH₃ (S)⟩ | | |

TABLE 4-continued

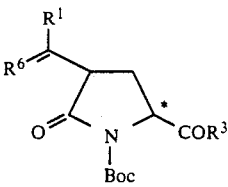

| Compound No. | Configuration C* | R¹ | R³ | R⁶ |
|---|---|---|---|---|
| 103 | | ⟨isoxazolone-CH(NHBoc)COOH (S)⟩ | | |
| 104 | | ⟨isoxazolone-CH(NH₂)COOH (S)⟩ | | |

TABLE 3-2

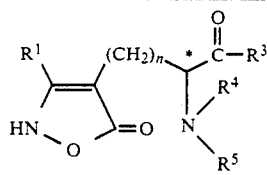

| Compound No. | n | Configuration C* | R¹ | NR⁴R⁵ | R³ |
|---|---|---|---|---|---|
| 105 | 1 | S | H | NHBoc | NH(CH₂)₃COOC₂H₅ |
| 106 | 1 | S | H | NHBoc | NH(CH₂)₃COOH |
| 107 | 1 | S | H | NH₂ | NH(CH₂)₃COOH |
| 108 | 1 | S | H | NHBoc | NH(CH₂)₄COOC₂H₅ |
| 109 | 1 | S | H | NHBoc | NH(CH₂)₄COOH |
| 110 | 1 | S | H | NH₂ | NH(CH₂)₄COOH |
| 111 | 1 | S | H | NHBoc | ⟨N-phenylpiperazinyl⟩ |
| 112 | 1 | S | H | NH₂ | ⟨N-phenylpiperazinyl⟩ |
| 113 | 1 | S | H | NHBoc | NHCH(CH₃)Ph (S) |
| 114 | 1 | S | H | NH₂ | NHCH(CH₃)Ph (S) |

TABLE 3-2-continued $$\text{structure: R}^1\text{-substituted isoxazolone with }(CH_2)_n\text{-}\overset{*}{C}H(C(O)R^3)(NR^4R^5)$$

| Compound No. | n | Configuration C* | R¹ | N(R⁴)(R⁵) | R³ |
|---|---|---|---|---|---|
| 115 | 1 | S | H | NHBoc | (S) NHCH₂CH(NHBoc)COOCH₃ |
| 116 | 1 | S | H | NHBoc | (S) NHCH₂CH(NHBoc)COOH |
| 117 | 1 | S | H | NH₂ | (S) NHCH₂CH(NH₂)COOH |
| 118 | 1 | S | H | NHBoc | (R) NHCH₂CH(NHBoc)COOCH₃ |
| 119 | 1 | S | H | NHBoc | (R) NHCH₂CH(NHBoc)COOH |
| 120 | 1 | S | H | NH₂ | (R) NHCH₂CH(NH₂)COOH |
| 121 | 1 | S | H | NHBoc | NHCH₂–C₆H₄–COOCH₃ |
| 122 | 1 | S | H | NHBoc | NHCH₂–C₆H₄–COOH |
| 123 | 1 | S | H | NH₂ | NHCH₂–C₆H₄–COOH |
| 124 | 1 | S | H | NHBoc | piperidin-1-yl-4-COOC₂H₅ |
| 125 | 1 | S | H | NHBoc | piperidin-1-yl-4-COOH |
| 126 | 1 | S | H | NH₂ | piperidin-1-yl-4-COOH |

TABLE 3-2-continued

Structure: R¹ on isoxazolone ring (HN-O-C(=O)-C=C(R¹)-) with (CH₂)ₙ-C*H(NR⁴R⁵)-C(=O)-R³ substituent

| Compound No. | n | Configuration C* | R¹ | NR⁴R⁵ | R³ |
|---|---|---|---|---|---|
| 127 | 1 | S | H | NHBoc | 3-(methoxycarbonyl)piperidin-1-yl (N-piperidine, 3-COOCH₃) |
| 128 | 1 | S | H | NHBoc | 3-carboxypiperidin-1-yl (N-piperidine, 3-COOH) |
| 129 | 1 | S | H | NH₂ | 3-carboxypiperidin-1-yl (N-piperidine, 3-COOH) |
| 130 | 1 | S | H | NHBoc | 2-(methoxycarbonyl)piperidin-1-yl (N-piperidine, 2-COOCH₃) |
| 131 | 1 | S | H | NHBoc | 2-carboxypiperidin-1-yl (N-piperidine, 2-COOH) |
| 132 | 1 | S | H | NH₂ | 2-carboxypiperidin-1-yl (N-piperidine, 2-COOH) |
| 133 | 1 | S | H | NHBoc | (S)-NHCH(CH₂-C₆H₄-4-OH)COOCH₃ |
| 134 | 1 | S | H | NHBoc | (S)-NHCH(CH₂-C₆H₄-4-OH)COOH |

TABLE 3-2-continued

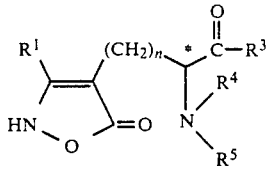

| Compound No. | n | Configuration C* | R¹ | NR⁴R⁵ | R³ |
|---|---|---|---|---|---|
| 135 | 1 | S | H | NH₂ | (S) NHCHCOOH–CH₂–C₆H₄–OH |
| 136 | 1 | S | H | NHC(O)–CH(NHBoc)CH₂NHC(O)–CH=CH–C(O)NH₂ (S) | OCH₃ |
| 137 | 1 | S | H | NHC(O)–CH(NHBoc)CH₂NHC(O)–CH=CH–C(O)NH₂ (S) | OH |
| 138 | 1 | S | H | NHC(O)–CH(NH₂)CH₂NHC(O)–CH=CH–C(O)NH₂ (S) | OH |
| 139 | 1 | S | H | NHC(O)–CH(NHBoc)CH₂SCH₂CH₂NHBoc (R) | OCH₃ |
| 140 | 1 | S | H | NHC(O)–CH(NHBoc)CH₂SCH₂CH₂NHBoc (R) | OH |
| 141 | 1 | S | H | NHC(O)–CH(NH₂)CH₂SCH₂CH₂NH₂ (R) | OH |
| 142 | 1 | S | H | NHC(O)–CH(NHBoc)CH₂SCH₂CH₂NHBoc (R) | (S) NHCHCOOCH₃–CH₂–C₆H₄–OH |
| 143 | 1 | S | H | NHC(O)–CH(NHBoc)CH₂SCH₂CH₂NHBoc (R) | (S) NHCHCOOH–CH₂–C₆H₄–OH |

TABLE 3-2-continued

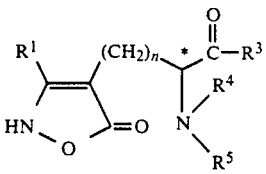

| Compound No. | n | Configuration C* | R¹ | NR⁴R⁵ | R³ |
|---|---|---|---|---|---|
| 144 | 1 | S | H | NHC(=O)(R)-CHCH₂SCH₂CH₂NH₂ with NH₂ | (S) NHCHCOOH-CH₂-C₆H₄-OH |
| 145 | 1 | S | H | NHC(=O)(R)-CHCH₂SCH₂CH₂NHBoc with NHBoc (O above) | OH |
| 146 | 1 | S | H | NHC(=O)(R)-CHCH₂SCH₂CH₂NH₂ with NH₂ (O above) | OH |
| 147 | 0 | R | H | NHBoc | OCH₃ |
| 148 | 0 | R | H | NHBoc | OH |
| 149 | 0 | R | H | NH₂ | OH |
| 150 | 2 | RS | CH₃ | NHBoc | OCH₃ |
| 151 | 2 | RS | CH₃ | NHBoc | OH |
| 152 | 2 | RS | CH₃ | NH₂ | OH |
| 153 | 0 | R | CH₃ | NHBoc | OCH₃ |
| 154 | 0 | R | CH₃ | NHBoc | OH |
| 155 | 0 | R | CH₃ | NH₂ | OH |
| 156 | 1 | S | cyclopentyl | NHBoc | OCH₃ |
| 157 | 1 | S | cyclopentyl | NHBoc | OH |
| 158 | 1 | S | cyclopentyl | NH₂ | OH |
| 159 | 1 | S | benzyl (C₆H₅CH₂) | NHBoc | OCH₃ |
| 160 | 1 | S | benzyl (C₆H₅CH₂) | NHBoc | OH |

TABLE 4-2

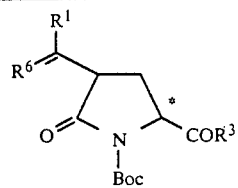

| Compound No. | Configuration C* | R¹ | R³ | R⁶ |
|---|---|---|---|---|
| 161 | S | cyclopentyl | OCH₃ | O |
| 162 | S | benzyl (–CH₂–C₆H₅) | OCH₃ | O |

TABLE 4-2-continued

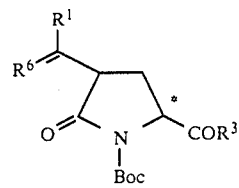

| Compound No. | Configuration C* | R¹ | R³ | R⁶ |
|---|---|---|---|---|
| 163 | S | 2-furyl-methyl | OCH₃ | O |
| 164 | S | cyclopropyl-methyl | OCH₃ | O |

TABLE 3-3

$$\underset{\underset{O}{HN}}{\overset{R^1}{\diagdown}}{\diagup}\overset{(CH_2)_n}{\diagdown}\overset{*}{C}\overset{O}{\underset{\underset{R^5}{N}}{\diagdown}}\overset{\parallel}{C}-R^3$$

| Compound No. | n | Configuration C* | R¹ | NR⁴R⁵ | R³ |
|---|---|---|---|---|---|
| 165 | 1 | S | H | NHBoc | pyrrolidine-(S)-COOCH₃ |
| 166 | 1 | S | H | NHBoc | pyrrolidine-(S)-COOH |
| 167 | 1 | S | H | NH₂ | pyrrolidine-(S)-COOH |
| 168 | 1 | S | H | NHBoc | pyrrolidine-(R)-COOCH₃ |
| 169 | 1 | S | H | NHBoc | pyrrolidine-(R)-COOH |

TABLE 3-3-continued

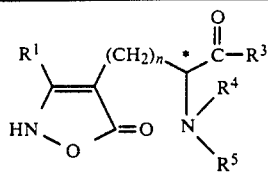

| Compound No. | n | Configuration C* | R¹ | NR⁴R⁵ | R³ |
|---|---|---|---|---|---|
| 170 | 1 | S | H | NH₂ | 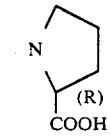 (R)-pyrrolidine-2-COOH |
| 171 | 1 | S | cyclopropyl | NHBoc | OCH₃ |
| 172 | 1 | S | cyclopropyl | NHBoc | OH |
| 173 | 1 | S | cyclopropyl | NH₂ | OH |
| 174 | 0 | S | CH₃ | NHBoc | OCH₃ |
| 175 | 0 | S | CH₃ | NHBoc | OH |
| 176 | 0 | S | CH₃ | NH₂ | OH |
| 177 | 0 | RS | CH₃ | NH₂ | OH |
| 178 | 0 | R | CH₃CH₂ | NHBoc | OCH₃ |
| 179 | 0 | R | CH₃CH₂ | NHBoc | OH |
| 180 | 0 | R | CH₃CH₂ | NH₂ | OH |
| 181 | 0 | R | (CH₃)₂CH | NHBoc | OH |
| 182 | 0 | R | (CH₃)₂CH | NH₂ | OH |
| 183 | 1 | S | H | NHBoc | NHCH(CH₃)-1-naphthyl (R) |
| 184 | 1 | R | H | NHBoc | NHCH(CH₃)-1-naphthyl (R) |
| 185 | 1 | S | CH₃ | NHBoc | NHCH(CH₃)-1-naphthyl (R) |
| 186 | 1 | R | CH₃ | NHBoc | NHCH(CH₃)-1-naphthyl (R) |

TABLE 3-3-continued

[Structure: R¹ with (CH₂)ₙ, C*−C(=O)−R³, R⁴, N, R⁵; HN−O−C(=O) isoxazole ring]

| Compound No. | n | Configuration C* | R¹ | N(R⁴)(R⁵) where R⁵ = | R³ |
|---|---|---|---|---|---|
| 187 | 0 | S | CH₃ | NHBoc | NHCH(CH₃)−(1-naphthyl) (R) |
| 188 | 0 | R | CH₃ | NHBoc | NHCH(CH₃)−(1-naphthyl) (R) |

TABLE 3-4

| Compound No. | Chemical structure |
|---|---|
| 189 | cyclopentane with COOMe, NHCO, NHBoc, CH=C−N(Boc)−O−C(=O) isoxazoline |
| 190 | cyclopentane with COOH, NHCO, NHBoc, CH=C−NH−O−C(=O) isoxazoline |
| 191 | cyclopentane with COOH, NHCO, NH₂, CH=C−N(H)−O−C(=O) isoxazoline |

The conversion of Compound 6 into Compound 1 can be effectively achieved by an alkali treatment. That is: the said compound is dissolved in an aqueous 0.1 to 1.0 N, preferably 0.2 to 0.5 N sodium hydroxide to make a concentration of 5 to 50 mg/ml, preferably 15 to 30 mg/ml. The reaction is carried out at 20° C. to 80° C., preferably at 40° C. to 70° C. for 15 minutes to 2 days, preferably for 30 minutes to 4 hours.

The method of introducing the protecting group is referred to in T. W. Greene: "Protective Groups in Organic Synthesis", p. 218 (1981, John Willy & Sons). The representative N-protective group, tert-butoxy carbonyl group is introduced into a compound by dissolving the compound in 50% dioxane-water, adding about 1-4 equivalent weights of triethylamine and about 1 to 3 equivalent weights of 2-(tert-butoxycarbonylox-Yimino)-2-phenyl-acetonitrile (hereinafter called as "BOC-ON") and allowing to react the mixture for 0.5 to 24 hours, preferably for 3 to 10 hours under stirring at room temperature.

The introduction of p-methoxybenzyloxycarbonyl group can be performed similarly. The introduction of a benzoyl group or acetyl group can be performed by dissolving a compound in a dilute sodium hydrogen carbonate solution, adding about 1 to 3 equivalent weights of benzoyl chloride or acetic anhydride and allowing to react the mixture at room temperature for about 1 to 16 hours under stirring.

Examples of introducing a protective group into an acidic group are as follows.

1) A compound is reacted with a diazoalkane (e.g., diazomethane) in a solvent (e.g., ethyl ether, tetrahydrofuran, dioxane or methanol) at about 0° C. to reflux temperature for about 2 minutes to 10 hours.

2) A compound is reacted with an activated alkyl halide (e.g., methyl iodide or p-nitrobenzyl bromide). Suitably, the reaction is conducted in a solvent (e.g., dimethylformamide or dimethylacetamide) at about 0° C. to 60° C. for about 2 minutes to 20 hours. The co-existence of a solution of alkali metal salt (e.g., sodium hydroxide or potassium hydroxide), or ammonia or triethylamine with the reaction mixture does not disturb this reaction.

3) A compound is reacted with an alcohol (e.g., methanol) in the presence of a condensing agent such as a mineral acid (e.g., hydrochloric acid sulfuric acid) or p-toluenesulfonic acid. The reaction is carried out at about 0° C. to reflux temperature for about 15 minutes to 20 hours in a solvent such as the corresponding alcohol or a mixed solvent of said alcohol and chloroform, dichloromethane or dixoane.

4) A compound is reacted with an acid anhydride or acid halide such as acetic anhydride, acetyl chloride or di-tert-butyl dicarbonate in an organic solvent such as chloroform or dichloroethane at 0° C. to reflux temperature for 15 minutes to 15 hours. The solvent may contain a basic reaction catalyst such as triethylamine or pyridine.

The following is the explanation of the biological activities of the compounds of this invention.

The affinity for the glutamate receptor in the brain of the compounds (I) and (II) was determined by the following method.

Method

The receptors of the exitatory amino acid (especially, glutamate) are classified into NMDA type, Quisqualate type and Kainate type. 3H-CPP [3-(2-carboxypiperazin-4-yl)propyl-1-phosphoric acid] as the ligand (a radio active substance which has high affinity for the receptor) for the NMDA-type-receptor, $^3$H-AMPA (DL-$\alpha$-amino-3-hydroxy-5-methylisoxazole-4-propionic acid) as the ligand for the quisqualate-type-receptor, and $^3$H-kainic acid as the ligand for the kainate-type-receptor were used respectively. A sample of the crude synaptic membrane prepared from the forebrain of rat was washed 4 times by Tris hydrochloric acid buffer (pH 7.1) and kept in a freezing condition at $-20°$ C. until its use.

Samples of the frozen crude synaptic membrane were melted and, after floating on 50 mM Tris hydrochloric acid buffer (pH 7.1), incubated for 30 minutes at 37° C. After the incubation, the synaptic membrane was centrifuged (48,000$\times$g) and washed 3 times with 50 mM Tris hydrochloric acid buffer and used in the test.

In the binding assay of the NMDA-type-receptor, samples of the synaptic membrane were incubated in the presence or absence of a test compound together with 10 nM $^3$H-CPP in 50 mM Tris hydrochloric acid buffer (pH 7.1, 0° C.) for 15 minutes. The sediment (pellet) containing synapse membrane which was recovered by centrifugation of the incubation solution was rinsed with 50 mM Tris hydrochloric acid buffer (pH 7.1) and dissolved in 0.5 ml of Protosol ® (made by New England Nuclear Inc.). In the binding assay of Quisqualate-type-receptor and Kainate-type-receptor, samples of the synapse was incubated in the presence or absence of a test compound in 5 nM $^3$H-AMPA (Quisqualate-type-receptor) or 2 nM $^3$H-Kainic acid (Kainate-type-receptor) together with 50 mM Tris hydrochloric acid buffer (pH 7.1, 0° C.) for 90 minutes. The solution was filtered with Whatman GF/B filter (Whatman ®, made by Whatman Inc.) under reduced pressure and the filter was washed 3 times with 50 mM Tris hydrochloric acid buffer. The radioactivity on the filter was measured by a conventional method. The specific binding amount was determined by subtracting the non-specific binding from the total binding, taking the binding in the presence of an excessive non-radioactive L-sodium glutamate (1 mM) as the amount of the non-specfic binding, i.e., the binding to anything other than the receptor. The 50% inhibiting concentration (IC$_{50}$) of the compound to be tested was determined as the concentration which inhibits 50% of the specific receptor binding of $^3$H-CPP, $^3$H-AMPA or $^3$H-kainic acid.

Table 5 shows the affinities to the aforesaid 3 sub-type receptors of sodium glutamate (hereinafter sometimes referred to as "Glu-Na") which is a excitatory amino acid, and also to the aforesaid compounds. As shown in the Table 5, Glu-Na has high affinities to 3 sub-type receptors and the IC50 thereof was 0.11 to 0.98 $\mu$M. The following compounds showed high affinities to the 3 sub-type receptors: that is, Compounds 1, 72, 51, 87, 75, 78, 6, 63, 66, 69, 81, 84, 107, 110, 117, 120, 123, 126, 129, 132, 135, 173, 170 and 167. Compounds 149, 155, 158, 104, 176, 180 and 182 had differences in their affinities, depending upon the sub-types of receptors, Compounds 72, 6, 107, 132, 149, 155, 180 and 182 showed a high affinity to the NMCA-type-receptor, the compounds 1, 75, 78, 6, 69, 81, 107, 110, 132, 173 and 158 showed a strong affinity to the Quisqulate-type-receptor, and the compounds 1, 75, 69, 132, 6, 173 and 167 showed a strong affinity to the Kainate-type-receptor.

TABLE 5

| Compound | Affinities to stimulative amino acid receptors (IC$_{50}$: $\mu$M) | | |
|---|---|---|---|
| | NMDA-type receptor ($^3$H-CPP) | Quisqulate-type receptor ($^3$H-AMPA) | Kainate-type receptor ($^3$H-KA) |
| Glu—Na | 0.98 | 0.24 | 0.11 |
| 1 (sodium salt) | 19 | 0.28 | 3.6 |
| 72 (hydrochloride) | 6.2 | 14 | 37 |
| 51 | 10 | 20 | 51 |
| 87 | 11 | 15 | 26 |
| 75 | 11 | 0.31 | 7.3 |
| 78 | 68 | 3.9 | 98 |
| 6 | 6.1 | 3.8 | 7.9 |
| 63 | 47 | 21 | 22 |
| 66 | 21 | 48 | 19 |
| 69 | 11 | 6.4 | 5.2 |
| 81 | 35 | 0.67 | 17 |
| 84 | >100 | 3.8 | 67 |
| 107 | 6.5 | 3.0 | 12 |
| 110 | 16 | 5.5 | 31 |
| 117 | 16 | 13 | 29 |
| 120 | 11 | 21 | 24 |
| 123 | 27 | 59 | 37 |
| 126 | 10 | 17 | 18 |
| 129 | 10 | 13 | 36 |
| 132 | 6.3 | 1.0 | 4.5 |
| 135 | 32 | 19 | 43 |
| 149 | 5.8 | >100 | >100 |
| 155 | 8.3 | >100 | >100 |
| 173 | 13 | 0.12 | 3.8 |
| 158 | >100 | 0.31 | 57 |
| 104 | 47 | >100 | >100 |
| 176 | 21 | >100 | >100 |
| 180 | 7.9 | >100 | >100 |
| 182 | 2.1 | >100 | >100 |
| 170 | 40 | 67 | 20 |
| 167 | 20 | 61 | 6.8 |

Next, it was tested whether or not these compounds have the stimulating activities [activating effect] to the receptors and in other words whether or not these compounds have an excitatory action on neurons of rat hippocampus in vitro.

Method

Male Wister rats (body weight: 300–350 g) were used in the test. After cutting the head of rats, the brain was quickly taken out and 400 $\mu$M thickness of the sliced samples of a hippocampus was prepared by a slice cutter. These samples were incubated in a nutrient solution (Krebs-Ringer solution, 33° C.) saturated with a mixed gas of 95% of oxygen gas and 5% of carbon dioxide gas for one or more hours. The test was carried out in the perfusion cisterna with perfusing at the flow speed of 1.5 ml/min. The action potential (spike) in CA1 pyramidal cell layer of the hippocampus was recorded extracellularlly by using a glass electrode filled with 2M NaCl solution. The test compounds were added to the perfusate and the change in number of the spikes with passage of time was counted by a pulse counter and recorded on the recorder. The Krebs-Ringer's solution contains 124 mM of NaCl, 5 mM of KCl, 1.24 mM of KH$_2$PO$_4$, 1.3 mM of MgSO$_4$, 2.4 mM of CaCL$_2$, 26 mM of NaHSO$_4$ and 10 mM of glucose.

Glu-Na, which is a representative excitatory amino acid, induced excitation of neurons at the concentration of 100 or more μM in the test system as shown in Table 6. On the other hand, the concentrations which induced excitation by the compounds of the present invention were lower, i.e., 300 or more μM for Compounds 1, 72 and 132, 0.3 or more μM for Compounds 173 and 158, 1 or more μM for Compounds 75 and 81, 3 or more μM for Compounds 84, 10 or more μM for Compound 155 and 30 or more μM for Compounds 78, 98, 149 and 180. Thus, the compounds of this invention showed a strong activity compared with that of glutamic acid which is a substance existing in a living body.

TABLE 6

Activating effect on the activity of hippocampus nervous cell of rats
(Minimum effective concentration to induce firing)

| Compound | Minimum effective concentration (μM) |
|---|---|
| Glu—Na | 1000 |
| 1 (sodium salt) | 300 |
| 72 (hydrochloride) | 300 |
| 75 | 1 |
| 78 | 30 |
| 81 | 1 |
| 84 | 3 |
| 173 | 0.3 |
| 158 | 0.3 |
| 87 | 30 |
| 149 | 30 |
| 155 | 10 |
| 180 | 30 |
| 132 | 300 |

The cerebral neuron in Alzheimer's senile dementia is aging, its number is decreasing and its normal function is being altered. The same situation is recognized at the hippocampus which has an important role in forming memory and it is strongly suggested that these compounds of the present invention can improve a memory injury by an activation of the activity of the hippocampal neuron.

The inventors further studied on effects for improving memory dysfunction of these compounds.

Method

Experimental memory disturbance was induced by administering a protein synthesis inhibiting agent, cycloheximide to C57BL/b male mice of 5 week-age. The memory test was carried out using a passive avoidance learning equipment consisting of two chambers of dark and bright. At first, a memory acquisition process of mice was carried out. In this process, a mouse was released in the bright chamber and the guillotine type door connecting between bright and dark chambers was open. Immediately after the mouse that likes a dark place having entered into the dark chamber, said guillotine type door was closed and an electric shock of 0.4 mA was given to the mouse for 3 seconds through the floor grid. Mice learned through this process to receive electric shock from the floor once they move to the dark chamber. However, the memory formation in mice that received cycloheximide (60 mg/Kg) subcutaneously 30 minutes before this memory acquisition process becomes insufficient. The memory retention test was carried out in accordance with similar procedures with mice which received cycloheximide (memory dysfunction group) and normal mice on the next day that the memory acquisition process was carried out. A time from the release of mice in the bright chamber to the entry into the dark chamber through the guillotine type door opened was measured (latency). The latency was shorter in the memory dysfunction group and the effectiveness of the compounds was determined in terms of a degree of the prolongation of latency. The test compounds were intraperitoneally administered twice in total to the mice each 30 minutes before the memory acquisition process and the memory keeping test.

The effect of the compounds in improving a memory dysfunction was expressed as a percentage in which the latency in the memory impairment group at the memory retention test was regarded as 100, and the results are shown in Table 7.

Accordingly, a longer latency shows a greater improvement of the memory impairment and the larger figures in the Table 7. As shown in the Table 7, the compounds 72, 75 and 78 showed an effect to prolong the latency significantly.

Thus, the aforesaid compounds show a high affinity to the excitatory amino acid-receptor of brain activate neurons and particularly the hippocampal neurons through its receptors and possess an activity to accelerate the memory formation.

TABLE 7

Improvement to Memory Dysfunction Induced by Cycloheximide Administration

| Compound | Dosage (mg/kg, i.p.) | Tested Retention Time (percentage to control group) |
|---|---|---|
| 72 (hydro-chloride) | 1 | 217 |
|  | 10 | 278* |
| 75 | 1 | 205 |
|  | 10 | 184* |
| 78 | 1 | 179 |
|  | 10 | 222* |
| Glutamic acid | 10 | 101 |

Number of one group: 20-21 mice
*mean $p < 0.05$ (comparison with control group having memory dysfunction)

Of the compounds represented by the formulae (I) and (II), the acute toxicity in mouse of Compound 1 was more than 4 g/kg in any administration routes (iv, ip, sc, po).

The compounds (I) and (II) and salts thereof activate nervous cells of mammals (e.g., rat, monkey, human being), accelerate a memory, show a low toxicity and accordingly are useful as cerebral function improving agents. In other words, they are useful therapeutic agents not only for cerebral apoplexy, Alzheimer's disease but also for memory injuries (decrease of mental function) caused by an external injury at head or hydrocephalus.

The cerebral function ameliorator of the present invention comprises usually a compound of the present invention or salt thereof and a pharmaceutically acceptable carrier. The active component can be used in any form of tablets, pellets, capsules, suppositories, emulsions, suspensions and any other forms appropriate as medicines. In case of preparing orally active therapeutic drugs thereof, a binding agent (e.g., hydroxypropylcellulose, hydroxypropylmethylcellulose, macrogol, etc.), a collapsing agent (e.g., starch, carboxymethylcellulose calcium, etc.), an excipient (e.g., lactose, starch, etc.) and a lubricant (e.g., magnesium stearate, talc, etc.) and the like can be used at the respective appropriate amount.

In case of preparing injections, an isotonizing agent (e.g., glucose, D-sorbitol, D-mannitol, sodium chloride, etc.), a preservative (e.g., benzyl alcohol chlorobutanol, methyl p-hydroxybenzoate, propyl p-hydroxybenzoate, etc.) and a buffer (e.g., phosphoric acid buffer, sodium acetate buffer, etc.) and the like can be used.

The following are administration methods of the compound of the present invention or salt thereof.

The compound of the present invention or salt thereof can be parenterally (i.e., subcutaneously, intravenously or intramuscularly) administered to the above mentioned animal at an amount of about 0.01-20 mg/Kg/day, preferably about 0.1-5 mg/Kg/day. Also, it can be orally administered at an amount of about 0.02-100 mg/Kg/day, preferably about 0.1-20 mg/Kg/day.

The present invention is further explained in more detail by examples and composition examples but not limited to them. The percentage in the medium components shows weight/volume % unless otherwise specifically indicated, and the conditions of HPLC is the examples are the same as those mentioned before.

EXAMPLE 1

A medium (500 ml, adjusted to pH 7) containing 2.0% of glucose, 3% of soluble starch, 1.0% of corn steep liquor, 1.0% of defatted soybean powder, 0.5% of peptone, 0.3% of sodium chloride and 0.5% of calcium carbonate was poured into 3 l of Sakaguchi's flask and sterilized. A loopful of a slant culture of *Streptomyces platensis* A-136 (IFO 14603, FERM BP-1786) was inoculated to this medium and cultured on a reciprocating shaker (120 rev./minute) at 28° C. for 48 hours. The resultant cultured broth (500 ml) was inoculated to the medium (30 l) containing 0.05% of an antifoaming agent (Actocol made by Takeda Chemical Industries, Japan) and the same components with the aforesaid medium in a 50 l stainless tank which had been sterilized in advance, and cultured at 28° C. for 48 hours with agitation of 280 rpm and aeration of 30 l/minute. The resultant cultured broth (6 l) was inoculated to a medium (120 l and pH 7.0) containing 0.5% of glucose, 5% of dextrin, 3.5% of defatted soybean powder and 0.7% of calcium carbonate in a stainless tank (200 l) which had been sterilized in advance, and cultured at 28° C. for 90 hours with agitation of 200 rpm and aeration of 120 l/minute.

EXAMPLE 2

The cultured broth (100 l) obtained in Example 1 was adjusted to pH 8.0 and Hyflo Super Cel (made by Johns Manville, Co., U.S.A.) was added thereto and filtered. Ethyl acetate (40 l) was added to the filtrate (85 l) adjusted to pH 3 and the ethyl acetate layer was, after stirring, removed therefrom. The resultant aqueous layer was concentrated, and the concentrate (50 l) adjusted to pH 5 was applied to a column chromatography of Amberlite IR-120 (H+type, 8 l). An antibiotic was eluted with 2% of an aqueous ammonium and this eluate (40 l) was concentrated. The concentrate (18 l) was applied to a column chromatography of Diaion HP-20 (8 l), which was washed with water (12 l). The concentrate (3.3 l) of the effluent was applied to a column chromatography of Diaion SP-207 (2 l) eluting with water. The fractions (4 l) containing an antibiotic were gathered and applied to a column chromatography of QAE-Sephadex A-25 CL−type, 2.5 l) developing with 0.02-0.04 M of a saline solution. The active fractions (5 l) were gathered and concentrated. The concentrated solution (0.4 l) was applied to a column chromatography of a crystalline cellulose (made by Asahi Chemical, Japan), developing with a mixed solvent of acetonitrile and water (9:1-4:1). The fractions which showed a single peak on a HPLC were combined and concentrated to obtain 2.59 g of Compound 1 (monosodium salt) as white powders.

The fractions showing an antifringal activity were gathered from those other than the fractions which showed a single peak in a chromatography of QAE-Sephadex, and applied to a chromatography of Amberlite IR-120 (H+type, 0.8 l), eluting with 2% aqueous ammonia. The eluate was concentrated and lyophilized to obtain 4.1 g of Compound 6 containing TAN-950A, B, C, D and E as white powders.

EXAMPLE 3

Each (40 ml) of a medium (pH 7) containing 2.0% of glucose, 3.0% of soluble starch, 1.0% of corn steep liquor, 1.0% of defatted soybean powder, 0.5% of peptone, 0.3% of sodium chloride and 0.5% of calcium carbonate was poured into ten 200 ml Erlenmeyer's flask and, after sterilization, a loopful of slant culture of *Streptomyces hydgroscopicus* A-300 (FREM No. 1312) was inoculated thereto, and the medium was cultured for 48 hours at 28° C. on a rotary shaker (200 rev./minute). This was collected together and used as a seed culture broth.

Each (40 ml) of a medium (pH 7.0 and 5 l) containing 0.5% of glycerine, 3.5% of defatted cotton seed powder (Profuro, made by Traders Oil Mill Co., U.S.A.) and 0.7% of sedimentative calcium carbonate was poured into a 200 ml Erlenmeyer's flask and sterilized. After cooling, 2 ml per each flask of the aforesaid seed culture broth was inoculated and cultured on a rotary shaker (200 rev./minute) at 28° C. for 5 days. The cultured broth was filtered to obtain the filtrate (4.3 l). After having adjusted to pH 3, ethyl acetate (2 l) was added to the filtrate, followed by agitation for 30 minutes. After filtration, the separated aqueous layer was washed with ethyl acetate (1.5 l) and the aqueous layer filtrate (4.2 l) was obtained. This filtrate was applied to a column chromatography of Amberlite IR-120 (H+type, 1 l), eluting with 2% aqueous ammonia. The eluate (5 l) was concentrated and applied to a column chromatography of Diaion SP-207 (0.3 l), eluting with water. The fractions (350 ml) showing an antibacterial activity were applied to a column chromatography of QAE-Sephadex (Cl−type, 100 ml), developing with 0.02-0.03M of a saline solution. The active fractions (100 ml) were applied to a column chromatography of a crystalline cellulose (70 ml), eluting with a mixed solvent of acetonitrile (85-70) and water (15-30), to gather the fractions containing antibiotic. Then, the fractions containing only Compound 1 were gathered by an analytical HPLC, concentrated and lyophilized. The powder obtained (180 mg) was physicochemically identical with the standard sample of Compound 1 (sodium salt).

*Streptomyces hygroscopicus* subsp. hydroscopicus (IFO 14012) was cultured for 4 days under the same conditions as those aforementioned. The cultured broth (2.8 l) was purified in the same manner as the aforementioned one to obtain 302 mg of Compound 1 (sodium salt).

EXAMPLE 4

59 l of the cultured broth (105 l) obtained in accordance with the method of Example 1 was filtered using Hyflo Super Cel. The filtrate (7.6 l) was passed through a column of Diaion SP-207 (2 l). 3.6 l of the effluent (8.1 l) were applied to a column chromatography of Amberlite IR-120 (H+type, 700 ml), eluting with 1.2 l of 2% of aqueous ammonia. The eluate (pH 10) was applied to a column chromatography of Amberlite IR-402 (Cl−type, 100 ml), developing with 1.3 l of 0.2M saline solution. The active fractions were concentrated and dioxane (150 ml) was added to the concentrate (150 ml, which contains 2.84 g of the Compound 1 according to HPLC analysis) and then the solution was adjusted to pH 9.3 by addition of triethylamine. BOC-ON (4.5 g, 1.8 equivalent) was added to this solution and stirred for 3 hours at room temperature. The reaction mixture was concentrated, dried and dissolved in water (100 ml). The obtained aqueous solution was washed with ethyl acetate (100 ml×3). The aqueous layer, after adding sodium chloride, was adjusted to pH 2.7 and extracted with ethyl acetate (100 ml×3). The extract was concentrated. A mixture of ether and hexane was added to the extract to obtain 2.8 g of Compound 9 as powders. The purity of these powders was 65% according to an analysis by HPLC (the standard sample obtained in Example 8 was regarded as 100%).

EXAMPLE 5

Compound 6 (240 mg) was dissolved in 0.3 N sodium hydroxide aqueous solution (12 ml) and stirred for 1 hour at 60° C. The reaction mixture was adjusted to pH 6.7, concentrated and applied to a column chromatography of a fine crystalline cellulose (200 ml), developing with a mixed solvent of acetonitrile and water (9:1–7:3). The fractions showing a single peak on HPLC were gathered, concentrated and lyophilized to obtain 134 mg of Compound 1 (monosodium salt) as white powders.

EXAMPLE 6

Compound 1 (monosodium salt, 517 mg) was dissolved in 2% sodium hydrogen carbonate aqueous solution (30 ml), to which benzoyl chloride (350 μl) was added and stirred for one hour at room temperature, followed by addition of benzoyl chloride (300 μl) and stirring at room temperature at pH 8.0–8.5. The reaction mixture was washed with ethyl acetate, adjusted to pH 3.0 with 2N hydrochloric acid and washed with ether. After addition of sodium chloride, the aqueous solution layer was extracted with ethyl acetate (50 ml). The organic layer was dehydrated over sodium sulfate and concentrated to dryness. The residue was treated with ether to obtain 460 mg of Compound 7 as white powders. The powder (100 mg) was crystallized from a mixed solvent of methanol and ethyl ether to afford 70 mg of Compound 7 as crystals.

Melting point: 147–148.5° C. (decom.)

Specific rotation $[\alpha]_D^{22}$: −28.1° (c=0.50, in methanol)

UV: $\lambda_{max}^{MeOH}$ ($E_{1cm}^{1\%}$) 226 nm (515), 257 nm (410)

IR(KBr): 3080, 1745, 1650, 1580, 1540 (cm$^{-1}$) $^1$H-NMR(DMSO-d$_6$): 12.66(1H,br.). 8.71(1H,d,J=7.8Hz), 8.32(1H,s), 7.85(2H,m), 7.50(3H,m), 4.52(1H,ddd,J=5.2, 7.8, 9.3Hz), 2.76(1H,dd,J=5.2, 14.8Hz), 2.67(1H,dd,J=9.3, 14.8Hz)

FD-MS m/z 277(M+H)+

Elemental analysis (C$_{13}$H$_{12}$N$_2$O$_5$) calculated: C, 56.52; H, 4.38; N, 10.14; found: C, 56.50; H, 4.47; N, 10.02.

$^{13}$C NMR (DMSO-d$_6$): 172.66(s), 171.71(s), 166.25(s), 151.94(d), 133.77(s), 131.33(d), 128.20(d), 127.22(d), 93.36(s), 52.21(d), 23.64(t)

EXAMPLE 7

Compound 1 (monosodium salt, 500 mg) was dissolved in 2% sodium hydrogen carbonate aqueous solution (50 ml), to which acetic anhydride (270 μl) was added, and then stirred for 30 minutes at room temperature. To the mixture were added sodium hydrogen carbonate (200 mg) and acetic anhydride (100 μl). The solution was stirred for 30 minutes at room temperature, and concentrated. The residue was subjected to a column chromatography of Bio Gel P-2 (made by Bio Rad Co., U.S.A., 100–200 mesh, 500 ml), eluting with water. The active fractions were concentrated and lyophilized to obtain a crude powder (570 mg). The crude powder was subjected to a column chromatography of a fine crystalline cellulose (200 ml) developing with a mixed solvent of acetonitrile:water (85:15–70:30). The fractions showing a single peak on HPLC were gathered, concentrated and lyophilized to obtain 245 mg of Compound 8 as white powders.

UV: $\lambda_{max}^{H2O}$ ($E_{1cm}^{1\%}$) 254 nm(304),

IR(KBr): 3440, 1640, 1520 cm$^{-1}$ $^1$H-NMR(D$_2$O): 7.98(1H,s), 4.26(1H,dd,J=4.6, 8.3Hz), 2.68(1H,dd,J=4.6, 15.0Hz), 2.51(1H,dd,J=8.3, 15.0Hz), 2.01(3H,s)

Elemental analysis (C$_8$H$_8$N$_2$O$_5$Na$_2$·1.5H$_2$O) calculated: C, 33.70; H, 3.89; N, 9.82; Na, 16.12; found: C, 33.99; H, 3.63; N, 9.91; Na, 16.00

EXAMPLE 8

Compound 1 (monosodium salt, 6.36 g) was dissolved in 50% dioxane aqueous solution (150 ml), to which triethylamine (6.3 ml) and 2-(t-butoxycarbonyloxyimido)-2phenylacetonitrile (BOC-ON, 11.4 g) were added. The mixture was stirred for 3 hours at room temperature and concentrated up to 50 ml. Water (300 ml) was added to the concentrated solution, which was washed three times with ethyl acetate (150 ml). The aqueous layer was adjusted to pH 2.7, treated with sodium chloride and then extracted three times with ethyl acetate (150 ml). The organic layer obtained was washed with a saturated saline solution, dried over sodium sulfate and concentrated to dryness. The residue was treated with a mixed solvent of n-hexane and ether to obtain 6.32 g of Compound 9 as white powders.

Specific rotation $[\alpha]_D^{19}$ D-29.3° (c =0.54 in methanol)

UV: $\lambda_{max}^{MeOH}$ $E_{1cm}^{1\%}$ 260 nm (337),

IR(KBr): 3110, 2990, 1675, 1580, 1510 cm$^{-1}$ $^1$H-NMR(DMSO-d$_6$): 12.50(1H,br.), 8.23(1H,s), 7.06(1H,d,J=8.2Hz), 4.02(1H,ddd,J=5.1, 8.2, 9.4Hz), 2.57(1H,dd,J=5.1, 14.6Hz), 2.43(1H,dd,J=9.4, 14.6Hz), 1.36(9H,s)

SI-MS m/z 273(M+H)+

Elemental analysis (C$_{11}$H$_{16}$N$_2$O$_6$) calculated: C, 48.53; H, 5.92; N, 10.29; found: C, 48.51; H, 6.05; N, 10.23

EXAMPLE 9

A solution of Compound 9 (148 mg) in trifluoroacetic acid (1 ml) was kept at room temperature for 20 minutes, concentrated and dried. The residue was treated with ethyl ether to afford a crude powder (136 mg). The crude powder was dissolved in water (2 ml). The solution was adjusted to pH 7.0 by addition of sodium hydrogen carbonate and subjected to a column chromatography of a fine crystalline cellulose (100 ml) developing with a mixed solvent of acetonitrile:water (85:15–80:20). The active fractions were concentrated and subjected to a column chromatography of Sephadex LH-20 (500 ml) eluting with 20% aqueous methanol. The fractions showing a single peak on HPLC were gathered, concentrated and lyophilized to obtain 56 mg of Compound 1 (monosodium salt) as white powders.

EXAMPLE 10.

To a solution of Compound 9 (1.0 g) in dimethylformamide (10 ml) were added sodium carbonate (214 mg) and methyl iodide (0.69 ml). The mixture was stirred for 2 hours at room temperature and concentrated. 0.05M phosphoric acid buffer (pH 7.0, 100 ml) was added to the residue and adjusted to pH 8.0 by addition of sodium hydrogen carbonate. The aqueous solution was washed twice with ethyl acetate (50 ml), adjusted to pH 2.8 and extracted three times with ethyl acetate (50 ml). The organic layer obtained was washed with a saturated saline solution, dried over sodium sulfate and concentrated to dryness, to obtain 996 mg of N'-methyl form of Compound 2 as colorless oil.

The compound (996 mg) was dissolved in trifluoroacetic acid (3 ml) and kept for 30 minutes at room temperature. The reaction mixture was concentrated to dryness. The residue was treated with a mixed solution of n-hexane and ether, to obtain a crude powder (982 mg). The crude powder was dissolved in water (6 ml), which was adjusted to pH 6.9 by addition of sodium hydrogen carbonate and subjected to a column chromatography of a fine crystalline cellulose (400 ml), developing with a mixed solvent of acetonitrile and water (85:15–80:20). The active fractions were concentrated and again subjected to a column chromatography of Bio-Gel P-2 (100–200 mesh, 500 ml), developing with water. The fractions showing a single peak on HPLC were gathered, concentrated and lyophilized to obtain 367 mg of Compound 10 as white powders.

Specific rotation $[\alpha]_D^{23}$: $-42.8°$ (c=0.58, in water)
UV: $\lambda_{max}^{H2O}$ ($E_{1cm}^{1\%}$) 269 nm (553)
IR(KBr): 3430, 3050, 1720, 1630, 1600, 1495 cm$^{-1}$
$^1$H-NMR(D$_2$O ): 8.13(1H,s), 3.92(1H,t,J=5.8Hz), 3.58(3H,s), 2.83(2H,d,J=5.8Hz)
SI-MS m/z 187(M+H)$^+$
Elemental analysis (C$_7$H$_{10}$N$_2$O$_4$·0.5H$_2$O) calculated: C, 43.08; H, 5.68; N, 14.35; found: C, 42.50; H, 5.79; N, 13.88

EXAMPLE 11

Compound 9 (800 mg) was dissolved in pyridine (4 ml), to which acetic anhydride (2 ml) was added and kept for 20 minutes at room temperature. After the addition of 0.5N hydrochloric acid (80 ml), the reaction mixture was adjusted to pH 2.3 and extracted with ethyl acetate (100 ml). The organic layer was washed with a saturated saline solution, dried and concentrated to dryness to obtain 875 mg of Compound 11 as white powders.

UV: $\lambda_{max}^{MeOH}$ ($E_{1cm}^{1\%}$) 284 nm (570)
IR(KBr): 3370, 1770, 1735, 1685, 1615, 1520 cm$^{-1}$
$^1$H-NMR(DMSO-d$_6$): 12.70(1H,br.), 8.74(1H,s), 7.14(1H,d,J=7.0Hz), 4.13(1H,m), 2.50–2.74(2H,m), 2.35(3H,s), 1.36(9H,s)
Elemental analysis (C$_{13}$H$_{18}$N$_2$O$_7$) calculated: C, 49.68; H, 5.77; N, 8.91; found: C, 49.41; H, 5.70; N, 8.65

EXAMPLE 12

To a solution of Compound 11 (157 mg) in methanol (3 ml) was added 0.5N sodium hydroxide aqueous solution (3 ml). The solution was kept for 30 minutes at room temperature, adjusted to pH 6.4 with 1N hydrochloric acid and concentrated. A saturated saline solution was added to the residue, and the solution was adjusted to pH 2.5 with 1N hydrochloric acid and extracted with ethyl acetate. The organic layer was washed with a saturated saline solution, dried over sodium sulfate and concentrated to dryness. The residue was treated with a mixed solvent of n-hexane and ether to obtain a white powder (113 mg) of Compound 9.

EXAMPLE 13

A suspension of Compound 1 (mono-sodium salt, 3.0 g, purity 92%) in a mixed solvent (50 ml) of hydrochloric acid and methanol was kept for 20 hours at room temperature and filtered. The filtrate was concentrated and a saturated aqueous solution was adjusted to pH 6.2, concentrated and subjected to a column chromatography of a fine crystalline cellulose (500 ml), developing with a mixed solvent of acetonitrile and water (90:10–85:15). The active fractions were gathered and concentrated up to 10 ml. The concentrate was subjected to a column chromatography of a fine crystalline cellulose, developing with a mixed solvent of acetonitrile and water (9:1). The fractions showing a single peak on HPLC were gathered, concentrated and lyophilized to obtain 722 mg of Compound 12 as white powders.

UV: $\lambda_{max}^{H2O}$ ($E_{1cm}^{1\%}$) 252 nm (410)
IR (KBr): 3420, 2970, 1750, 1630, 1500 cm$^{-1}$
$^1$H-NMR(D$_2$O): 7.97(1H,s), 4.27(1H,t,J=5.7Hz), 3.84(3H,s), 2.85(2H,d,J=5.7Hz)
SI-MS m/z 187(M+H)$^+$
Elemental analysis (C$_7$H$_{10}$N$_2$O$_4$·0.5H$_2$O) calculated: C, 43.08; H, 5.68; N, 14.35; found: C, 42.91; H, 5.20; N, 14.15

EXAMPLE 14

Compound 7 (270 mg) was dissolved in methanol (10 ml), to which an ether solution of diazomethane was added until the reaction solution gained a yellow color. The reaction mixture was concentrated to dryness and applied to a column chromatography of silica gel (15 g) developing with a mixed solvent of n-hexane and ethyl acetate (1:1). The active fractions were gathered and concentrated, to obtain a white powder (138 mg) of Compound 13. The column was further developed with a mixed solvent of n-hexane and ethyl acetate (1:4) and the active fractions were gathered, concentrated, and 142 mg of Compound 14 as colorless oil was obtained.

Compound 13:
Specific rotation $[\alpha]_D^{19}$: $-38.5°$ (c=0.49, in methanol)
UV:$\lambda_{max}^{MeOH}$ ($E_{1cm}^{1\%}$)227 nm (577)
IR (KBr): 3340, 1760, 1640, 1515 cm$^{-1}$
$^1$H-NMR(CDCl$_3$): 7.92(1H,s), 7.75–7.80(2H,m), 7.40–7.54(3H,m), 6.77(1H,d,J=6.7Hz), 4.93(1H,ddd,J=4.9, 5.3, 6.7Hz), 4.01(3H,s), 3.79(3H,s), 3.04(1H,dd,J=5.3, 15.0Hz), 2.87(1H,dd,J=4.9, 15.0Hz)

SI-MS m/z 305(M+H)+

Elemental analysis ($C_{15}H_{16}N_2O_5$) calculated: C, 59.21; H, 5.30; N, 9.21; found: C, 59.16; H, 5.32; N, 9.16

Compound 14:

Specific rotation $[\alpha]_D^{19}$ −26.5° (c=0.54, in methanol)

UV: $\lambda_{max}^{MeOH}$ ($E_{1cm}^{1\%}$) 226 nm (400), 270 nm (369)

IR (KBr): 3350, 1740, 1665, 1605, 1535 cm$^{-1}$ $^1$H-NMR(CDCl$_3$): 7.88–7.93(2H,m), 7.83(1H,d,J=7.2Hz), 7.63(1H,s), 7.41–7.55(3H,m), 4.90(1H,dt,J=7.2, 5.6Hz), 3.75(3H,s), 3.37(3H,s), 2.91(2H,d,J=5.6Hz)

SI-MS m/z 305(M+H)+

Elemental analysis ($C_{15}H_{16}N_2O_5$) calculated: C, 59.21; H, 5.30; N, 9.21; found: C, 59.59; H, 5.22; N, 8.77

EXAMPLE 15

Compound 6 (4.8 g) was dissolved in dimethylformamide (50 ml), to which p-nitrobenzylbromide (5.0 g) was added and stirred for 1.5 hours at room temperature. Then, p-nitrobenzylbromide (5.0 g) was added to the mixture and stirred for 6 hours at room temperature. The reaction mixture was concentrated, added with a saturated saline solution and then extracted with ethyl acetate. The organic layer was washed with a saturated saline solution, dried over sodium sulfate and concentrated to dryness. The residue was treated with n-hexane to obtain a crude powder (10.2 g). The crude powder was applied to a column chromatography of a silica gel (250 g), washing with a mixed solvent of n-hexane and ethyl acetate (25:75) and then eluting with a mixed solvent of n-hexane and ethyl acetate (20:80–0:100). The active fractions were gathered and concentrated to obtain a crude powder (690 mg) of Compound 15 and a crude powder (2.4 g) of p-nitrobenzyl ester forms of Compounds 2–5. Both of them were purified respectively by a column chromatography of a silica gel (a mixed solvent of chloroform and ethyl acetate), to afford a powder (390 mg) of Compound 15, a powder (Compound 16, 155 mg) of p-nitrobenzyl ester form of any one of Compounds 2–5, a mixture (880 mg) containing 3 isomers of Compound 16 and a mixture (220 mg) containing Compound 16 and 3 isomers of Compound 16.

Compound 15

IR (KBr): 3450, 3090, 2930, 2860, 1740, 1605, 1515 cm$^{-1}$ $^1$H-NMR(DMSO-d$_6$): 8.50($^1$H,s), 8.22, 8.18, 8.15 (each 2H,d,J=8.6Hz), 7.63, 7.60, 7.56 (each 2H,d,J=8.6Hz), 5.24(2H,ABq,J=14.0Hz), 4.99(2H,s), 3.93(1H,br.d,J=15.0Hz), 3.78(1H,br.d.J=15.0Hz), 3.51(1H,m), 2.94(1H,br.), 2.54(2H,m)

Elemental analysis ($C_{27}H_{23}N_5O_{10}$) calculated: C, 56.15; H, 4.01; N, 12.13; found: C, 56.18; H, 3.91; N, 12.03

Compound 16

Specific rotation $[\alpha]_D^{19}$ +44 9° (c=0.52, in methanol)

IR (KBr): 3250, 1755, 1705, 1610, 1520 cm$^-$ $^1$H-NMR(DMSO-d$_6$): 10.83(1H,s), 8.38(1H,br.) 8.25(2H,d,J=8.6Hz), 7.68(2H,d,J=8.6Hz), 7.29(1H,d,J=6.2Hz), 5.32(2H,s), 4.32(1H,d,J=8.3Hz), 3.24(1H,dt,J=6.2, 9.2Hz), 2.52(1H,m), 2.34(1H,m)

SI-MS m/z 308(M+H)+

Elemental analysis ($C_{13}H_{13}N_3O_6$) calculated: C, 50.82; H, 4.26; N, 13.68; found: C, 50.82; H, 3.98; N, 13.62

3 Isomers of Compound 16

Specific rotation $[\alpha]_D^{19}$ +19.1° (c=0.47, in methanol)

IR (KBr): 3230, 1755, 1715, 1610, 1520 cm$^{-1}$ $^1$H-NMR(DMSO-d$_6$): 11.11(0.5H,s), 11.80(0.5H,s), 8.37(1H,br), 8.25(2H,d,J=8.5Hz), 7.67(2H,d,J=8.5Hz), 7.26(0.5H,d,J=6.2Hz), 6.70(0.2H,d,J=6.2Hz), 6.67(0.3H,d,J=6.2Hz), 5.32(2H,s), 4.35(1H,m), 3.73(0.5H,m), 3.30(0.5H,m), 2.82–1.84(2H,m)

Elemental analysis ($C_{13}H_{13}N_3O_6$) calculated: C, 50.82; H, 4.26; N, 13.68; found: C, 50.99; H, 4.12; N, 13.69

EXAMPLE 16

1.6M n-butyllithium hexane solution (7.2 ml) was added to an anhydrous tetrahydrofuran solution (20 ml) of diisopropylamine (1.99 ml) at −78° C. under an argon atmosphere and stirred at 0° C. for 10 minutes. The solution was cooled again to −78° C. and dropped through a stainless tube to an anhydrous tetrahydrofuran solution (25 ml) of N-BOC dimethyl L-glutamate (1.32 g) which had been cooled at the same temperature in advance. Ethyl formate (0.84 ml) was added thereto and the temperature of the reaction mixture was returned up to 0° C. in an hour. The mixture was stirred for an hour at 0° C., and ethanol (5 ml) and then ether (40 ml) were added thereto, respectively. The solution was poured into a mixture of 2N hydrochloric acid (12 ml) and a saturated aqueous ammonium chloride (30 ml). The ether layer was extracted with 1% sodium carbonate aqueous solution (80 ml). The extract was washed twice with a mixed solvent (50 ml) of ethyl acetate and hexane (1:1), adjusted to pH 2.5–3 and extracted with ethyl acetate. The ethyl acetate layer was washed twice with water 9100 ml) and also with a saturated saline solution (80 ml), dried over anhydrous sodium sulfate, concentrated under reduced pressure, and a white powder (0.53 g) of Compound 17 was obtained. The powder was crystallized from a mixed solution of ether and hexane.

Compound 17:

melting point: 106–108.5° C.

IR (KBr): 3290, 3000, 1780, 1760, 1700, 1670, 1440, 1370, 1300, 1260, 1210, 1150, 1030, 960, 850, 800 780 cm$^{-1}$ $^1$H-NMR(CDCl$_3$)δ ppm: 9.90(s), 9.79(s), 6.99(br.s), 4.65(dd,J=10.5, 3.6Hz), 4.61(dd,J=10, 6.2H), 3.80(s), 3.78(s), 3.75(s), 3.58(dd,J=10, 4Hz), 2.99(ddd,J=15.5, 10.5, 2.2Hz), 2.72(dt,J=14, 9.5Hz), 2.62(ddd,J=14, 3.7, 3.2Hz), 2.59(ddd,J=15.5, 3.6, 1.8Hz), 2.40(dt,J=14, 9.5Hz), 2.11(ddd,J=14, 9.4, 2.5Hz), 1.51(s), 1.51(s), 1.50(s)

Elemental analysis ($C_{12}H_{17}NO_6$) calculated: C, 53.13; H, 6.32; N, 5.16; found: C, 53.18; H, 6.26; N, 5.06

EXAMPLE 17

1M Lithium trimethylsilylamide hexane solution (0.55 ml) was added to an anhydrous tetrahydrofuran solution (3.0 ml) of dimethyl N-Boc L-glutamate (112 mg) at −78° C. under an argon atmospheres, and stirred for 20 minutes at −40° C. and then cooled again at −78° C. After adding isobutyl formate (69 μl), the reaction mixture was returned to −40° C. in an hour and stirred for 3 hours and i-propanol (0.5 ml) was added thereto. The reaction mixture was diluted with ethyl ether (10 ml) and poured into a mixed solution of 1N hydrochloric acid (0.5 ml) and water (10 ml), to which a saturated aqueous solution (2.5 ml) of sodium hydrocarbonate was added thereto. The ether layer was removed. The aqueous solution was washed twice with ethyl ether (10 ml), adjusted to pH 2.8 with 2N hydrochloric acid and saturated with sodium chloride. The solution was extracted three times with ethyl acetate (10 ml) and the extracts were washed together twice with a saturated saline solution, dried with anhydrous sodium sulfate, concentrated under reduced pressure to obtain 57 mg of Compound 17 as white powders.

Compound 17

SIMS (measured in a mixed solvent of methanol and diethanolamine)

M+H+DEA=377 (DEA: diethanolamine, molecular weight 105)

M+K=310

EXAMPLE 18

Hydroxylamine hydrochloride (107 mg) was added to 10% water-dioxane solution (10 ml) of Compound 17 (378 mg) and stirred for an hour at room temperature. The reaction mixture was diluted with ethyl acetate (50 ml), washed three times with water (25 ml) and then with a saturated saline solution (20 ml), dehydrated with anhydrous sodium sulfate and concentrated under reduced pressure to obtain Compound 18 (360 mg).

Compound 18:

Elemental analysis ($C_{12}H_{18}N_2O_6$) calculated: C, 50.35; H, 6.34; N, 9.79; found: C, 50.68; H, 6.46; N, 9.24

SIMS (measured in a mixed solvent of methanol and dimethanolamine)

M+H+DEA=392 (DEA: diethanolamine, molecular weight 105)

M+K=325

A solution of the resulting Compound 18 (76 mg) in methanol (2.5 ml) to which 2N sodium hydroxide (0.10 ml) was added, was stirred for 2 hours at room temperature. The reaction solution was diluted with ether (10 ml) and poured into water (10 ml). The aqueous layer was washed with diethyl ether (10 ml), adjusted to pH 3 with 1N-hydrochloric acid and extracted twice with ethyl acetate 10 ml). The extracts were washed twice with a 50% saturated saline solution (10 ml) and then with a saturated saline solution (10 ml), dried with anhydrous sodium sulfate and concentrated under reduced pressure to obtain a white powder (57 mg) of Compound 19.

Elemental analysis ($C_{12}H_{18}N_2O_6$) calculated: C, 50.35; H, 6.34; N, 9.79; found: C, 50.11; H, 6.42; N, 8.96

$^1$H-NMR(300 MHz, $CDCl_3$)$\delta$ ppm: 1.43(9H,s), 2.71(1H,dd,J=14.5, 6.2Hz), 2.80(1H,dd,J=14.5, 5.3Hz), 3.76(3H,s), 4.43(1H,m), 5.62(1H,m), 7.94(1H,br.s)

IR (KBr): 3350, 3100, 2990, 1710, 1600, 1520, 1440, 1400, 1370, 1260, 1220, 1160, 1050, 1025, 860, 760, 640 cm$^{-1}$

UV$\lambda_{max}^{MeOH}$ ($E_{1cm}^{1\%}$) 260 nm (260)

$[\alpha]_D^{20}$ −19.2° (c=0.50, MeOH)

EXAMPLE 19

2N Sodium hydroxide aqueous solution (0.5 ml) was added to a methanol solution (1.5 ml) of Compound 19 (57 mg) and stirred for 2 hours at room temperature. The reaction solution was diluted with water (10 ml), washed twice with ether (10 ml), adjusted to pH 2.5 and extracted three times with ethyl acetate (10 ml). The extracts were washed twice with 50% saturated saline solution (10 ml), then with a saturated saline solution (10 ml), dehydrated with anhydrous sodium sulfate and concentrated under reduced pressure to obtain a white powder (46 mg) of Compound 9.

EXAMPLE 20

To a suspension of Compound 9 (136 mg) in chloroform (5 ml) were added triethylamine (146 μl), di-t-butyl dicarbonate (120 μl) and 4-dimethylaminopyridine (1.5 g), followed by stirring for an hour at room temperature. The reaction mixture was adjusted to pH 2.5 with water and extracted with chloroform. The extract was washed with a saturated saline solution, dehydrated with mirabilite and concentrated to dryness, to afford a white powder (183 mg) of Compound 20.

UV: $\lambda_{max}^{MeOH}$ ($E_{1cm}^{15}$) 273 nm (455)

IR (KBr): 3380, 3120, 2990, 1745, 1620, 1515 cm$^{-1}$ $^1$H-NMR($CDCl_3$)$\delta$ ppm: 8.20(1H,s), 5.58(1H,d,J=6.0Hz), 4.60(1H,br.), 4.48(1H,m), 2.93(1H,dd,J=5.0, 14.9Hz), 2.30(1H,m), 1.58(9H,s), 1.44(9H,s)

Elemental analysis ($C_{16}H_{24}N_2O_8$) calculated: C, 51.61; H, 6.50; N, 7.52; found: C, 51.71; H, 6.50, N, 7.70

EXAMPLE 21

A solution of Compound 20 (15 mg) in trifluoroacetic acid (100 μl) was kept for 15 minutes at room temperature. The reaction mixture was concentrated to dryness. 0.1M Phosphoric acid buffer (pH 7.0, 8.5 ml) was added to the residue and the Compound 1 (7.8 mg) was detected by HPLC analysis.

EXAMPLE 22

A suspension of Compound 20 (16 mg) in 1% sodium hydrogen carbonate aqueous solution (3 ml) was stirred for 30 minutes at room temperature. The Compound 9 (10.6 mg) was detected from the solution by HPLC analysis.

EXAMPLE 23

Compound 9 (1 g) was dissolved in a solution (4N: 20 ml) of hydrogen chloride and dioxane, and stirred for an hour at room temperature. The mixture was evaporated under reduced pressure to remove the solvent. Ethyl ether (50 ml) was added to the residue, by which a colorless powder (0.77 g) of Compound 1 (hydrochloride) was obtained.

$^1$H-NMR($D_2O$)$\delta$ ppm: 2.93(2H,d,J=5.8Hz), 4.24(1H,t,J=5.8Hz), 8.34(1H,s)

EXAMPLE 24

A solution of Compound 9 (1 g) in a solution (5.2N: 20 ml) of hydrogen chloride and methanol, was kept for 24 hours at room temperature. The mixture was evaporated under reduced pressure to remove the solvent. Ethyl ether was added to the oily residue, by which a pale yellow powder (0.82 g) of hydrochloride of Compound 12 was obtained.

$^1$H-NMR($D_2O$)$\delta$ ppm: 2.99(2H,d,J=6Hz), 3.85(3H,s), 4.37(1H,t,J=6Hz), 8.39(1H,s)

EXAMPLE 25

Compound 1 (hydrochloride, 0.5 g) was dissolved in methanol (10 ml), to which formalin (37%, 0.5 ml) and sodium cyanoborohydride (0.5 g) were added. The solution was stirred for 10 minutes at 0° C. and then for an hour at room temperature, and evaporated under reduced pressure. Water (10 ml) was added to the residue, which was adjusted to pH 3.0 with 1N hydrochloric acid, agitated for 15 minutes and neutralized to pH 7.0 with an aqueous sodium bicarbonate solution. The mixture was extracted with ethyl acetate (5 ml). The aqueous layer was subjected to a column (2.5×40 cm) chromatography of Amberlite XAD-2 (made by Rohm & Haas Co., U.S.A.). The column was eluted with water and the eluate was lyophilized. Methanol (10 ml) was added to the residue, which was filtered to remove an insoluble substance. The filtrate was evaporated under reduced pressure. The residue was dissolved in water and subjected to a column (2.5×40 cm) chromatography of Diaion SP-207 (made by Mitsubishi Kasei Co., Japan), eluting with water. The eluted fractions were concentrated under reduced pressure and applied to a column chromatography of Amberlite XAD-2, eluting with water. The eluted fractions were lyophiized, to obtain a colorless powder (0.098 g) of Compound 21 (sodium salt).

$^1$H-NMR spectrum (in $D_2O$)δ ppm: 2.71–3.09(2H,m), 2.92(6H,s), 3.70(1H,t,J=5.8Hz), 7.97(1H,s)

Examples 26–27

Compound 1 (hydrochloride) was reacted, in the same way as that of Example 25, with the carbonyl compounds indicated in Table 8 under a reductive alkylation condition, to obtain Compound 22 (sodium salt) and 23 (sodium salt).

column was eluted with a mixed solvent of ethyl acetate and methanol (4:1), to obtain a colorless oily substance (0.31 g) of Compound 24.

$^1$H-NMR($d_6$-DMSO)δ ppm: 0.83–0.96(3H,m), 1.39(9H,s), 2.41–2.67(2H,m), 3.62(3H,s), 3.91–4.08(1H,m), 4.30–4.43(1H,m), 6.92(1H,d,J=8Hz), 7,36(1H,s), 8.18(1H,d,J=8Hz)

To a solution of Compound 24 (0.22 g) in methanol (3 ml) was added 0.5N sodium hydroxide aqueous solution (3.5 ml), followed by stirring for 30 minutes at room temperature. The reaction solution was diluted with water (20 ml) and extracted with ethyl acetate (10 ml). The separated aqueous layer was acidified to pH 3–5 with 5% phosphoric acid aqueous solution and extracted with ethyl acetate (50 ml). The extract was washed with water, dried over anhydrous magnesium sulfate and evaporated under reduced pressure, to obtain a colorless oily substance (0.18 g) of Compound 25.

$^1$H-NMR($d_6$-DMSO)δ ppm: 1.07–1.19(3H,m), 1.39(9H,s), 2.42–2.68(2H,m), 3.89–4.11(1H,m), 4.29–4.43(1H,m), 6.91(1H,d,J=8Hz), 8.02(1H,d,J=8Hz), 8.24(1H,s)

A solution of Compound 25 (0.17 g) in a solution (4N: 10 ml) of hydrogen chloride and dioxane was kept for an hour at room temperature. The reaction mixture was evaporated under reduced pressure. Ethyl ether (20 ml) was added to the residue, by which a colorless powder (0.12 g) of Compound 26 (hydrochloride) was obtained.

TABLE 8

| Example No. | Material 1.HCl | carbonyl compound | NaBH$_3$CN | Product |
|---|---|---|---|---|
| 26 | 0.3 g | Ph–CH$_2$CH$_2$CCH$_3$ (with C=O) (2 ml) | 0.33 g | Compound 22 (sodium salt) (0.17 g) $^1$H-NMR($D_2O$) δ ppm: 1.21–1.29(3H,m), 1.69–2.11(2H,m), 2.58–2.74(4H,m), 3.09–3.31(1H,m), 3.63–3.78(1H,m), 7.14–7.39(5H,m), 7.89(1H,s) SIMS spectrum: (m/z) 305 (M + H)$^+$ 327 (M + Na)$^+$ |
| 27 | 1 g | O ‖ CH$_3$CCH$_3$ (2.5 ml) | 0.6 g | Compound 23 (sodium salt) (0.32 g) $^1$H-NMR($D_2O$) δ ppm: 1.29–1.34(6H,m), 2.71–2.89(2H,m), 3.41–3.53(1H,m), 3.80–3.91(1H,m), 7.98(1H,s) SIMS (m/z): 215 (M + H)$^+$ 237 (M + Na)$^+$ |

EXAMPLE 28

0.47 g of tert-butoxycarbonyl-L-alanine was dissolved in tetrahydrofuran (10 ml) and cooled at −10° C. N-methylmorpholine (0.4 ml) and then isobutylchloroformate (0.49 ml) were added thereto under stirring. The solution was stirred for 15 minutes and a dimentylformamide solution (5) of the Compound 12 (hydrochloride, 1 g) and triethylamine (1.3 ml) was added thereto. The solution was stirred for 60 minutes at −10° C. and ethyl acetate (100 μl) was added thereto. The solution was washed with 5% phosphoric acid aqueous solution and then with water and dried over magnesium sulfate. The solvent was evaporated under reduced pressure therefrom and the residue was applied to a column (2.5×40 cm) chromatography of silica gel. The $^1$H-NMR($D_2O$)δ ppm: 1.52(2H,d,J=7Hz), 2.77–2.83(2H,m), 3.0–3.15(1H,m), 4.56–4.76(1H,m), 8.29(1H,s)

SIMS(m/z): 244 (M+H)$^+$

EXAMPLES 29–32

Compounds 33–35, 41–46 and 89–91 indicated in Table 9 were obtained by condensation reaction of Compound 12 (hydrochloride) and amino acid derivatives followed by deprotection reaction in the same way as in Example 28.

TABLE 9

| Example No. | Starting material | Reagent | Product |
|---|---|---|---|
| 29 | Compound 12 (hydrochloride) (1.7 g) t-butoxycarbonyl-L-leucine (1.5 g) | N-methylmorpholine (0.68 ml) isobutyl-chloroformate (0.82 ml) triethylamine (2.2 ml) | Compound 33 (0.45 g) $^1$H-NMR(d$_6$-DMSO)δ ppm: 0.86–0.89 (6H,m), 1.15–1.69 (3H,m), 1.39 (9H,s), 2.40–2.59 (2H,m), 3.57 (3H,s), 3.91–4.05 (1H,m), 4.12–4.28 (1H,m), 6.66 (1H,d,J=8Hz), 7.58 (1H,s), 8.87 (1H,d,J=8Hz) |
| | Compound 33 (0.45 g) | 0.5 N sodium hydroxide solution (7 ml) | Compound 34 (0.35 g) $^1$H-NMR(d$_6$-DMSO)δ ppm: 0.80–0.98 (6H,m), 1.14–1.62 (3H,m), 1.38 (9H,s), 2.41–2.56 (2H,m), 3.88–4.03 (1H,m), 4.25–4.41 (1H,m), 6.87 (1H,d,J=8Hz), 8.03 (1H,d,J=8Hz), 8.23 (1H,s) |
| | Compound 34 (0.35 g) | 4 N hydrogen chloride-dioxane (15 ml) | Compound 35 (hydrochloride) (0.25 g) $^1$H-NMR(D$_2$O)δ ppm: 0.89–1.04 (6H,m), 1.63–1.82 (3H,m), 2.81–2.86 (2H,m), 3.99–4.06 (1H,m), 4.60–4.67 (1H,m), 8.31 (1H,s) SIMS (m/z): 286 (M + H)$^+$ |
| 30 | Compound 12 (hydrochloride) (0.83 g) N$^α$-benzyloxycarbonyl-3-N$^β$-tert-butoxycarbonylamino-L-alanine (1 g) | N-methylmorpholine (0.33 ml) isobutyl-chloroformate (0.4 ml) triethylamine (1.1 ml) | Compound 41 (0.52 g) $^1$H-NMR(d$_6$-DMSO)δ ppm: 1.37 (9H,s), 2.44–2.57 (2H,m), 3.08–3.42 (2H,m), 3.57 (3H,s), 4.06–4.30 (2H,m), 5.04 (2H,s), 6.62 (1H,b), 7.12 (1H,d,J=8Hz), 7.36 (5H,s), 7.57 (1H,s), 9.14 (1H,b) |
| | Compound 41 (0.5 g) | 0.5 N sodium hydroxide solution (6 ml) | Compound 42 (0.4 g) $^1$H-NMR(d$_6$-DMSO)δ ppm: 1.37 (9H,s), 2.51–2.65 (2H,m), 3.09–3.42 (2H,m), 4.05–4.41 (2H,m), 5.04 (2H,s), 6.65 (1H,b), 7.24 (1H,d,J=7.8Hz), 7.36 (5H,s), 8.21 (1H,b), 8.26 (1H,s) |
| | Compound 42 (0.39 g) | 4 N hydrogen chloride-dioxane (15 ml) | Compound 43 (hydrochloride) (0.26 g) $^1$H-NMR(D$_2$O)δ ppm: 2.59–2.91 (2H,m), 3.25–3.65 (2H,m), 4.45–4.57 (1H,m), 4.60–4.69 (1H,m), 5.16 (2H,s), 7.45 (5H,s), 8.16 (1H,s) SIMS (m/z): 393 (M + H)$^+$ |
| 31 | Compound 12 (hydrochloride) (0.92 g) N$^α$,N$^β$-bis-tert-butoxycarbonyl-3-amino-L-alanine (1.0 g) | N-methylmorpholine (0.37 ml) isobutyl-chloroformate (0.44 ml) triethylamine (1.2 ml) | Compound 44 (0.48 g) $^1$H-NMR(d$_6$-DMSO)δ ppm: 1.38 (18H,s), 2.43–2.54 (2H,m), 3.08–3.49 (2H,m), 3.57 (3H,s), 3.98–4.14 (1H,m), 4.19–4.31 (1H,m), 6.52–6.69 (1H,m), 7.57 (1H,s), 8.93–8.98 (1H,m) |
| | Compound 44 (0.46 g) | 0.5 N-sodium hydroxide solution (6 ml) | Compound 45 (0.39 g) SISM (m/z): 427 (M + H)$^+$ |
| | Compound 45 (0.38 g) | 4 N hydrogen chloride-dioxane (15 ml) | Compound 46 (hydrochloride) (0.25 g) $^1$H-NMR(D$_2$O)δ ppm: 2.74–2.98 (2H,m), 3.59 (2H,d,J=5.8Hz), 4.43 (1H,t,J=5.8Hz), 4.70 (1H,t,J=5.8Hz), 8.32 (1H,s) SIMS (m/z): 259 (M + H)$^+$ |
| 32 | Compound 12 (hydrochloride) (2.5 g) N-tert-butoxycarbonyl-L-phenylalanine (2.0 g) | N-methylmorpholine (0.85 ml) Isobutyl-chloroformate (1.0 ml) triethylamine (3.5 ml) | Compound 90 (0.8 g) $^1$H-NMR(d$_6$-DMSO)δ ppm: 1.30 (9H,s), 2.64–3.19 (4H,m), 3.58 (3H,s), 3.93–4.06 (1H,m), 4.12–4.31 (1H,m), 6.76 (1H,d,J=8Hz), 7.18–7.29 (5H,m), 7.58 (1H,s), 9.33 (1H,m) |
| | Compound 90 (0.78 g) | 0.5 N-sodium hydroxide solution (10.8 ml) | Compound 91 (0.69 g) $^1$H-NMR(d$_6$-DMSO)δ ppm: 1.30 (9H,s), 2.58–3.08 (4H,m), 4.09–4.26 (1H,m), 4.31–4.43 (1H,m), 6.91 (1H,d,J=8Hz), 7.18–7.28 (5H,m), 8.27 (1H,s), 8.25–8.30 (1H,m) |
| | Compound 91 (0.67 g) | 4 N hydrogen chloride-dioxane (20 ml) | Compound 92 (hydrochloride) (0.57 g) $^1$H-NMR(D$_2$O)δ ppm: 2.68–2.82 (2H,m), 3.12–3.43 (2H,m), 4.20–4.31 (1H,m), 4.55–4.62 (1H,m), 7.28–7.44 (5H,m), 8.23 (1H,s) |

EXAMPLE 33

To a solution of 1.06 g of N-tert-butoxy-L-norleucine in 10 ml of dimethylformamide were added 0.83 g of N-hydroxy—5—norbornene—2,3-dicarboximide and 0.94 g of dicyclohexylcarbodiimide, followed by stirring for an hour at room temperature. A solution of 1.22 g of Compound 12 (hydrochloride) and 1.6 ml of triethylamine in 5 ml of dimethylformamide was added to the reaction mixture and stirred for an hour at room temperature. The mixture was diluted with 100 ml of ethyl acetate. After filtering the precipitate off, the filtrate was washed with 5% phosphoric acid aqueous solution and then with water, dried over anhydrous magnesium sulfate and distilled under reduced pressure. The residue was subjected to a silica gel column (2.5×40 cm) chromatography (developed by ethyl acetate:methanol=6:1–5:1) to obtain 0.54 g of Compound 30 as colorless oil.

$^1$H-NMR(d$_6$-DMSO)$\delta$ ppm: 0.80–0.96(3H,b), 1.12–1.42(4H,m), 1.39(9H,s), 1.43–1.70(2H,m), 2.41–2.60(2H,m), 3.58(3H,s), 3.76–3.99(1H,m), 4.21–4.32(1H,m), 6.64(1H,d,J=7.8Hz), 7.12(1H,s), 8.76(1H,d,J=7.8Hz)

To a solution of 0.52 g of Compound 30 in 4 ml of methanol was added 0.5N-sodium hydroxide, followed by stirring for 30 minutes at room temperature. The reaction solution was diluted with 20 ml of water and extracted with 10 ml of ethyl acetate. The collected aqueous layer was acidified to pH 3.5 by addition of 5% phosphoric acid aqueous solution and extracted with 50 ml of ethyl acetate. The extract was washed with water, dried over anhydrous magnesium sulfate and distilled under reduced pressure to obtain 0.45 g of Compound 31 as colorless oil.

$^1$H-NMR(d$_6$-DMSO)$\delta$ ppm: 0.74–0.91(3H,b), 1.12–1.41(4H,m), 1.37(9H,s), 1.41–1.70(2H,m), 2.41–2.60(2H,m), 3.81–3.98(1H,m), 4.21–4.39(1H,m), 6.83(1H,d,J=7.8Hz), 8.05(1H,d,J=7.8Hz), 8.24(1H,s)

Compound 31 (0.42 g) was dissolved in 20 ml of 4N hydrogen chloride-dioxane, stirred for an hour at room temperature and distilled under reduced pressure to remove the solvent. Compound 32 (hydrochloride), 0.36 g as colorless powder was obtained by adding 50 ml of ethyl ether to the residue.

$^1$H-NMR(D$_2$O)$\delta$ ppm: 0.81–0.94(3H,b), 1.31–1.33(4H,m), 1.80–1.87(2H,m), 2.79–2.84(2H,m), 3.99(1H,t,J=6.8Hz), 4.58–4.65(1H,m), 8.30(1H,s)
SIMS(m/z): 286(M+H)$^+$

EXAMPLES 34–36

By the method of Example 33, Compound 12 (hydrochloride) was condensed with an amino acid derivative, followed by removing the protecting group, to obtain Compound 27–29 and 36–40 shown in Table 10.

TABLE 10

| Example No. | Starting compound | Reagent | Product |
|---|---|---|---|
| 34 | Compound 12 (hydrochloride) (0.65 g) N-tert-butoxycarbonyl-L-norvaline (0.53 g) | N-hydroxy-5-norbornene-2,3-dicarboxiimide (HONB) (0.43 g) dicyclohexylcarboimide (DCC) (0.49 g) triethylamine (0.83 ml) | Compound 27 (0.13 g) $^1$H-NMR(d$_6$-DMSO)$\delta$ ppm: 0.85(3H,t,J=7.2Hz), 1.06–1.57(4H,m), 1.37(9H,s), 2.41–2.57(2H,m), 3.55(3H,s), 3.88–4.01(1H,m), 4.11–4.23(1H,m), 6.69(1H,d,J=7.8Hz), 7.59(1H,s), 8.98–9.04(1H,m) |
| | Compound 27 (0.22 g) | 0.5N sodium hydroxide solution (3.4 ml) | Compound 28 (0.15 g) SIMS(m/z): 372(M+H)$^+$ |
| | Compound 28 (0.15 g) | 4N hydrogen chloride-dioxane (15 ml) | Compound 29 (hydrochloride) (0.13 g) $^1$H-NMR(D$_2$O)$\delta$ ppm: 0.93(3H,t,J=7.2Hz), 1.35–1.45(2H,m), 1.79–1.91(2H,m), 2.78–2.86(2H,m), 4.01(1H,t,J=6.8Hz), 4.63(1H,t,J=6.4Hz), 8.31(1H,s) SIMS(m/z): 272(M+H)$^+$ |
| 35 | Compound 12 (hydrochloride) (1.2 g) N-tert-butoxycarbonyl-L-methionine (1.2 g) | HONB (0.83 g) dicyclohexylcarbodiimide (0.94 g) triethylamine (1.6 ml) | Compound 36 (0.42 g) $^1$H-NMR(d$_6$-DMSO)$\delta$ ppm: 1.42(12H,b), 1.74–1.92(2H,m), 2.01–2.21(2H,m), 2.42–2.60(2H,m), 3.61(3H,s), 3.98–4.08(1H,m), 4.18–4.28(1H,m), 6.89(1H,d,J=7.4Hz), 7.58(1H,s), 9.18(1H,m) |
| | Compound 36 (0.42 g) | 0.5N sodium hydroxide solution (6 ml) | Compound 37 (0.27 g) SIMS(m/z): 404(M+H)$^+$ |
| | Compound 37 | 4N hydrogen | Compound 38 |

TABLE 10-continued

| Example No. | Starting compound | Reagent | Product |
|---|---|---|---|
| | (0.27 g) | chloride-dioxane (12 ml) dimethyl-sulfide (0.48 ml) | (hydrochloride) (0.24 g) $^1$H-NMR(D$_2$O)δ ppm: 1.15(3H,t,J=7.4Hz), 2.03-2.23(4H,m), 2.59-2.71(2H,m), 4.13-4.29(1H,m), 4.62-4.72(1H,m), 8.32(1H,s) SIMS(m/z): 304(M+H)$^+$ |
| 36 | Compound 12 (hydrochloride) (0.5 g) N-lauroyl-L-alanine (0.48 g) | HONB (0.32 g) dicyclohexyl-carbodiimide (0.36 g) triethylamine (1.2 ml) | Compound 39 (0.2 g) $^1$H-NMR(d$_6$-DMSO)δ ppm: 0.83-0.89(3H,m), 1.17-1.58(21H,m), 2.08-2.15(2H,m), 2.43-2.50(2H,m), 3.56(3H,s), 4.17-4.39(2H,m), 7.55(1H,s), 8.01(1H,d,J=8Hz), 8.99(1H,d,J=8Hz) |
| | Compound 39 (0.2 g) | 0.5N sodium hydroxide solution (2.5 ml) | Compound 40 (0.13 g) $^1$H-NMR(d$_6$-DMSO)δ ppm: 0.83-0.89(3H,m), 1.09-1.50(21H,m), 2.09(2H,t,J=7.2Hz), 2.47-2.69(2H,m), 4.24-4.33(2H,m), 7.95(1H,d,J=8Hz), 8.13(1H,d,J=8Hz), 8.27(1H,s) Elemental analysis for C$_{21}$H$_{35}$N$_3$O$_6$·½H$_2$O Calculated: C, 58.05; H, 8.35; N, 9.67 Found: C, 58.51; H, 8.26; N, 9.54 SIMS(m/z): 426(M+H)$^+$ |

EXAMPLE 37

To a solution of 0.8 g of Compound 9 and 1.0 g of L-norleucine p-nitrobenzylester·hydrochloride in 10 ml of dimethylformamide were added 0.53 ml of diethyl phosphorocyanidate (abbreviated as DEPC) and 0.82 ml of triethylamine, followed by stirring for an hour. The mixture was diluted with 100 ml of ethyl acetate, and washed with 5% phosphoric acid aqueous solution and water. The organic layer was dried and distilled under reduced pressure. The residue was subjected to a silica gel column (2.5×40 cm) chromatography (developed by a mixture of dichloromethane:acetone:methanol=6:4:1) to obtain 0.62 g of Compound 52 as pale yellow oil.

$^1$H-NMR(d$_6$-DMSO)δ ppm: 0.81-0.94(3H,b), 1.16-1.46(4H,m), 1.37(9H,s), 1.64-1.80(2H,m), 2.32-2.51(2H,m), 4.06-4.15(1H,m), 4.29-4.40(1H,m), 5.28(2H,s), 6.89(1H,d,J=8.2Hz), 7.63(2H,d,J=8.4Hz), 8.13(1H,s,), 8.23(2H,d,J=8.4Hz), 8.28-8.32(1H,m)

To a solution of 0.6 g of Compound 52 in 2 ml of methanol was added 3 ml of 0.5N sodium hydroxide, followed by stirring for 30 minutes at room temperature. The reaction mixture was diluted with 20 ml of water and extracted with 10 ml of ethyl acetate. The aqueous layer was acidified with 5% phosphoric acid (ph 3-5) and extracted with 50 ml of ethyl acetate. The extract was washed with water, dried over anhydrous magnesium sulfate and distilled under reduced pressure to obtain 0.24 g of Compound 53 as colorless oil.

$^1$H-NMR(d$_6$-DMSO)δ ppm: 0.78-0.93(3H,b), 1.15-1.46(4H,m), 1.36(9H,s), 1.55-1.99(2H,m), 2.30-2.51(2H,m), 3.90-4.05(1H,m), 4.19-4.30(1H,m), 7.08(1H,d,J=7.6Hz), 7.91(1H,s), 8.07(1H,d,J=7.4Hz)

A solution of 0.22 g of Compound 53 in 10 ml of 4N hydrogen chloride-dioxane was stirred for an hour at room temperature, and then distilled under reduced pressure to remove the solvent. Ethyl ether (50 ml) was added to the residue to obtain 0.09 g of Compound 54 (hydrochloride) as colorless powders.

$^1$H-NMR(D$_2$O)δ ppm: 0.87-0.90(3H,b), 1.27-1.33(4H,m), 1.73-1.88(2H,m), 2.78-2.84(2H,m), 4.14(1H,t,J=6.8Hz), 4.38-4.47(1H,m), 8.03(1H,s)

SIMS(m/z): 286(M+H)$^+$

EXAMPLES 38-44

By the method of Example 37, the condensation reaction of Compound 9 and an amino acid derivative and the subsequent removal of the protecting group were conducted to obtain compounds 49 to 51, 57 to 60, 47, 48, 55, 56 and 61 to 69 which are shown in Table 11.

TABLE 11

| Example No. | Starting compound | Reagent | Product |
|---|---|---|---|
| 38 | Compound 9 (0.5 g) L-norvaline p-nitro-benzyl ester (0.62 g) | DEPC (0.3 ml) triethylamine (0.46 ml) | Compound 49 (0.52 g) $^1$H-NMR(CDCl$_3$)δ ppm: 0.71–0.90(3H,m), 1.12–1.70(4H,m), 1.37(9H,s), 2.42–2.60(2H,m), 4.08–4.32(1H,m), 4.43–4.60(1H,m), 5.21(2H,s), 7.48(2H,d,J=8.4Hz), 7.81(1H,S), 8.21(2H,d,J=8.4Hz) |
| | Compound 49 (0.51 g) | 0.5N sodium hydroxide (3 ml) | Compound 50 (0.31 g) SIMS(m/z): 372(M+H)$^+$ |
| | Compound 50 (0.31 g) | 4N hydrogen chloride-dioxane (20 ml) | Compound 51 (hydrochloride) (0.25 g) $^1$H-NMR(D$_2$O)δ ppm: 0.85(3H,t,J=7.2Hz), 1.24–1.36(2H,m), 1.65–1.80(2H,m), 2.82–2.86(2H,m), 4.12–4.18(1H,m), 4.27–4.35(1H,m), 8.26(1H,s) SIMS(m/z): 272(M+H)$^+$ |
| 39 | Compound 9 (1 g) L-methionine ethyl ester. hydrochloride (0.8 g) | DEPC (0.66 ml) triethylamine (0.98 ml) | Compound 57 (0.42 g) $^1$H-NMR(CDCl$_3$)δ ppm: 1.13–1.59(15H,m), 1.97–2.17(4H,m), 2.39–2.60(2H,m), 3.99–4.81(4H,m), 7.98(1H,s) |
| | Compound 57 (0.32 g) | 0.5N sodium hydroxide (4.5 ml) | Compound 58 (0.3 g) |
| | Compound 58 (0.3 g) | 4N hydrogen chloride-dioxane (12 ml) dimethyl-sulfide (0.53 ml) | Compound 59 (hydrochloride) (0.23 g) $^1$H-NMR(D$_2$O)δ ppm: 1.17(3H,t,J=7.3Hz), 2.00–2.29(4H,m), 2.48–2.69(2H,m), 4.12–4.28(1H,m), 4.53–4.60(1H,m), 8.32(1H,s), SIMS(m/z): 304(M+H)$^+$ |
| | Compound 57 (0.1 g) | 4N hydrogen chloride-dioxane (4 ml) dimethyl-sulfide (0.17 ml) | Compound 60 (hydrochloride) (0.055 g) $^1$H-NMR(D$_2$O)δ ppm: 1.19–1.40(6H,m), 2.0–2.31(4H,m), 2.47–2.71(2H,m), 4.08–4.37(3H,m), 4.52–4.70(1H,m), 8.33(1H,s) |
| 40 | Compound 9 (1 g) L-alanine t-butyl-ester hydrochloride (0.67 g) | DEPC (0.66 ml) triethylamine (0.98 ml) | Compound 47 (0.35 g) $^1$H-NMR(d$_6$-DMSO)δ ppm: 1.24(3H,d,J=7Hz), 1.36(18H,s), 2.21–2.43(2H,m), 3.82–3.98(1H,m), 4.05–4.21(1H,m), 7.10(1H,d,J=8Hz), 7.62(1H,s), 7.88(1H,d,J=8Hz) |
| | Compound 47 (0.34 g) | 4N hydrogen chloride-dioxane (20 ml) | Compound 48 (hydrochloride) (0.14 g) $^1$H-NMR(D$_2$O)δ ppm: 1.44(3H,d,J=7.4Hz), 2.89(2H,d,J=6.4Hz), 4.17(1H,t,J=6.4Hz), |

TABLE 11-continued

| Example No. | Starting compound | Reagent | Product |
|---|---|---|---|
| | | | 4.39(1H,q,J=7.4Hz, 18 Hz), 8.31(1H,s) SIMS(m/z): 244(M+H)+ |
| 41 | Compound 9 (0.5 g) L-leucine t-butyl-ester hydrochloride (0.41 g) | DEPC (0.3 ml) triethylamine 0.46 ml) | Compound 55 (0.3 g) $^1$H-NMR(d$_6$-DMSO)δ ppm: 0.72–0.98(6H,m), 1.14–1.65(3H,m), 1.39(18H,s), 2.42–2.50(2H,m), 3.81–3.99(1H,m), 4.08–4.27(1H,m), 7.22(1H,d,J=8Hz), 7.61(1H,s), 7.81(1H,d,J=8Hz) |
| | Compound 55 (0.29 g) | 4N hydrogen chloride-dioxane (15 ml) glacial acetic acid (1.5 ml) | Compound 56 (hydrochloride) (0.12 g) $^1$H-NMR(D$_2$O)δ ppm: 0.87–1.02(6H,m), 1.66–1.81(3H,m), 2.91(2H,d,J=6.2Hz), 4.21(1H,t,J=6.2Hz), 4.34–4.48(1H,m), 8.31(1H,s) |
| 42 | Compound 9 (1.3 g) N$^\alpha$-benzyloxy-carbonyl-3-amino-L-alanine methyl ester hydrochloride (1.38 g) | DEPC (0.86 ml) triethylamine (1.2 ml) | Compound 61 (0.499 g) $^1$H-NMR(d$_6$-DMSO)δ ppm: 1.35(9H,s), 2.29–2.48(2H,m), 3.22–3.53(2H,m), 3.62(3H,s), 3.73–3.90(1H,m), 4.07–4.21(1H,m), 5.03(2H,s), 7.36(5H,s), 7.62(1H,b), 7.89(1H,b) |
| | Compound 61 (0.489 g) | 0.5N sodium hydroxide (6 ml) | Compound 62 (0.39 g) $^1$H-NMR(d$_6$-DMSO)δ ppm: 1.35(9H,s), 2.22–2.53(2H,m), 3.22–3.59(2H,m), 3.97–4.19(2H,m), 5.03(2H,s), 7.82(1H,d,J=8Hz), 7.35(5H,s), 7.50(1H,d,J=8Hz), 7.08(1H,b), 8.16(1H,s) |
| | Compound 62 (0.38 g) | 4N hydrogen chloride-dioxane (15 ml) | Compound 63 (hydrochloride) (0.258 g) $^1$H-NMR(D$_2$O)δ ppm: 2.61–2.89(2H,m), 3.31–3.85(2H,m), 4.02–4.18(1H,m), 4.31–4.50(1H,m), 5.16(2H,s), 7.42(5H,s), 8.19(1H,s) SIMS(m/z): 393(M+H)+ |
| 43 | Compound 9 (1 g) glycine ethyl ester hydrochloride (0.51 g) | DEPC (0.66 ml) triethylamine (0.98 ml) | Compound 64 (0.39 g) $^1$H-NMR(d$_6$-DMSO)δ ppm: 1.19(3H,t,J=7Hz), 1.37(9H,s), 2.34–2.49(2H,m), 3.78–3.93(3H,m), 4.08(2H,q,J=7Hz, 15 Hz), 7.17(1H,d,J=7.4Hz), 7.67(1H,s), 8.10–8.19(1H,m) |
| | Compound 64 (0.37 g) | 0.5N sodium hydroxide (6 ml) | Compound 65 (0.31 g) SIMS(m/z): 312(M+H)+ |

TABLE 11-continued

| Example No. | Starting compound | Reagent | Product |
|---|---|---|---|
| | Compound 65 (0.31 g) | 4N hydrogen chloride-dioxane (15 ml) | Compound 66 (hydrochloride) (0.16 g) $^1$H-NMR(D$_2$O)δ ppm: 2.91(2H,J=6.2Hz), 4.03(2H,s), 4.24(1H,t,J=6.2Hz), 8.35(1H,s) SIMS(m/z): 229(M+H)$^+$ |
| 44 | Compound 9 (1 g) β-alanine ethyl-ester hydrochloride (0.56 g) | DEPC (0.66 ml) triethylamine (0.98 ml) | Compound 67 (0.42 g) $^1$H-NMR(d$_6$-DMSO)δ ppm: 1.20(3H,t,J=7Hz), 1.37(9H,s), 2.32-2.41(4H,m), 3.23-3.33(2H,m), 3.79-3.89(1H,m), 4.07(2H,q,J=7Hz, 15 Hz), 7.36-7.39(1H,m), 7.57(1H,s), 7.67-7.81(1H,m) |
| | Compound 67 (0.41 g) | 0.5N sodium hydroxide (6 ml) | Compound 68 (0.24 g) SIMS(m/z): 298(M+H)$^+$ |
| | Compound 68 (0.24 g) | 4N hydrogen chloride-dioxane (15 ml) | Compound 69 (hydrochloride) (0.15 g) $^1$H-NMR(D$_2$O)δ ppm: 2.59(2H,t,J=6.2Hz), 2.85(2H,d,J=6.6Hz), 3.40-3.59(2H,m), 4.11(1H,t,J=6.6Hz), 8.31(1H,s) SIMS(m/z): 244(M+H)$^+$ |

EXAMPLE 45

To a solution of 0.5 g of Compound 9 and 0.18 ml of piperidine in 10 ml of dimethylformamide were added DEPC (0.33 ml) and 0.25 ml of triethylamine under ice-cooling. The mixture was stirred for an hour under ice-cooling and further stirred for 30 minutes at room temperature. The reaction mixture was diluted with ethyl acetate, and the resultant was washed with 5% phosphoric acid solution and water successively, dried over anhydrous magnesium sulfate and distilled to remove the solvent under reduced pressure. The residue was subjected to a silica gel column chromatography (2.5×40 cm; ethyl acetate:methanol=5:1 to 4:1) to obtain Compound 88 (0.32 g) as colorless oil.

$^1$H-NMR(d$_6$-DMSO)δ ppm: 1.24-1.72(6H,m), 1.36(9H,s), 2.16-2.51(2H,m), 3.27-3.56(4H,m), 4.31-4.42(1H,m), 6.88(1H,d,J=8Hz), 7.55(1H,s)

Compound 88 (0.37 g) was dissolved in 20 ml of 4N-hydrogen chloride and stirred for an hour at room temperature. The reaction mixture was concentrated under reduced pressure and diluted with 50 ml of ethyl ether to obtain 0.3 g of Compound 89 (hydrochloride) as colorless powders.

$^1$H-NMR(D$_2$O)δ ppm: 1.38-1.81(6H,m), 2.84(2H,d,J=6.4Hz), 3.45-3.62(4H,m), 4.69(1H,t,J=6.4Hz), 8.31(1H,s)

SIMS(m/z): 240(M+H)$^+$

EXAMPLE 46

To a solution of 4.86 g of methyl (R)-N-tert-butoxycarbonylpyroglutamate in 100 ml of tetrahydrofuran was added a solution of 24.2% lithium diisopropylamide in hexane (14.5 ml) at −78° C. in a stream of nitrogen, and the resultant was stirred for 10 minutes at −78° C. and further stirred for 20 minutes at −40° C. The reaction mixture was again cooled to −78° C., to which a solution of 2.4 ml of isopropyl formate in 3 ml of tetrahydrofuran was dropwise added. After stirring for 10 minutes at −78° C., the reaction mixture was stirred at −40° C. Stirring was continued until the internal temperature was allowed to raise slowly up to −20° C. The reaction mixture to which 4 ml of isopropyl alcohol was added was poured into a mixture of water and ethyl ether and the resultant was extracted with water. The combined aqueous layers were acidified to pH 2 or less with a dilute hydrochloric acid, saturated with sodium chloride and extracted with ethyl acetate. The organic layer was washed with a saline solution, dried over sodium sulfate and distilled to remove the solvent. The residue was subjected to a silica gel column chromatography (2.5×40 cm; ethyl acetate:hexane=2:1→ethyl acetate ethyl acetate:methanol=9:1) to obtain Compound 93 (1.57 g, 29%) as colorless oil.

IR$\nu_{max}^{neat}$cm$^{-1}$: 3350, 3000, 1790, 1755, 1730, 1650.

$^1$H-NMR(CDCl$_3$)δ ppm: 1.51, 1.50,1.49(9H, each s), 2.10-3.10(2H,m), 3.61(0.3H,dd,J=10.4Hz), 3.75-3.85(0.7H,m), 3.76,3.79,3.81(3H, each s), 4.62(0.5H,dd,J=10, 2.5Hz), 4.66(0.5H,dd,J=10.5,3.6Hz), 7.00(0.33H,s), 9.80(0.33H,s), 9.91(0.33H,s)

Hydroxylamine hydrochloride (403 mg) was added to a solution of 1.57 g of Compound 93 in a mixture of 16 ml of 1,4-dioxane and 10 ml of water. The mixture was stirred for an hour at room temperature. The reaction mixture to which 50 ml of ethyl acetate was added was washed with water and a saturated saline solution successively and dried over sodium sulfate. The solvent was distilled to obtain Compound 94 (1.66 g) as colorless oil.

IR$\nu_{max}^{neat}$cm$^{-1}$: 3350, 2990, 1790, 1750, 1690, 1510, 1440.

$^1$H-NMR(CDCl$_3$)δ ppm: 1.49, 1.51(9H,s), 1.90-2.40(2H,m), 3.70-3.85[1H,m], 3.71,3.74,3.79,3.81(3H,s), 4.50-4.70(1H,m), 6.96(0.25H,d,J=4.8Hz), 7.33(0.25H,d,J=5Hz), 7.54(0.25H,d,J=5Hz), 7.58(0.25H,d,J=5Hz).

To a solution of 1.66 g of Compound 94 in 50 ml of methanol was added 12 ml of 0.5N sodium hydroxide. The resultant was stirred for 2 hours and then poured into a mixture of ethyl ether and water. The aqueous layer was adjusted to pH 3 or less with 1N hydrochloric acid, saturated with sodium chloride and extracted with ethyl acetate. The organic layer was washed with a saturated saline solution, dried over sodium sulfate and distilled to remove the solvent. The residue was subjected to a silica gel column chromatography (2.5×40 cm; ethyl acetate ethyl acetate:methanol =9:1) to obtain Compound 70 (1.25 g, 75%) as pale yellow oil.

IR$\nu_{max}^{neat}$cm$^{-1}$: 3400, 2980, 1700, 1600, 1510.

$^1$H-NMR(CDCl$_3$)δ ppm: 1.44(9H,s), 2.70(1H,dd,J=15.8, 6.8Hz), 2.83(1H,dd,J=15.2, 5.6Hz), 3.76(3H,s), 4.44(1H,m), 5.58(1H,d,J=7.2Hz), 7.98(1H,s).

0.5N Sodium hydroxide solution (4.74 ml) was added to 227 mg of Compound 70, and the resultant was stirred for 2 hours at room temperature and washed with ethyl. acetate. The aqueous layer taken out was adjusted to pH 2.7 or less with 1N hydrochloric acid, saturated with sodium chloride and extracted with ethyl acetate. The combined organic layers were washed with a saturated saline solution, dried over sodium sulfate and distilled to remove the solvent to obtain 170 mg (79%) of Compound 71 as pale yellow foam.

IR$\nu_{max}^{KBr}$cm$^{-1}$: 3400, 1740-1690, 1530, 1400.

$^1$H-NMR(d$_6$-DMSO)δ ppm: 1.37(9H,s), 2.43(1H,dd,J=9.4, 14.6Hz), 2.57(1H,dd,J=5.1, 14.6Hz), 4.02(1H,dd,,J=5.1, 8.2 9.4Hz) 7.12(1H,d,J=8Hz), 8.24(1H,s).

A mixture of 150 mg of Compound 71 and 10 ml of 4N hydrogen chloride-dioxane was stirred for an hour at room temperature and distilled to remove the solvent. The residue was washed three times with ethyl ether and the solvent was removed by decantation. The residue was dried to obtain hydrochloride of Compound 72 (127 mg) as colorless powders.

IR$\nu_{max}^{KBr}$cm$^{-1}$: 3400, 1640, 1510, 1410.

$^1$H-NMR(D$_2$O)δ ppm: 2.95(2H,d,J=5.8Hz), 4.23(1H,t,J=5.8Hz), 8.36(1H,s).

SIMS(m/z): 173(M+H)+

EXAMPLE 47

2.94 ml (21 m mol) of diisopropylamine and 14 ml (22 m mol) of 1.6M butyllithium in hexane were added to 40 ml of tetrahydrofuran at −78° C. in a stream of nitrogen and the mixture was stirred for 10 minutes. To the reaction mixture was added dropwise a solution of 2.43, g of methyl (S)-N-tert-butoxycarbonyl-pyroglutamate in 15 ml of tetrahydrofuran. The resultant was stirred for 10 minutes, and a solution of 1.32 g of N-acetylimidazole in 10 ml of tetrahydrofuran was added dropwise. The resultant was stirred for 10 minutes at −78° C. and the temperature was raised to −40° C. Stirring was continued until the internal temperature reached −20° C. To the reaction solution was added a saturated ammonium chloride solution, and the resultant was extracted with ethyl acetate. The combined organic layers were washed successively with water and a saturated ammonium chloride solution, dried over sodium sulfate and distilled to remove the solvent. The residue was subjected to a silica gel column chromatography (2.5×40 cm; ethyl acetate:hexane=1:1→2:1) to obtain Compound 95 (2.04 g, 72%) as colorless oil.

IR$\nu_{max}^{neat}$cm$^{-1}$: 3000, 1800, 1755, 1730, 1640.

$^1$H-NMR(CDCl$_3$)δ ppm: 1.48(9H,s), 2.0-2.8(2H,m), 2.40(1.5H,s), 2.42(1.5H,s), 3.6-3.8(1H,m), 3.76(3H,s), 4.53(1H,dd,J=9, 3Hz)

Hydroxylamine·hydrochloride (497 mg) was added to a solution of 2.04 g of Compound 95 in a mixture of 12 ml of 1,4-dioxane and 10 ml of water and the resulting mixture was stirred for 2 hours at room temperature. The reaction mixture to which 14.2 ml of 0.5N-sodium hydroxide were added was stirred for an hour. The resultant was acidified to pH 6.5 or less with 1N-hydrochloric acid and extracted with ethyl acetate. The combined organic layers were washed successively with water and a saturated saline solution, dried over sodium sulfate and distilled to remove the solvent. The residue was subjected to a silica gel column (2.5×25 cm) chromatography (ethyl acetate-hexane 1:1→ ethyl acetate-→ethyl acetate:methanol=9:1) to obtain a pale yellow oil, which is recrystallized from hexane to obtain Compound 73 (956 mg, 45%) as colorless prisms.

mp 134-136° C.

[α]$_D^{24}$ − 16.5° (c=0.5, MeOH)

IR$\nu_{max}^{neat}$cm$^{-1}$: 3400, 1750, 1720, 1620, 1510.

$^1$H-NMR(CDCl$_3$)δ ppm: 1.36(9H,s), 2.07(3H,s), 2.50-2.80(2H,m), 3.69(3H,s), 4.35(1H,m), 5.90(1H,br).

A mixture of 320 mg of Compound 73 and 6.4 ml of 0.5N sodium hydroxide solution was stirred for 30 minutes at room temperature. The reaction mixture was washed with ethyl acetate. The aqueous layer was acidified to pH 2.7 or less with 1N-hydrochloric acid, saturated with sodium chloride and extracted with ethyl acetate. The combined organic layers were washed with a saturated saline solution, dried over sodium sulfate and distilled to remove the solvent to obtain Compound 74 (238 mg, 78%) as pale yellow foam.

IR$\nu_{max}^{KBr}$cm$^-$: 3200, 1740-1680, 1600, 1520.

$^1$H-NMR(CDCl$_3$-acetone-d$_6$)δ ppm: 1.43(9H,s), 2.17(3H,s), 2.60-2.90(2H,m), 4.40(1H,m).

A mixture of 410 mg of Compound 74 in 20 ml of 4N-hydrogen chloride-dioxane was stirred for an hour at room temperature and distilled to remove the solvent. The residue was washed three times with ethyl ether by decantation, and dried to obtain hydrochloride of Compound 75 (351 mg, 75%) as colorless powder.

IR$\nu_{max}^{KBr}$cm$^{-1}$: 3400, 1640, 1500, 1420.

$^1$H-NMR(D$_2$O)δ ppm: 2.22(3H,s), 2.91(2H,d,J=6.2Hz), 4.18(1H,t,J=6.2Hz).

SIMS(m/z): 187(M+H)+

EXAMPLE 48

2.94 ml of diisopropylamine and 1.6M butyllithium-hexane solution (14 ml) were added to 40 ml of tetrahydrofuran at −78° C. in a stream of nitrogen and the mixture was stirred for 10 minutes. A solution of 2.43 g of methyl (R)-N-tert-butoxycarbonylpyroglutamate in 15 ml of tetrahydrofuran was added dropwise to the reaction mixture and stirred for 10 minutes. Then, a solution of 1.32 g of N-acetylimidazole in 10 ml of tetrahydrofuran was added dropwise to the mixture and stirred for 10 minutes at −78° C. The temperature of the reaction mixture was raised up to −40° C. Then the mixture was stirred until the inner temperature showed −20° C. After adding a saturated ammonium chloride aqueous solution, the reaction mixture was extracted with ethyl acetate. The combined organic layers were washed with water and then a saturated saline solution and dried over sodium sulfate. The residue after removing the solvent was subjected to a silica gel column (2.5×40 cm) chromatography (developing by ethyl acetate:hexane=1:1→2:1) to obtain 1.46 g (51%) of Compound 96 as colorless oil.

IR$\nu_{max}^{neat}$cm$^{-1}$: 3000, 1800, 1760, 1730, 1640.

$^1$H-NMR(CDCl$_3$)$\delta$ ppm: 1.46(9H,s), 2.0–2.8(2H,m), 2.37(1.5H,s), 2.43(1.5H,s), 3.4–3.8(1H,m), 3.76(3H,s), 4.53(1H,dd,J=9, 3Hz)

To a solution of 1.46 g of Compound 96 in 9 ml of 1,4-dioxane and 8 ml of water was added 335 mg (5.11 m mol) of hydroxylamine·hydrochloride, followed by stirring for 2 hours at room temperature. 0.5N-Sodium hydroxide (14.2 ml) was added to the reaction mixture, stirred for an hour, acidified to pH 6.5 or less with 1N-hydrochloric acid and extracted with ethyl acetate. The combined organic layers were washed with water and then with a saturated saline solution, dried over sodium sulfate and distilled to remove the solvent. The residue was subjected to a silica gel column (2.5×40 cm) chromatography (developed by ethyl acetate-hexane = 1:1→ethyl acetate→ethyl acetate-methanol=9:1) and the resulting oil was crystallized from hexane. Compound 76 (658 mg, 43%) was obtained as colorless prisms.

mp 134–136° C.

[α]$_D^{24}$ +16.3° (c=0.3, in CH$_3$OH).

IR$\nu_{max}^{neat}$cm$^{-1}$: 3400, 3000, 1760–1720, 1620, 1510.

$^1$H-NMR(CDCl$_3$)$\delta$ ppm: 1.40(9H,s), 2.07(3H,s), 2.50–2.80(2H,m), 3.69(3H,s), 4.35(1H,m), 5.90(1H,br).

A mixture of 658 mg of Compound 76 and 13 ml of 0.5N-sodium hydroxide was stirred for 30 minutes at room temperature and then washed with ethyl acetate. The collected aqueous layer was acidified to pH 2.7 or less with 1N-hydrochloric acid, saturated with sodium chloride and extracted with ethyl acetate. The combined organic layers were washed with a saturated saline solution and dried over sodium sulfate. By removing the solvent, 501 mg (80%) of Compound 77 were obtained as pale yellow foam.

IR$\nu_{max}^{neat}$cm$^{-1}$: 3200, 1740–1680, 1600, 1520.

$^1$H-NMR(CDCl$_3$-acetone-d$_6$)$\delta$ ppm: 1.40(9H,s), 2.14(3H,s), 2.60–2.90(2H,m), 4.39(1H,m).

A mixture of 325 mg of Compound 77 and 20 ml of 4N-hydrogen chloride-dioxane was stirred for an hour at room temperature. The reaction mixture was distilled to remove the solvent and the residue was treated three times with ethyl ether by decantation. The residue was dried to obtain 285 mg (88%) of Compound 78 (hydrochloride) as colorless powders.

IR$\nu_{max}^{KBr}$cm$^{-1}$: 3400, 1640, 1500, 1420.

$^1$H-NMR(D$_2$O)$\delta$ ppm: 2.22(3H,s), 2.91(2H,d,J=6.2Hz), 4.18(1H,t,J=6.2Hz).

SIMS(m/z): 187(M+H)$^+$

EXAMPLE 49

To 40 ml of tetrahydrofuran were added 1.5 ml of diisopropylamine and 6.9 ml of 1.6M butyllithium-hexane solution at −78° C. in a stream of nitrogen, followed by stirring for 10 minutes. A solution of 2.43 g of methyl (S)-N-tert-butoxycarbonylpyroglutamate in 15 ml of tetrahydrofuran was added to the reaction mixture and the resulting mixture was stirred for 10 minutes at −78° C. and then for 20 minutes at −40° C. To the reaction mixture which was again cooled to −78° C. and then was added dropwise a solution of 0.8 ml of propionaldehyde in 4 ml of tetrahydrofuran. After stirring for 10 minutes, the reaction mixture was added with a saturated ammonium chloride aqueous solution and stirred until the temperature of the mixture reached room temperature. The reaction mixture was extracted with ethyl acetate. The combined organic layers were washed with water and a saturated saline solution, dried over sodium sulfate and distilled to remove the solvent. The residue was subjected to a column (2.5×40 cm) chromatography (developed by ethyl acetate-hexane×1:3→1:2→1:1) to obtain 1.2 g (40%) of methyl (S)-N-tert-butoxycarbonyl-4-(1-hydroxy-1-propyl)-pyroglutamate as colorless oil.

IR$\nu_{max}^{neat}$cm$^{-1}$: 3500, 2990, 1780, 1750, 1720, 1640, 1460, 1370.

$^1$H-NMR(CDCl$_3$)$\delta$ ppm: 0.99(3H,t,J=7.2Hz), 1.50(2H,m), 1.51(9H,s), 1.90–2.25(2H,m), 3.69(2H,m), 3.81(3H,s), 4.61(1H,dd,J=9, 1.8Hz)

Oxalyl chloride (0.36 ml) and a solution of 0.52 ml of dimethylsulfoxide in 2 ml of dichloromethane were added to 8 ml of dichloromethane at −60° C. in a stream of nitrogen and the mixture was stirred for 2 minutes. To the mixture was added a solution of 1.01 g of methyl (S)-N-tert-butoxycarbonyl-4-(1-hydroxy−1-propyl)pyroglutamate in 5 ml of dichloromethane during 5 minutes, followed by stirring for 15 minutes at −60° C. Triethylamine (2.34 ml, 16.79 m mol) was added to the reaction mixture and stirred for 5 minutes at −60° C. and for an hour at room temperature. After adding water, the organic layer was collected and the aqueous layer was extracted with dichloromethane. The combined organic layers were washed with a saturated saline solution, dried over sodium sulfate and distilled to remove the solvent. The residue was subjected to a column (2.5×40 cm) chromatography (in ethyl acetate-hexane 1:3–1:2 1:1) to obtain 657 mg (66%) of Compound 97 as colorless oil.

IR$\nu_{max}^{neat}$cm$^{-1}$: 2980, 1780, 1750, 1720, 1630, 1480, 1370.

$^1$H-NMR(CDCl$_3$)$\delta$ ppm: 1.06(1.5H,t,J=7.2Hz), 1.09(1.5H,t,J=7.2Hz), 1.50(9H,s), 1.90–3.20(4H,m), 3.63(1H,dd,J=9.6, 3.6Hz), 3.78, 3.80(3H, each s), 4.60(0.5H,dd,J=7.2, 3Hz), 4.66(0.5H,dd,J=6.8, 3.2Hz)

To a solution of 379 mg of Compound 97 in a mixture of 2m of 1,4-dioxane and 1 ml of water was added 97 mg (1.40 m mol) of hydroxylamine·hydrochloride, followed by stirring for an hour. To the mixture was added 0.5N sodium hydroxide aqueous solution (2.54 ml). After stirring for one hour, the reaction mixture was acidified to pH 3 or less with 1N-hydrochloric acid, saturated with sodium chloride and extracted with ethyl acetate. The organic layer was washed with a saturated acetate. The organic layer was washed with a saturated saline solution, dried over sodium sulfate and distilled to remove the solvent. The residue was subjected to a column (2.5×40 cm) chromatography (developed by ethyl acetate→ethyl acetate:methanol=9:1) to obtain 276 mg (69%) of Compound 79 as pale yellow oil.

IR$\nu_{max}^{neat}$cm$^{-1}$: 3380, 2980, 1710, 1690, 1620, 1500, 1160.

$^1$H-NMR(CDCl$_3$)$\delta$ ppm: 1.23(3H,t,J=7.4Hz), 1.41(9H,s), 2.55(2H,d,J=7.4Hz), 2.70(2H,m), 3.72(3H,s), 4.43(1H,m), 5.95(1H,d,J=7.6Hz).

A mixture of 493 mg of Compound 79 and 9.42 ml of 0.5N-sodium hydroxide was stirred for 2 hours at room temperature. The reaction mixture was washed with ethyl acetate. The aqueous layer was acidified to pH 2.7 or less with 1N-hydrochloric acid, saturated with sodium chloride and extracted with ethyl acetate. The combined organic layer was washed with a saturated saline solution, dried over sodium sulfate and distilled to obtain 461 mg (98%) of Compound 80 as pale yellow foam.

IR$\nu_{max}^{KBr}$cm$^{-1}$: 3200, 2990, 1720, 1690, 1590, 1520, 1390.

$^1$H-NMR(CDCl$_3$)$\delta$ ppm: 1.21(3H,t,J=7.4Hz), 1.44(9H,s), 2.59(2H,q,J=7.4Hz), 2.75(2H,m), 4.42(1H,m), 6.33(1H,d,J=8.2Hz).

A mixture of 461 mg of Compound 80 and 20 ml of 4N-hydrogen chloride-dioxane was stirred for an hour at room temperature and distilled to remove the solvent. The residue was treated three times with ethyl ether by decantation, and dried to obtain 414 mg (81%) of Compound 81 (hydrochloride) as colorless powders.

IR$\nu_{max}^{KBr}$cm$^{-1}$: 3410, 2970, 1720, 1680, 1580, 1500.

$^1$H-NMR(D$_2$O)$\delta$ ppm: 1.20(3H,t,J=7.6Hz), 2.56(2H,q,J=7.6Hz), 2.92(2H,d,J=6.2Hz), 4.23(1H,t,J=6.2Hz).

SIMS(m/z): 201(M+H)$^+$

EXAMPLE 50

To 40 ml of tetrahydrofuran were added 1.54 ml of diisopropylamine and 6.9 ml of 1.6M butyllithium-hexane solution, followed by stirring for 10 minutes under a stream of nitrogen. A solution of 2.43 g of methyl (S)-N-tert-butoxycarbonyl pyroglutamate in 15 ml of tetrahydrofuran was added to the reaction mixture at −78° C. in a stream of nitrogen, and stirred for 10 minutes at −78° C. and for 20 minutes at −40° C. To the reaction mixture which was again cooled to −78° C. was added dropwise a solution of 1.0 ml (11 m mol) of isobutyraldehyde in 4 ml of tetrahydrofuran, followed by stirring for 10 minutes. A saturated ammonium chloride solution was added to the reaction mixture and stirred until the temperature of the reaction mixture reached room temperature. The mixture was extracted with ethyl acetate. The collected organic layers were washed with water and then a saturated saline solution, dried over magnesium sulfate and distilled to remove the solvent. The residue was subjected to a silica gel column (2.5×40 cm) chromatography (developed by ethyl acetate-hexane=1:3→1:2→1:1) to obtain 2.18 g (69%) of methyl (S)-N-tert-butoxycarbonyl-4-(1-hydroxy−2-methyl-1-propyl)pyroglutamate as colorless oil.

IR$\nu_{max}^{neat}$cm$^{-1}$: 3520, 2980, 1780, 1750, 1720, 1640, 1460, 1420, 1370.

$^1$H-NMR(CDCl$_3$)$\delta$ ppm: 0.90(3H,d,J=6.8Hz), 1.04(3H,d,J=6.8Hz), 1.51(9H,s), 1.69(1H,m), 1.91-2.50(2H,m), 2.72(1H,m), 3.60(1H,m), 3.81(3H,s), 4.61(1H,dd,J=8.8, 2.2Hz)

To 17 ml of dichloromethane were added 0.73 ml of oxalyl chloride and a mixture of 1.08 ml of dimethylsulfoxide and 2 ml of dichloromethane at −60° C. in a stream of nitrogen, followed by stirring for 2 minutes. A solution of 2.18 g of methyl (S)-N-tert-butoxycarbonyl-4-(1-hydroxy−2-methyl−1-propyl)pyroglutamate in 6 ml of dichloromethane was added to the reaction mixture during 5 minutes and stirred for 15 minutes at −60° C. After adding 4.83 ml (34.65 m mol) of triethylamine, the mixture was stirred for 5 minutes and further stirred for an hour at room temperature. The reaction mixture was diluted with water and the organic layer was collected. The aqueous layer was extracted with dichloromethane. The combined organic layers were washed with a saturated saline solution, dried over sodium sulfate and distilled to remove the solvent. The residue was subjected to a silica gel column (2.5×40 cm) chromatography (developed by ethyl acetate-hexane=1:3→1:2→1:1) to obtain 1.03 g (48%) of Compound 98 as colorless oil.

IR$\nu_{max}^{neat}$cm$^{-1}$: 2990, 1790, 1750, 1720, 1630, 1460, 1370.

$^1$H-NMR(CDCl$_3$)$\delta$ ppm: 1.13(6H,d,J=7Hz), 1.49(9H,s), 1.90-3.41(4H,m), 3.77, 3.80(3H,s), 4.61(0.5H,dd,J=9.2, 3Hz), 4.65(0.5H,dd,J=9.6, 3.2Hz), To a mixture of 1.03 g of Compound 98 in 5 ml of 1,4-dioxane and 2 ml of water was added 251 mg of hydroxylamine·hydrochloride, followed by stirring for an hour at room temperature. 0.5N-Sodium hydroxide (7.25 ml) was added to the reaction mixture. The resulting mixture was stirred for an hour, acidified to pH 3 or less with 1N-hydrochloric acid, saturated with sodium chloride and extracted with ethyl acetate. The organic layer was washed with a saturated saline solution, dried over sodium sulfate and distilled to remove the solvent. The residue was subjected to a silica gel column (2.5×40 cm) chromatography (developed by ethyl acetate-methanol=9:1) to obtain 259 mg (24%) of Compound 82 as pale yellow oil.

IR$\nu_{max}^{neat}$cm$^{-1}$: 3380, 2980, 1710, 1670, 1620, 1500, 1430.

$^1$H-NMR(CDCl$_3$)$\delta$ ppm: 1.24(6H,d,J=7Hz), 1.40(9H,s), 2.65(2H,m), 2.85(1H,m), 3.69(1H,m,s), 4.48(1H,m), 6.02(1H,m).

A mixture of 473 mg of Compound 82 and 8.64 ml of 0.5N-sodium hydroxide was stirred for 2 hours at room temperature. The reaction mixture was washed with ethyl acetate. The collected aqueous layer was acidified to pH 2.7 or less with 1N-hydrochloric acid, saturated with sodium chloride and extracted with ethyl acetate. The combined organic layers were washed with a saturated saline solution, dried over sodium sulfate and distilled to obtain 450 mg (99%) of Compound 83 as pale yellow foam.

IR$\nu_{max}^{KBr}$cm$^{-1}$: 3200, 2990, 1720, 1660, 1520, 1400, 1360.

$^1$H-NMR(CDCl$_3$)$\delta$ ppm: 1.24(6H,d,J=7Hz), 1.43(9H,s), 2.71(1H,dd,J=14, 4.6Hz), 2.84(1H,dd,J=16, 6Hz), 3.04(1H,m), 4.45(1H,m), 6.34(1H,m).

A mixture of 438 mg of Compound 83 and 20 ml of 4N-hydrogen chloride-dioxane was stirred for an hour at room temperature. After removing the solvent, the residue was treated three times with ethyl ether using decantation. The residue was dried to obtain 396 mg (82%) of Compound 84 (hydrochloride) as colorless powders.

IR$\nu_{max}^{KBr}$cm$^{-1}$: 3420, 2990, 1720, 1660, 1520, 1400.

$^1$H-NMR(D$_2$O)$\delta$ ppm: 1.24(6H,d,J=7Hz), 2.93(2H,d,J=6.2Hz), 3.10(1H,m,J=7Hz), 4.21(1H,t,J=6.2Hz).

SIMS(m/z): 215(M+H)$^+$

EXAMPLE 51

To 40 ml of tetrahydrofuran were added 1.54 ml (11 m mol) of diisopropylamine and 6.9 ml of 1.6M butyllithium-hexane solution, followed by stirring for 10 minutes under a stream of nitrogen. A solution of 2.43 g of methyl (S)-N-tert-butoxycarbonylpyroglutamate in 15 ml of tetrahydrofuran, was added and stirred for 10 minutes at −78° C. and further for 20 minutes at −40° C. To the reaction mixture which was again cooled to −78° C. was added dropwise a solution of 1.12 ml (11 m mol) of benzaldehyde in 4 ml of tetrahydrofuran. After stirring for 10 minutes, the reaction mixture was diluted with a saturated ammonium chloride solution, stirred until the temperature of the mixture reached room temperature and extracted with ethyl acetate. The combined organic layers were washed with water and then a saturated saline solution, dried over sodium sulfate and distilled to remove the solvent. The residue was subjected to a silica gel column (2.5×40 cm) chromatography (developed by ethyl acetate-hexane=1:3→1:2→1:1) to obtain 2.26 g (65%) of methyl (S)-N-tert-butoxycarbonyl-4-(α-hydroxybenzyl)pyroglutamate as colorless oil.

IR$\nu_{max}^{neat}$cm$^{-1}$: 3490, 3030, 2980, 1790, 1750, 1450, 1370.

$^1$H-NMR(CDCl$_3$)δ ppm: 1.46(9H,s), 2.30–3.30(3H,m), 3.66(3H), 4.51(1H,dd,J=10, 15Hz), 5.40(1H,dd,J=2.7, 2Hz), 7.29(5H,s).

To 16 ml of dichloromethane were added 0.68 ml (7.10 m mol) of oxalyl chloride and a mixture of 1.01 ml (14.2 m mol) of dimethylsulfoxide and 3 ml of dichloromethane at −60° C. in a stream of nitrogen, followed by stirring for 2 minutes. A solution of 2.26 g of methyl (S)-N-tert-butoxycarbonyl-4-(α-hydroxybenzyl)pyroglutamate in 5 ml of dichloromethane was added to the reaction mixture during 5 minutes and stirred for 15 minutes at −60° C. After adding 4.51 ml (32.4 m mol) of triethylamine, the reaction mixture was stirred for 5 minutes at −60° C. and further for an hour at room temperature. To the reaction mixture was added water, and the organic layer was collected. The aqueous layer was extracted with dichloromethane. The combined organic layers were washed with a saturated saline solution, dried over sodium sulfate and distilled to remove the solvent. The residue was subjected to a silica gel column (2.5×40 cm) chromatography (developed by ethyl acetate-hexane=1:3→1:2→1:1) to obtain 1.54 g (69%) of Compound 99 as colorless oil.

IR$\nu_{max}^{neat}$cm$^{-1}$: 3020, 2980, 1790, 1750, 1685, 1600, 1480, 1370.

$^1$H-NMR(CDCl$_3$)δ ppm: 1.50(9H,s), 2.01–3.30(3H,m), 3.79(3H), 4.35(1H,m), 4.20–4.80(1H,m), 7.20–7.70(3H,m), 8.02–8.20(3H,m).

To a solution of 1.54 g of Compound 99 in 35 ml of ethanol were added 309 mg (4.45 m mol) of hydroxylamine·hydrochloride and 235 mg (2.22 m mol) of sodium carbonate in a stream of argon, followed by refluxing for an hour. An insoluble substance was filtered off, and the filtrate was concentrated and subjected to a silica gel column (2.5×40 cm) chromatography (developed by ethyl acetate-hexane=1:2→2:1→ethyl acetate→ethyl acetate-methanol=9:1) to obtain 1.21 g (75%) of Compound 85 as pale yellow foam.

IR$\nu_{max}^{neat}$cm$^{-1}$: 3360, 3010, 2980, 1740, 1710, 1680, 1610, 1580, 1480.

$^1$H-NMR(CDCl$_3$)δ ppm: 1.33(9H,s), 2.76(2H,m), 3.48(3H,s), 4.35(1H,m), 7.40(5H,s).

A mixture of 1.21 g of Compound 85 and 20 ml of 0.5N-sodium hydroxide was stirred for 2 hours at room temperature. The reaction mixture was washed with ethyl acetate. The aqueous layer was acidified to pH 2.7 or less with 1N-hydrochloric acid, saturated with sodium chloride and extracted with ethyl acetate. The combined organic layers were washed with a saturated saline solution, dried over sodium sulfate and distilled to obtain 1.14 g (98%) of Compound 86 as pale yellow foam.

IR$\nu_{max}^{neat}$cm$^{-1}$: 3400, 1702, 1680, 1520, 14400.

$^1$H-NMR(CDCl$_3$)δ ppm: 1.33(9H,s), 2.86(2H,d,J=6Hz), 4.42(1H,m), 6.08(1H,br), 7.48(5H,s)

4N-Hydrogen chloride-dioxane (6 ml) was added to 0.101 g of Compound 86. The resulting mixture was stirred for an hour at room temperature and distilled to remove the solvent. The residue was treated three times with ethyl ether using decantation. The residue was dried to obtain 76 mg of Compound 87 (hydrochloride) as colorless powder.

IR$\nu_{max}^{KBr}$cm$^{-1}$: 3420, 2940, 1690, 1610, 1500, 1110.

$^1$H-NMR(D$_2$O)δ ppm: 3.11(2H,d,J=6.4Hz), 4.22(1H,t,J=6.4Hz), 7.62(5H,s)

SIMS(m/z): 249(M+H)$^+$

EXAMPLE 52

To 27 ml of tetrahydrofuran were added 1.05 ml (7.49 m mol) of diisopropylamine and 4.7 ml of 1.6 M butyllithium-hexane solution at −78° C. in a stream of nitrogen, followed by stirring for 10 minutes. To the reaction mixture was added dropwise a solution of 1.94 g of tert-butyl (S)-N-tert-butoxycarbonylpyroglutamate in 10 ml of tetrahydrofuran. The mixture was stirred for 20 minutes at −40° C. and cooled to −78° C. A solution of 0.81 ml (8.09 m mol) of isopropyl formate in 3 ml of tetrahydrofuran was dropwise added to the mixture, stirred for 10 minutes at −78° C., raised to −40° C. and then stirred until the temperature reached −20° C. After adding 4 ml of isopropanol, the reaction mixture was poured into ethyl ether-water and extracted with water. The combined aqueous layers were acidified to pH 2 or less with 1N-hydrochloric acid, saturated with sodium chloride and extracted with ethyl acetate. The combined organic layers were washed with a saturated saline solution, dried over sodium sulfate and distilled to remove the solvent. The residue was subjected to a column (2.5×20 cm) chromatography (carrier: florisil, developing solvent: ethyl acetate→acetate-methanol=10:1) to obtain 622 mg (29%) of Compound 100 as colorless oil.

IR$\nu_{max}^{neat}$cm$^{-1}$: 3350, 3000, 1790, 1755, 1730, 1650.

$^1$H-NMR(CDCl$_3$)δ ppm: 1.45, 1.46, 1.47, 1.48, 1.49, 1.51, 1.52(18H, each s), 2.20–3.05(2H,m), 3.40–3.80(1H,m), 4.80–4.10(1H,m), 7.00(0.33H,s), 9.79(0.33H,s), 9.91(0.33H,s)

To a solution of 235 mg of Compound 100 in a mixture of 3 ml of 1,4-dioxane and 1 ml of water was added 57 mg (0.82 m mol) of hydroxylamine·hydrochloride, followed by stirring for an hour at room temperature. After adding 20 ml of ethyl acetate, the reaction mixture was washed with water and a saturated saline solution. The organic layer was dried over sodium sulfate and distilled to obtain 226 mg (69%) of Compound 101 as oil.

IR$\nu_{max}^{neat}$cm$^{-1}$: 3400, 2990, 1780, 1740, 1690, 1480, 1450.

$^1$H-NMR(CDCl$_3$)δ ppm: 1.46, 1.47, 1.48, 1.49, 1.50, 1.52 (18H, each s), 1.90–2.40(2H,m), 3.40–3.75(1H,m), 4.30–4.65(1H,m), 6.98(0.25H,d,J=5Hz), 7.54(0.25H,d,J=5Hz), 7.58(0.25H,d,J=5Hz)

EXAMPLE 53

To 40 ml of tetrahydrofuran were added 1.45 ml (11 m mol) of diisopropylamine and 7.3 ml of 1.6M butyllithium-hexan solution at −78° C. in a stream of nitrogen, followed by stirring for 10 minutes. A solution of 1.31 g of dimethyl (S)-N-tert-butoxycarbonyl aspartate in 5 ml of tetrahydrofuran was added to the reaction mixture, and stirred for 10 minutes at −78° C. and for 20 minutes at −40° C. To the reaction mixture cooled to −78° C. was added a solution of 0.6 ml (6 m mol) of isopropyl formate in 1 ml of tetrahydrofuran, followed by stirring for 10 minutes. The reaction mixture was stirred at −40° C. and then stirring was continued until the temperature reached −20° C. The reaction mixture to which 2 ml of isopropanol were added was poured into water-ethyl ether and extracted with water. The combined aqueous layers were acidified to pH 2 or less with 1N-hydrochloric acid, saturated with sodium chloride and extracted with ethyl acetate. The organic layer was washed with a saturated saline solution, dried over sodium sulfate and distilled to remove the solvent. The residue was subjected to a silica gel column (2.5×40 cm) chromatography (developed by ethyl acetate-hexane=1:1) to obtain 407 mg (28%) of dimethyl (S)-N-tert-butoxycarbonyl-3-formyl-aspartate as colorless oil.

IR$\nu_{max}^{neat}$cm$^{-1}$: 3350, 2990, 1760-1660, 1500, 1440, 1400.

$^1$H-NMR(CDCl$_3$)δ ppm: 1.45(9H,s), 3.60-4.00(1H,m), 3.69, 3.74, 3.76, 3.79, 3.83(6H,s), 4.83(0.5H,m), 5.08(0.5H,m), 5.52(1H,m), 7.72(0.33H,s), 9.83(0.33H,s), 9.84(0.33H,s)

To a solution of 407 mg of dimethyl (S)-N-tert-butoxycarbonyl-3-formylaspartate in a mixture of 4 ml of 1,4-dioxane and 3 ml of water was added 98 mg (1.41 m mol) of hydroxylamine·hydrochloride, followed by stirring for an hour at room temperature. The reaction mixture was diluted with 20 ml of ethyl acetate, washed with water and a saturated saline solution. The organic layer was dried over sodium sulfate. After removing the solvent, the residue was dissolved in 10 ml of methanol, to which 2.8 ml of 0.5N-sodium hydroxide was added and the mixture was, stirred for an hour. The reaction mixture was adjusted to pH 7.0 or less by addition of 1N-hydrochloric acid and then concentrated. The concentrate was adjusted to pH 3 or less by 1N-hydrochloric acid, saturated with sodium chloride and extracted with ethyl acetate. The resulting organic layer was washed with a saturated saline solution, dried over sodium sulfate and distilled to remove the solvent. The residue was subjected to a silica gel column (2.5×40 cm) chromatography (developed by ethyl acetate ethyl acetate-methanol=9:1-4:1) to obtain 206 mg (54%) of Compound 102 as pale yellow foam.

IR$\nu_{max}^{neat}$cm$^{-1}$: 3400, 2980, 1740-1680, 1630, 1520.

$^1$H-NMR(CDCl$_3$)δ ppm: 1.37(9H,s), 3.68(3H,s), 5.07(1H,m), 6.11(1H,br), 7.80(1H,s)

A mixture of 206 mg of Compound 102 and 4.5 ml of 0.5N-sodium hydroxide was stirred for an hour at room temperature. The reaction solution was washed with ethyl acetate. The collected aqueous layer was acidified to pH 2.7 or less by addition of 1N-hydrochloric acid, saturated with sodium chloride and extracted with ethyl acetate. The combined organic layers were washed with a saturated saline solution, dried over sodium sulfate and distilled to afford 166 mg (85%) of Compound 103 as pale yellow foam.

IR$\nu_{max}^{neat}$cm$^{-1}$: 3400, 1740-1690, 1510, 1400.

$^1$H-NMR(CDCl$_3$)δ ppm: 1.39(9H,s), 4.76(1H,d,J=8Hz), 7.35(1H,d,J=8Hz), 8.38(1H,s)

A mixture of 262 mg of Compound 103 and 10 ml of 4N-hydrogen chloride-dioxane was stirred for an hour at room temperature and then distilled to remove the solvent. The residue was treated three times with ethyl ether by decantation and dried to obtain 161 mg of Compound 104 (hydrochloride) as colorless powders.

IR$\nu_{max}^{neat}$cm$^{-1}$: 3400, 1630, 1520, 1400.

$^1$H-NMR(D$_2$O)δ ppm: 4.91(1H,s), 8.49(1H,s)

SIMS(m/z): 159(M+H)$^+$

EXAMPLE 54

To a solution of 20.07 g of dimethyl N-Boc D-glutamate in 400 ml of anhydrous tetrahydrofuran was added 75 ml of 2.13 M-lithium diisopropylamide-hexane solution at −78° C. in argon atmosphere. The mixture was raised to −40° C. taking two hours, and then again cooled to −65° C. After adding 10.9 ml of isopropyl formate, the temperature of the mixture was raised to −20° C. taking 3 hours. Then, the mixture was stirred for 3 hours at −20° C., to which 28 ml of isopropanol was added. The resultant was diluted with 200 ml of ethyl ether-n-hexane (1:3) mixture and poured into a mixture of 219 ml of 1N-hydrochloric acid and 200 ml of water. The separated organic layer was extracted with 200 ml of 1% sodium carbonate aqueous solution. The combined aqueous layers were washed twice with 400 ml of ethyl acetate, adjusted to pH 2.6 with 3N-hydrochloric acid and saturated with sodium chloride. The resultant was extracted three times with 300 ml of ethyl acetate The combined organic layers were washed with 200 ml of a saturated saline solution, dried over anhydrous sodium sulfate and concentrated under reduced pressure to obtain 9.08 g of Compound 93 as pale yellow powders.

$^1$H-NMR(300MHz, CDCl$_3$)δ ppm: 1.5(9H,s×4), 2.10, 2.4-2.7, 3.0 (total 2H,m), 3.8(3H, s×3), 4.62(1H,dd×3), 6.98(1/3H,s)' 9.80(1/3H,s), 9.90(1/3H,s)

$^{13}$C-NMR(75MHz, CDCl$_3$)δ ppm: 20.50, 21.04, 23.71, 27.86, 27.93, 28.19, 52.67, 52.78, 54.48, 56.41, 56.92, 57.41, 57.67, 83.97, 84.60, 102.46, 156.90, 166.21, 171.40, 193.96, 195.68

EXAMPLE 55

To a mixture of 9.08 g of Compound 93 and 180 ml of 10% water-dioxane was added 2.87 g of hydroxylamine·hydrochloride, followed by stirring for 2 hours at room temperature. The reaction solution was diluted with 500 ml of ethyl acetate, washed with 200 m of water three times and with 200 ml of a saturated saline solution, dried over anhydrous sodium sulfate and then concentrated under reduced pressure to obtain 8.17 g of Compound 94.

To a solution of 8.17 g of Compound 94 in 30 ml of methanol was added 130 ml of water and 2.64 g of sodium hydroxide, followed by stirring for 2 hours at room temperature. After removing methanol under reduced pressure, the aqueous layer was diluted with 130 ml of water, adjusted to pH 8.8 and then washed twice with 100 ml of ethyl acetate. Then, it was adjusted to pH 2.6 and extracted three times with 120 ml of ethyl acetate. The combined ethyl acetate layers were washed with 120 ml of a saturated saline solution, dried over anhydrous sodium sulfate and concentrated under reduced pressure to obtain 7.34 g of Compound 71 as pale yellow powders.

$^1$H-NMR(300MHz, DMSO-d$_6$)δ ppm: 1.37(9H,s), 2.44(1H,dd,J=15, 9.5Hz), 2.57(1H,dd,J=15, 5Hz), 4.02(1H,dd,J=9.5, 5Hz), 7.05(1H,d,J=8Hz), 8.22(1H,s)

$^{13}$C-NMR(75MHz, DMSO-d$_6$)δ ppm: 23.83(CH2), 28.10(CH3), 52.88(CH), 78.07(q), 111.04(q), 151.93(CH), 155.32(q), 170.19(q), 173.19(q)

Amino acid analysis: D/L =6.76/1.17

EXAMPLE 56

A solution of 7.34 g of Compound 71 in 9 ml of trifluoroacetic acid was allowed to stand for 30 minutes at room temperature and concentrated to dryness. The residue was pulverized by ethyl ether to obtain 6.45 g of trifluoroacetate of Compound 72 as pale yellow powders. The powders (6.3 g) were dissolved in 200 ml of water and adjusted to pH 7 by addition of 3N-sodium hydroxide. The solution was passed through an active carbon column (50 ml), which was washed with 250 ml of water. The effluent and washing were combined and passed through a cellulose powder column (0.5 l) eluting 1.5 l of 15% aqueous acetonitrile, 3.0 l of 20% aqueous acetonitrile and then 1.5 l of 30% aqueous acetonitrile. Upon analysis of each fractions by high liquid chromatography, fractions showing a single peak were concentrated and freeze-dried to obtain 2.51 g of sodium salt of Compound 72 as pale yellow powders.

$^1$H-NMR(300MHz, D$_2$O)δ ppm: 2.70(1H,dd,J=15.5, 7.2Hz), 2.80(1H,dd,J=15.5, 4.5Hz), 3.87(1H,dd,J=7.2, 4.5Hz), 7.98(1H,s)

$^{13}$C-NMR(75MHz, D$_2$O)δ ppm: 28.51(CH2), 58.46(CH), 82.90(q), 158.53(CH), 177.13(q), 180.57(q)

IR(KBr)cm$^{-1}$: 3420, 3060, 1630, 1500, 1410, 1350, 1180, 1070, 920, 860, 810, 740, 660, 600, 520.

$[α]_D^{26}$ +55.3° (C: 0.50, in water)

UV:$λ_{max}^{H2O}$ 253 nm (E$_{1cm}^{1\%}$ 385)

Elementary analysis (C$_6$H$_7$N$_2$O$_4$Na·1.3H$_2$O) calculated: C; 33.13, H; 4.45, N; 12.88, Na; 10.57., found: C; 33.24, H; 4.55, N; 12 88, Na; 8.7

EXAMPLES 57–68

By the method of Example 37, Compound 9 was condensed with amino acid derivatives or amines and subjected to removal of protecting group, to afford Compound 105-135, 142-144 shown in Table 12.

TABLE 12

| Example No. | Starting compound | Reagent | Product |
|---|---|---|---|
| 57 | Compound 9 (1.0 g) ethyl 4-aminobutyrate. hydrochloride (0.62 g) | DEPC (0.66 ml) triethylamine (0.98 ml) | Compound 105 (0.25 g) $^1$H-NMR(d$_6$-DMSO)δ ppm: 1.18(3H,t,J=7Hz), 1.37(9H,s), 2.21-2.41(4H,m), 3.02-3.21(2H,m), 3.29-3.49(2H,m), 3.74-3.89(1H,m), 4.03(2H,q,J=7Hz), 7.21-7.29(1H,m), 7.56(1H,s), 7.68-7.81(1H,m) |
| | Compound 105 (0.24 g) | 0.5N sodium hydroxide solution (3.5 ml) | Compound 106 (0.19 g) SIMS(m/z):358(M + H)$^+$ |
| | Compound 106 (0.18 g) | 4N hydrogen chloride-dioxane (10 ml) | Compound 107 (hydrochloride) (0.13 g) $^1$H-NMR(D$_2$O)δ ppm: 1.77(2H,m), 2.36(2H,t,J=6.2Hz), 2.85(2H,d,J=6.6Hz), 3.18-3.39(2H,m), 4.09(1H,t,J=6.6Hz), 8.32(1H,s) SIMS(m/z):258(M + H)$^+$ |
| 58 | Compound 9 (1.0 g) ethyl 5-amino-valerate. hydrochloride (0.67 g) | DEPC (0.66 ml) triethylamine (0.98 ml) | Compound 108 (0.30 g) $^1$H-NMR(d$_6$-DMSO)δ ppm: 1.18(3H,t,J=7Hz), 1.36(9H,s), 1.37-1.70(2H,m), 2.21-2.42(4H,m), 3.02-3.19(2H,m), 3.74-3.88(1H,m), 4.04(2H,q,J=7Hz), 7.04-7.08(1H,m), 7.59(1H,s), 7.62-7.64(1H,m) |
| | Compound 108 (0.29 g) | 0.5N sodium hydroxide solution (4 ml) | Compound 109 (0.24 g) SIMS(m/z):372(M + H)$^+$ |
| | Compound 109 (0.24 g) | 4N hydrogen chloride-dioxane (10 ml) | Compound 110 (hydrochloride) (0.18 g) $^1$H-NMR(D$_2$O)δ ppm: 1.42-1.68(4H,m), 2.31-2.48(2H,m), 2.88(2H,d,J=6.6Hz), 3.09-3.38(2H,m), 4.08(1H,t,J=6.6Hz), 8.31(1H,s) SIMS(m/z):272(M + H)$^+$ |
| 59 | Compound 9 (1 g) (S)-α-amino-benzylamine (0.47 ml) | DEPC (0.66 ml) triethylamine (0.51 ml) | Compound 113 (0.63 g) $^1$H-NMR(d$_6$-DMSO)δ ppm: 1.31-1.49(12H,m), 2.21-2.51(2H,m), 3.79-3.97(1H,m), 4.80-4.99(1H,m), 7.12-7.41(5H,m), 7.57(1H,s), 7.79-8.02(1H,m) |
| | Compound 113 (0.62 g) | 4N hydrogen chloride (25 ml) | Compound 114 (hydrochloride) (0.55 g) $^1$H-NMR(D$_2$O)δ ppm: 1.47(3H,d,J=7.4Hz), 2.71(2H,d,J=6.6Hz), 3.68-3.87(1H,m), 4.09(1H,t,J=6.6Hz), 7.27-7.42(5H,m), 7.52(1H,s), SIMS(m/z):276(M + H)$^+$ |
| 60 | Compound 9 (1.0 g) 4-phenyl-piperazine (0.56 ml) | DEPC (0.66 ml) triethylamine (0.51 ml) | Compound 111 (0.64 g) $^1$H-NMR(d$_6$-DMSO)δ ppm: 1.36(9H,s), 2.21-2.44(2H,m), 2.93-3.21(4H,m), 3.52-3.78(4H,m), 4.35-4.51(1H,m), 6.73-7.03(3H,m), 7.14-7.30(2H,m), 7.57(1H,s) |
| | Compound 111 (0.62 g) | 4N hydrogen chloride-dioxane (30 ml) | Compound 112 (hydrochloride) (0.55 g) $^1$H-NMR(D$_2$O)δ ppm: 2.71-2.90(2H,m), 2.97-3.98(8H,m), 4.58-4.70(1H,m), 7.07-7.21(3H,m), 7.34-7.49(2H,m), 7.97(1H,s) SIMS(m/z):317(M + H)$^+$ |
| 61 | Compound 9 | DEPC | Compound 115 |

TABLE 12-continued

| Example No. | Starting compound | Reagent | Product |
|---|---|---|---|
| | (1.1 g) methyl (S)-β-amino-α-tert-butoxy-carbonylamino-propionate (0.78 g) | (0.73 ml) triethylamine (0.56 ml) | (0.76 g) $^1$H-NMR(d$_6$-DMSO)δ ppm: 1.38(18H,s), 2.22-2.41(2H,m), 3.22-3.52(2H,m), 3.61(3H,s), 3.70-3.81(1H,m), 3.92-4.10(1H,m), 7.08-7.18(1H,m), 7.31-7.40(1H,m), 7.58(1H,s), 7.81-7.86(1H,m) |
| | Compound 115 (0.72 g) | 0.5N sodium hydroxide solution (9.4 ml) | Compound 116 (0.58 g) $^1$H-NMR(d$_6$-DMSO)δ ppm: 1.36(18H,s), 2.22-2.47(2H,m), 3.22-3.57(2H,m), 3.97-4.08(2H,m), 6.82(1H,d,J=7.8Hz), 6.98(1H,d,J=7.8Hz), 7.86-7.99(1H,m), 8.17(1H,s) |
| | Compound 116 (0.55 g) | 4N hydrogen chloride-dioxane (20 ml) | Compound 117 (hydrochloride) (0.41 g) $^1$H-NMR(D$_2$O)δ ppm: 2.89(2H,d,J=6.2Hz), 3.69-3.85(2H,m), 4.02-4.11(1H,m), 4.18(1H,t,J=6.2Hz), 8.36(1H,s) SIMS(m/z):259(M + H)$^+$ |
| 62 | Compound 9 (1.1 g) methyl (R)-β-amino-α-tert-butoxy-carbonylamino-propionate (0.78 g) | DEPC (0.73 ml) triethylamine (0.56 ml) | Compound 118 (0.70 g) $^1$H-NMR(d$_6$-DMSO)δ ppm: 1.37(18H,s), 2.22-2.41(2H,m), 3.22-3.48(2H,m), 3.62(3H,s), 3.74-3.81(1H,m), 3.95-4.10(1H,m), 7.08(1H,d,J=7.6Hz), 7.19-7.25(1H,m), 7.58(1H,s), 7.80-7.86(1H,m) |
| | Compound 118 (0.68 g) | 0.5N sodium hydroxide solution (8.8 ml) | Compound 119 (0.60 g) $^1$H-NMR(d$_6$-DMSO)δ ppm: 1.36(18H,s), 2.27-2.42(2H,m), 3.22-3.51(2H,m), 3.93-4.08(2H,m), 6.82(1H,d,J=7.8Hz), 6.99(1H,d,J=7.8Hz), 7.91-8.01(1H,m), 8.16(1H,s) |
| | Compound 119 (0.58 g) | 4N hydrogen chloride-dioxane (20 ml) | Compound 120 (hydrochloride) (0.40 g) $^1$H-NMR(D$_2$O)δ ppm: 2.77(2H,d,J=6.2Hz), 3.58-3.59(2H,m), 3.82-3.93(1H,m), 4.08(1H,t,J=6.2Hz), 8.02(1H,s) SIMS(m/z):259(M + H)$^+$ |
| 63 | Compound 9 (0.9 g) methyl 4-aminomethyl-benzoate.hydrochloride (0.60 g) | DEPC (0.59 ml) triethylamine (0.92 ml) | Compound 121 (0.61 g) $^1$H-NMR(d$_6$-DMSO)δ ppm: 1.39(9H,s), 2.44(2H,d,J=6Hz), 3.84(3H,s), 3.88-3.97(1H,m), 4.31-4.34(2H,m), 7.28(2H,d,J=8Hz), 7.56(1H,s), 7.62-7.79(1H,m), 7.85(2H,d,J=8Hz) |
| | Compound 121 (0.59 g) | 0.5N sodium hydroxide solution (8 ml) | Compound 122 (0.52 g) $^1$H-NMR(d$_6$-DMSO)δ ppm: 1.38(9H,s), 2.43-2.57(2H,m), 3.97-4.18(1H,m), 4.34(2H,d,J=5.8Hz), 7.05(1H,d,J=7.4Hz), 7.32(2H,d,J=8Hz), 7.87(2H,d,J=8Hz), 8.20(1H,s), 8.47-8.52(1H,m) |
| | Compound 122 (0.50 g) | 4N hydrogen chloride-dioxane (20 ml) | Compound 123 (hydrochloride) (0.38 g) $^1$H-NMR(D$_2$O)δ ppm: 2.76-2.87(2H,m), 4.12-4.23(1H,m), 4.35(1H,d,J=15.4Hz), 4.56(1H,d,J=15.4Hz), 7.37(2H,d,J=8Hz), 7.96-8.01(3H,m) SIMS(m/z):306(M + H)$^+$ |
| 64 | Compound 9 (1.0 g) ethyl 4-piperidine-carboxylate (0.57 ml) | DEPC (0.66 ml) triethylamine (0.51 ml) | Compound 124 (0.65 g) $^1$H-NMR(d$_6$-DMSO)δ ppm: 1.19(3H,t,J=7Hz) 1.35(9H,s), 1.22-1.50(1H,m), 1.69-1.89(2H,m), 2.17-3.19(6H,m), 3.99-4.43(5H,m), 6.98(1H,d,J=7.6Hz), 7.60(1H,s) |
| | Compound 124 (0.63 g) | 0.5N sodium hydroxide solution (8.8 ml) | Compound 125 (0.27 g) $^1$H-NMR(d$_6$-DMSO)δ ppm: 1.36(9H,s), 1.18-1.50(1H,m), 1.72-1.88(2H,m), 2.31-2.84(4H,m), 3.21-3.39(2H,m), 3.81-4.52(3H,m), 7.88-8.03(1H,m), 8.30(1H,s) |
| | Compound 125 (0.25 g) | 4N hydrogen chloride-dioxane (15 ml) | Compound 126 (hydrochloride) (0.17 g) $^1$H-NMR(D$_2$O)δ ppm: 1.31-1.71(1H,m), 1.92-2.11(2H,m), 2.61-3.35(6H,m), 3.61-4.02(2H,m), 4.21-4.35(1H,m), 8.37(1H,s) SIMS(m/z):284(M + H)$^+$ |
| 65 | Compound 9 (1.0 g) methyl 3-piperidine-carboxylate.hydrochloride (0.66 g) | DEPC (0.66 ml) triethylamine (0.98 ml) | Compound 127 (0.46 g) $^1$H-NMR(d$_6$-DMSO)δ ppm: 1.21-2.08(5H,m), 1.35(9H,s), 2.29-2.91(3H,m), 3.25-3.48(2H,m), 3.62(3H,s), 3.82-4.01(1H,m), 4.35-4.59(1H,m), 6.97-7.09(1H,m), 8.12(1H,s) |
| | Compound 127 (0.44 g) | 0.5N sodium hydroxide solution (6.3 ml) | Compound 128 (0.33 g) $^1$H-NMR(d$_6$-DMSO)δ ppm: 1.21-2.09(5H,m), 1.35(9H,s), |

TABLE 12-continued

| Example No. | Starting compound | Reagent | Product |
|---|---|---|---|
| | | | 2.17–2.45(3H,m), 2.63–3.53(2H,m), 3.81–4.15(1H,m), 4.31–4.59(1H,m), 6.82–7.10(1H,m), 8.22(1H,s) |
| | Compound 128 (0.31 g) | 4N hydrogen chloride-dioxane (15 ml) | Compound 129 (hydrochloride) (0.22 g) $^1$H-NMR(D$_2$O)δ ppm: 1.49–2.08(5H,m), 2.61–2.98(3H,m), 3.31–4.21(4H,m), 8.34(1H,s) SIMS(m/z):284(M + H)$^+$ |
| 66 | Compound 9 (2.0 g) methyl 2-piperidine-carboxylate. hydrochloride (1.3 g) | DEPC (1.3 ml) triethylamine (2.0 ml) | Compound 130 (0.31 g) $^1$H-NMR(d$_6$-DMSO)δ ppm: 1.32–1.69(5H,m), 1.36(9H,s), 2.07–2.63(4H,m), 3.20–3.51(1H,m), 3.62(3H,s), 3.91–4.22(2H,m), 6.71–6.86(1H,m), 7.56(1H,s) |
| | Compound 130 (0.3 g) | 0.75N sodium hydroxide solution (3.5 ml) | Compound 131 (0.25 g) $^1$H-NMR(d$_6$-DMSO)δ ppm: 1.31–1.72(5H,m), 1.37(9H,s), 2.08–2.71(4H,m), 3.17–3.42(1H,m), 3.88–4.11(2H,m), 7.04(1H,d,J=7.6Hz), 8.22(1H,s) |
| | Compound 131 (0.23 g) | 4N hydrogen chloride-dioxane (10 ml) | Compound 132 (hydrochloride) (0.17 g) $^1$H-NMR(D$_2$O)δ ppm: 1.28–1.81(5H,m), 2.19–2.40(1H,m), 2.61–2.99(3H,m), 3.21–3.41(1H,m), 3.58–3.89(1H,m), 4.13–4.22(1H,m), 8.33(1H,s) SIMS(m/z):284(M + H)$^+$ |
| 67 | Compound 9 (1.0 g) methyl (S)-2-amino-3-(p-hydroxyphenyl) propionate. hydrochloride (0.85 g) | DEPC (0.66 ml) triethylamine (0.98 ml) | Compound 133 (0.70 g) $^1$H-NMR(d$_6$-DMSO)δ ppm: 1.35(9H,s), 2.12–2.43(2H,m), 2.77–2.93(2H,m), 3.56(3H,s), 3.79–4.01(1H,m), 4.35–4.51(1H,m), 6.63(2H,d,J=7.4Hz), 6.92(2H,d,J=7.4Hz), 7.43(1H,d,J=7.2Hz), 7.55(1H,s), 7.76(1H,d,J=7.2Hz), 9.24(1H,s) |
| | Compound 133 (0.68 g) | 0.5N sodium hydroxide solution (8.6 ml) | Compound 134 (0.55 g) $^1$H-NMR(d$_6$-DMSO)δ ppm: 1.36(9H,s), 2.19–2.46(2H,m), 2.73–2.95(2H,m), 3.98–4.09(1H,m), 4.29–4.40(1H,m) 6.65(2H,d,J=8.4Hz), 6.89(1H,d,J=8Hz), 6.99(2H,d,J=8.4Hz), 7.91(1H,d,J=8Hz), 8.10(1H,s), 9.21(1H,s) |
| | Compound 134 (0.53 g) | 4N hydrogen chloride-dioxane (20 ml) | Compound 135 (hydrochloride) (0.40 g) $^1$H-NMR(D$_2$O)δ ppm: 2.74(2H,d,J=6.2Hz), 2.91–3.30(2H,m), 4.10–4.24(1H,m), 4.59–4.68(1H,m), 6.82(2H,d,J=8.4Hz), 7.17(2H,d,J=8.4Hz), 8.24(1H,s) SIMS(m/z):336(M + H)$^+$ |
| 68 | Compound 140 (0.47 g) methyl (R)-α-amino(p-hydroxyphenyl) propionate. hydrochloride (0.21 g) | DEPC (0.17 ml) triethylamine (0.26 ml) | Compound 142 (0.48 g) $^1$H-NMR(d$_6$-DMSO)δ ppm: 1.38(18H,s), 2.38–2.91(6H,m), 3.01–3.20(2H,m), 3.29–3.42(2H,m), 3.56(3H,s), 3.96–4.21(2H,m), 4.23–4.41(1H,m), 6.63(2H,d,J=8.4Hz), 6.92(2H,d,J=8.4Hz), 7.08–7.19(1H,m), 7.58(1H,s), 8.06(1H,d,J=8Hz), 8.73–8.90(1H,m), 9.23(1H,s) |
| | Compound 142 (0.45 g) | 0.5N sodium hydroxide solution (4 ml) | Compound 143 (0.33 g) $^1$H-NMR(d$_6$-DMSO)δ ppm: 1.38(18H,s), 2.39–2.90(6H,m), 3.01–3.18(2H,m), 3.27–3.41(2H,m), 3.97–4.21(2H,m), 4.29–4.45(1H,m), 6.68(2H,d,J=8.4Hz), 6.78–6.93(1H,m), 6.98(2H,d,J=8.4Hz), 7.09–7.25(1H,m), 7.99–8.18(1H,m), 8.31(1H,s), 9.19(1H,s) |
| | Compound 143 (0.31 g) | 4N hydrogen chloride-dioxane (20 ml) | Compound 144 (hydrochloride) (0.23 g) $^1$H-NMR(D$_2$O)δ ppm: 2.58–2.91(6H,m), 2.96–3.30(4H,m), 4.13–4.34(2H,m), 4.43–4.64(1H,m), 6.79(2H,d,J=8.4Hz), 7.10(2H,d,J=8.4Hz), 8.15(1H,s) SIMS(m/z):482(M + H)$^+$ |

EXAMPLE 69

Compounds 136 to 138 shown in Table 13 were obtained by the condensation of Compound 12 (hydrochloride) and an amino acid derivative, followed by the removal of the protecting group in accordance with the method of Example 33.

TABLE 13

| Example No. | Starting compound | Reagent | Product |
|---|---|---|---|
| 69 | Compound 12 (hydro-chloride) | N-hydroxy-5-norbornene-2,3-dicarbo- | Compound 136 (0.12 g) $^1$H-NMR(d$_6$-DMSO)δ ppm: |

TABLE 13-continued

| Example No. | Starting compound | Reagent | Product |
|---|---|---|---|
| | (0.67 g) (S)-$N^{\alpha}$-tert-butoxy-carbonyl-$\beta$-[N-(E)-3-carbamoyl-acryloyl] aminoalanine (0.6 g) | ximide (HONB) (0.36 g) dicyclohexyl-carbodiimide (0.45 g) triethylamine (0.87 ml) | 1.38(9H,s), 2.39–2.63(2H,m), 3.21–3.47(2H,m), 3.62(3H,s), 4.01–4.29(1H,m), 4.31–4.49(1H,m), 6.76–6.89(3H,m), 7.29(1H,bs), 7.78(1H,bs), 8.25(1H,s), 8.38(2H,bs) |
| | Compound 136 (0.10 g) | 0.5N sodium hydroxide solution (2.6 ml) | Compound 137 (0.02 g) SIMS(m/z):456(M + H)+ |
| | Compound 137 (0.019 g) | 4N hydrogen chloride-dioxane (5 ml) | Compound 138 (hydrochloride) (7 mg) $^1$H-NMR(D$_2$O)$\delta$ ppm: 2.69–2.92(2H,m), 3.71–3.97(2H,m), 4.18–4.30(1H,m), 4.58–4.70(1H,m), 6.78–6.99(2H,m), 8.32(1H,s), SIMS(m/z):356(M + H)+ |

EXAMPLE 70

Compounds 139 to 141 shown in Table 14 were obtained by the condensation of Compound 12 (hydrochloride) and an amino acid derivative, followed by the removal of the protecting group, in accordance with the method of Example 28.

TABLE 14

| Example No. | Starting compound | Reagent | Product |
|---|---|---|---|
| 70 | Compound 12 (hydrochloride) (0.67 g) (R)-$N^{\alpha}$-tert-butoxy-carbonyl-$\beta$-(2-tert-butoxy-carbonyl-aminoethyl) thioalanine | N-methyl-morpholine (0.23 ml) isobutyl chloroformate (0.27 ml) triethylamine (0.87 ml) | Compound 139 (0.44 g) $^1$H-NMR(d$_6$-DMSO)$\delta$ ppm: 1.39(18H,s), 2.38–2.91(4H,m), 3.02–3.20(2H,m), 3.31–3.42(2H,m), 3.57(3H,s), 4.02–4.30(2H,m), 6.79–6.99(2H,m), 7.56(1H,s), 9.12–9.23(1H,m) |
| | Compound 139 (0.70 g) | 0.5N sodium hydroxide solution (6.2 ml) | Compound 140 (0.61 g) $^1$H-NMR(d$_6$-DMSO)$\delta$ ppm: 1.38(18H,s), 2.43–2.89(4H,m), 3.01–3.22(2H,m), 3.24–3.48(2H,m), 3.99–4.17(1H,m), 4.28–4.41(1H,m), 6.23–7.02(2H,m), 8.18(1H,d,J=7.4Hz), 8.25(1H,s) |
| | Compound 140 (0.59 g) | 4N hydrogen chloride-dioxane (20 ml) | Compound 141 (hydrochloride) (0.43 g) $^1$H-NMR(D$_2$O)$\delta$ ppm: 2.71–2.99(4H,m), 3.02–3.32(4H,m), 4.21–4.32(1H,m), 4.59–4.68(1H,m), 8.30(1H,s) |

TABLE 14-continued

| Example No. | Starting compound | Reagent | Product |
|---|---|---|---|
| | | | SIMS(m/z):319(M + H)+ |

EXAMPLE 71

To a solution of Compound 140 (0.73 g) in methylene chloride (15 ml) was added m-chloroperbenzoic acid (0.27 g) under stirring and ice cooling. After stirring for 30 minutes under ice cooling, the reaction mixture was subjected to a silica gel column chromatography (2.5×30 cm; acetonitrile: water: methanol=3:3:1) to obtain Compound 145 (0.24 g) as colorless powders.

$^1$H-NMR(d$_6$-DMSO)$\delta$ ppm: 1.39(18H,s), 2.43–2.69(2H,m), 2.72–3.02(4H,m), 3.27–3.48(2H,m), 4.21–4.49(2H,m), 7.0–7.13(1H,m), 7.21–7.39(1H,m), 8.24(1H,s), 8.32–8.48(1H,m)

To a solution of Compound 145 (0.22 g) in acetic acid (3 ml) was added 4N-hydrogen chloride-dioxane (20 ml). After standing for an hour at room temperature, the solvent was distilled off under reduced pressure. The residue was washed twice with ethyl ether (20 ml) by decantation. The resulting precipitate was dried to obtain hydrochloride of Compound 146 (0.16 g) as colorless powders.

$^1$H-NMR(D$_2$O)$\delta$ ppm: 2.71–2.99(4H,m), 3.05–3.35(4H,m), 4.21–4.39(1H,m), 4.53–4.69(1H,m), 8.32(1H,s)

SIMS(m/z): 335(M+H)+

EXAMPLE 72

To a solution of dimethyl (R)-N-tert-butoxycarbonylaspartate (5.23 g, 20 m mol) in tetrahydrofuran (100 ml) was added a solution of lithium diisopropylamide in hexane (23%, 28.2 ml, 44 m mol) at −78° C. in a stream of nitrogen and the whole was stirred for 10 minutes at −78° C. The reaction mixture was stirred for 20 minutes at −40° C. The reaction solution was again cooled to −78° C., to which a solution of isopropyl formate (2.4 ml, 24 m mol) in tetrahydrofuran (4 ml) was added dropwise. After stirring for 10 minutes, the temperature of the reaction mixture was raised to −40° C. and stirring was continued until its internal temperature of −20° C. was attained. To the reaction mixture was added isopropyl alcohol (8 ml). The mixture was poured into a mixture of water and ethyl ether and the resultant was extracted with water. The resulting aqueous layers were combined and acidified to pH 2 with 1N hydrochloric acid. After saturating with NaCl, the resultant was extracted with ethyl acetate. The organic layer was washed with a saturated NaCl solution, dried over anhydrous Mg$_2$SO$_4$ and distilled under reduced pressure. The residue was subjected to a silica gel column chromatography (2.5×40 cm; ethyl acetate:hexane=1:1) to obtain the desired compound, dimethyl (R)-N-tert-butoxycarbonyl-3- formyl-asparatate (1.16 g, 20%), as colorless oil.

IR$\nu_{max}^{neat}$cm$^{-1}$: 3350, 2990, 1760–1660, 1500, 1440, 1400.

$^1$H-NMR(CDCl$_3$)$\delta$ ppm: 1.45(9H,s), 3.60–4.00(1H,m), 3.69–3.83(6H,m), 4.83–5.11(1H,m), 6.03(1H,m), 7.72(0.33H,s), 9.83(0.33H,s), 9.84(0.33H,s).

To a solution of the above product (1.16 g) in a mixture of dioxane (10 ml) and water (4 ml) was added hydroxylamine hydrochloride (0.31 g, 4.4 m mol), followed by stirring for an hour at room temperature. Ethyl acetate (50 ml) was added to the reaction mixture, and the organic layer was washed successively with water and saturated NaCl solution and dried (sodium sulfate). After distilling the solvent off, the residue was dissolved in methanol (35 ml) to which 0.5N sodium hydroxide solution (8 ml) was added. After stirring for an hour, the reaction solution was acidified to pH 2 by addition of 1N hydrochloric acid, saturated with NaCl and extracted with ethyl acetate. The extract was distilled off, and the residue was subjected to a silica gel column chromatography (2.5×40 cm; ethyl acetate-→ethyl acetate: methanol=9:1→4:1) to obtain Compound 147 (0.58 g, 53%) as pale yellow foam.

IR$\nu_{max}^{neat}$cm$^{-1}$: 3400, 3000, 1750-1680, 1630, 1590, 1510, 1440.

$^1$H-NMR(CDCl$_3$)δ ppm: 1.45(9H,s), 3.82(3H,s), 5.13(1H,m), 5.96(1H,bs), 8.02(1H,s).

0.5N Sodium hydroxide solution (13 ml) was added to Compound 147 (0.58 g) and the mixture was stirred for an hour at room temperature. The reaction solution was washed with ethyl acetate. The aqueous layer was acidified to pH 2.7 with 1N hydrochloric acid, saturated with NaCl and extracted with ethyl acetate. The organic layers were combined, washed with a saturated NaCl solution and dried over anhydrous sodium sulfate. The solvent was distilled off to obtain Compound 148 (0.40 g, 72%) as pale yellow foam.

IR$\nu_{max}^{KBr}$cm$^{-1}$: 3400, 1740-1690, 1510, 1400, 1370.

$^1$H-NMR(d$_6$-DMSO)δ ppm: 1.39(9H,s), 4.76(1H,d,J=8Hz), 7.35(1H,d,J=8Hz), 8.83(1H,s), 4N-Hydrogen chloride-dioxane solution (9 ml) was added to Compound 148 (0.40 g), followed by stirring for an hour at room temperature. The solvent was distilled off under reduced pressure. The residue was washed three times with ethyl ether by decantation. The resulting precipitate was dried to obtain hydrochloride of Compound 149 (0.30 g, 75%) as colorless powders.

IR$\nu_{max}^{KBr}$cm$^{-1}$: 3400, 1640, 1520, 1400.

$^1$H-NMR(D$_2$O)δ ppm: 4.91(1H,s), 8.49(1H,s).

SIMS(m/z) 159(M+H)+

EXAMPLE 73

A solution of lithium diisopropylamide in hexane (23%, 20ml, 31 m mol) was added to a solution of methyl (RS)-N-tert-butoxycarbonyl-6-piperidone-2-carboxylate (4.65 g, 18 m mol) in tetrahydrofuran at −78° C. in a stream of nitrogen and the resultant was stirred for 10 minutes. To the reaction mixture was added dropwise a solution of N-acetylimidazole (2.38 g, 21.6 m mol) in tetrahydrofuran (30 ml). After stirring for 10 minutes at −78° C., the temperature of the reaction mixture was raised to −40° C. Stirring was continued until the internal temperature reached −20° C. After adding a saturated ammonium chloride solution, the reaction mixture was extracted with ethyl acetate. The extract was washed with saturated NaCl solution, dried over sodium sulfate and distilled off under reduced pressure. The residue was subjected to a silica gel column chromatography (2.5×40 cm; ethyl acetate: hexane=1:1-2:1) to obtain methyl (RS)-N-tert-butoxycarbonyl-5-acetyl-6-piperidone-2-carboxylate (1.05 g, 20%) as colorless oil.

IR$\nu_{max}^{neat}$cm$^{-1}$: 2980, 1780, 1760, 1720, 1620, 1470, 1440, 1370.

$^1$H-NMR(CDCl$_3$)δ ppm: 1.51(9H,s), 1.90-2.60(5H,m), 2.00(3H,s), 3.77(3H,s), 4.81(1H,m).

To a solution of the above product (1.05 g, 3.51 m mol) in a mixture of 1,4-dioxane (6 ml) and water (10 ml) was added hydroxylamine hydrochloride (0.27 g, 3.86 m mol), followed by stirring for 2 hours at room temperature. 0.5N Sodium hydroxide solution (7.7 ml) was added to the reaction mixture. The mixture was stirred for an hour, acidified with 1N hydrochloric acid (to pH 2.5) and then extracted with ethyl acetate. The extract was washed successively with water and saturated NaCl solution, dried over sodium sulfate, and distilled off under reduced pressure to remove the solvent. The residue was subjected to a silica gel column chromatography (2.5×40 cm; ethyl acetate: hexane=1:1 →ethyl acetate→ethyl acetate:methanol= 9:1) to obtain Compound 150 (0.413 g, 37%) as pale yellow oil.

IR$\nu_{max}^{neat}$cm$^{-1}$: 3350, 2990, 1750, 1720, 1670, 1620, 1510, 1440.

$^1$H-NMR(CDCl$_3$)δ ppm: 1.45(9H,s), 2.15(3H,s), 1.60-2.20(4H,m), 3.77(3H,s), 4.35(1H,m), 5.20(1H,b).

0.5N Sodium hydroxide solution (7.9 ml) was added to Compound 150 (0.413 g, 1.31 m mol) and the mixture was stirred for 2 hours as room temperature. The reaction solution was washed with ethyl acetate. The aqueous layer was taken and acidified with 1N hydrochloric acid (pH 2.7), saturated with NaCl and extracted with ethyl acetate. The extract was washed with a saturated NaCl solution and dried over sodium sulfate. The solvent was distilled off under reduced pressure to obtain Compound 151 (0.38 g, 97%) as pale yellow foam.

IR$\nu_{max}^{KBr}$cm$^{-1}$: 3300, 1740-1670, 1600, 1510.

$^1$H-NMR(CDCl$_3$)δ ppm: 1.45(9H,s), 2.18(3H,s), 2.04(2H,m), 2.37(2H,m), 4.25(1H,m), 5.60(1H,d,J=7Hz).

4N Hydrogen chloride-dioxane solution (4 ml) was added to Compound 151 (0.38 g, 1.27 m mol) and the mixture was stirred for an hour at room temperature. The solvent was distilled off. The residue was washed three times with ethyl ether by decantation and dried to obtain Compound 152 hydrochloride (0.34 g, 80%) as colorless powders.

IR$\nu_{max}^{KBr}$cm$^{-1}$: 3420, 2940, 1720, 1640, 1500, 1450.

$^1$H-NMR(D$_2$O)δ ppm: 2.23(3H,s), 2.15(2H,m), 2.43(2H,m), 4.05(1H,t,J=6Hz).

SIMS(m/z):201(M+H)+

EXAMPLE 74

A solution of lithium diisopropylamide (30.8%, 10.5 ml, 22 m mol) in hexane was added to a solution of dimethyl (R)-N-tert-butoxycarbonylaspartate (2.61 g, 10 m mol) in tetrahydrofuran (50 ml) at −78° C. in a stream of nitrogen and the mixture was stirred for 10 minutes at −78° C. After stirring for 20 minutes at −40° C., the reaction mixture was again cooled to −78° C., to which a solution of acetylimidazole (1.32 g, 12 m mol) in tetrahydrofuran (15 ml) was added dropwise. After stirring the reaction mixture for 10 minutes, a saturated ammonium chloride solution was added and the resulting mixture was stirred at room temperature. The resultant was diluted with water and extracted with ethyl acetate. The organic layer was washed with a saturated NaCl solution, dried over sodium sulfate and distilled off under reduced pressure to remove the solvent. The residue was subjected to a silica gel column chromatography (2.5×40 cm; ethyl acetate: hexane=1:3) to obtain dimethyl (R)-N-tert-butoxycarbonyl-3-acetylaspartate (1.16 g, 38%) as colorless oil.

IRν$_{max}$$^{neat}$cm$^{-1}$: 3390, 2980, 1760–1720, 1500, 1420, 1390, 1370.

$^1$H-NMR(CDCl$_3$)δ ppm: 1.44(9H,s), 2.30(1.5H,s), 2.34(1.5H,s), 3.75, 3.77(6H,s), 4.26(1H,m), 4.97(1H,m), 5.56(1H,m).

To a solution of the above product (0.994 g, 3.28 m mol) in a mixture of 1,4-dioxane (6 ml) and water (2 ml) was added hydroxylamine hydrochloride (0.251 g, 3.61 m mol), and the resultant was stirred for 2 hours at room temperature. To the reaction mixture was added 0.5N sodium hydroxide solution (7.2 ml), and the resultant was stirred for an hour. The reaction mixture was acidified to pH 2.0 with 1N hydrochloric acid, saturated with NaCl and extracted with ethyl acetate. The extract was washed with a saturated NaCl solution and dried over sodium sulfate. The solvent was distilled off under reduced pressure and the residue was subjected to a silica gel column chromatography (2.5×40 cm; ethyl acetate→ethyl acetate: methanol=9:1) to obtain Compound 153 (0.3 g, 32%) as pale yellow foam.

IRν$_{max}$$^{neat}$cm$^{-1}$: 3400, 2990, 1750, 1710, 1630, 1510, 1430.

$^1$H-NMR(CDCl$_3$)δ ppm: 1.37(9H,s), 1.96(3H,s), 3.65(3H,s), 4.86(1H,m), 6.28(1H,m).

To Compound 153 (0.3 g, 1.05 m mol) was added 0.5N sodium hydroxide solution (6.3 ml) and the resultant was stirred for an hour at room temperature. The reaction mixture was washed with ethyl acetate. The aqueous layer was acidified to pH 2.7, saturated with NaCl and extracted with ethyl acetate. The extract was washed with a saturated NaCl solution and dried over sodium sulfate. The solvent was distilled off under reduced pressure to obtain Compound 154 (0.101 g, 35%) as pale yellow foam.

IRν$_{max}$$^{neat}$cm$^{-1}$: 3340, 3200, 1750, 1680, 1650, 1570, 1510, 1450.

$^1$H-NMR(d -DMSO)δ ppm: 1.39(9H,s), 2.11(3H,s), 4.77(1H,d,J=7.2Hz), 7.13(1H,d,J=7.2Hz).

To Compound 154 (0.096 g, 0.35 m mol) was added 4N hydrogen chloride-dioxane (4 ml), and the resultant was stirred for an hour at room temperature, and distilled off to remove the solvent. The residue was washed three times with ethyl ether by decantation. The precipitate was dried to obtain Compound 155 hydrochloride (0.083 g, 88%) as colorless powders.

IRν$_{max}$$^{KBr}$cm$^{-1}$: 3430, 2900, 1740, 1710, 1580, 1500.

$^1$H-NMR(D$_2$O)δ ppm: 2.31(3H,s), 4.89(1H,s).

SIMS(m/z):173(M+H)$^+$

EXAMPLE 75

Hydrochloride of Compound 75 (1.1 gl was subjected to a column chromatography using an ion exchange resin of IR-120B (H$^+$type; 2.5 cm×40 cm). As eluents, water (1 l) and then 1% aqueous ammonia were used. Fractions which absorbed ultraviolet light and were positive to ninhydrin were collected. The resultant was concentrated and freeze-dried to obtain ammonium salt of Compound 75 (0.75 g) as pale yellow powders.

IRν$_{max}$$^{KBr}$cm$^{-1}$: 3430, 2950, 2930, 1620, 1500, 1400, 1340.

$^1$H-NMR(D$_2$O)δ ppm: 2.05(3H,s), 2.65(1H,dd,J=15.8Hz,7.4Hz), 2.81(1H,dd,J=15.8Hz,4.4Hz), 3.85(1H,dd,J=7.4Hz,4.4Hz).

SIMS(m/z): 187(M+H)$^+$

EXAMPLE 76

A solution of hydrochloride of Compound 75 (1.89 g) in water (22 ml) was adjusted to pH 3.5 with 0.1N sodium hydroxide solution, and the resultant was concentrated under reduced pressure. The concentrate was subjected to a cellulose column chromatography (Avicel®; 2.5×60 cm). As eluents, acetonitrile-water (87:13, 1 l) and then acetonitrile-water (80:20) were used. Fractions which absorbed ultraviolet light, were positive to ninhydrin and did not become turbid by addition an aqueous solution of silver nitrate were collected and the resultant was freeze-dried to obtain Compound 75 (0.695 g) as colorless powders.

IR$^{KBr}$cm$^{-1}$: 3400, 3000, 1620, 1520, 1440, 1410, 1340.

$^1$H-NMR(D$_2$O)δ ppm: 2.16(3H,s), 2.84(1H,dd,J=15.8Hz,5.2Hz), 2.84(1H,dd,J=15.8Hz,6.4Hz), 3.90(1H,dd,J=6.4Hz,5.2Hz).

SIMS(m/z): 187(M+H)$^+$

[α]$^{20}$ −36.7° (c=0.15, water)

EXAMPLE 77

To a solution of methyl (S)-N-tert-butoxycarbonylpyroglutamate (3.65 g) in tetrahydrofuran (40 ml) was added a solution of lithium diisopropylamide in hexane (24.2%; 11 ml) at −78° C. in a stream of nitrogen, and the resultant was stirred for 10 minutes at −78° C. Cyclopentanecarbaldehyde (1.5 g) was added dropwise to the reaction mixture, followed by stirring for 10 minutes at −78° C. To the reaction mixture was added a saturated ammonium chloride solution and stirring was continued until the temperature reached room temperature. The reaction mixture was extracted with ethyl acetate. The organic layer was washed successively with water and a saturated NaCl solution, dried over sodium sulfate and distilled off to remove the solvent. The residue was subjected to a silica gel column chromatography (2.5 cm×60 cm; ethyl acetate:hexane=1:3→1:2→1:1) to obtain methyl (S)-N-tert-butoxycarbonyl 4-(α-hydroxycyclopentylmethyl)pyroglutamate (2.46 g, 48%) as colorless oil.

IRν$_{max}$$^{neat}$cm$^{-l}$: 3500, 2960, 1780, 1750, 1480, 1430, 1370.

$^1$H-NMR(CDCl$_3$)δ ppm: 1.50(9H,m), 1.41–1.90(9H,m), 2.12–2.90(4H,m), 3.80(3H,s), 4.59(1H,m).

To dichloromethane (18 ml) was added a solution of oxalyl chloride (0.75 ml) and dimethyl sulfoxide (1.1 ml) in dichloromethane (2 ml), and the resultant was stirred for 2 minutes. A solution of methyl (S)-N-tert-butoxycarbonyl-4-(α-hydroxycyclopentylmethy)pyroglutamate (2.46 g) in dichloromethane (10 ml) was added to the reaction mixture over 5 minutes, followed by stirring for 15 minutes at −60° C. To the reaction mixture was added triethylamine (5 ml), and the resultant was stirred for 5 minutes and further stirred for an hour at room temperature. After the addition of water, the organic layer was taken, and the aqueous layer was extracted with dichloromethane. All of the organic layers were combined, washed with a saturated NaCl solution, dried over sodium sulfate and distilled off to remove the solvent. The residue was subjected to a silica gel column chromatography (2.5 cm×40 cm; ethyl acetate:hexane=1:3→1:2→1:1) to obtain Compound 161 (2.43 g, 99%) as colorless oil.

IRν$_{max}$$^{neat}$cm$^{-l}$: 3050, 2960, 1790, 1745, 1720, 1630, 1480, 1370.

$^1$H-NMR(CDCl$_3$)δ ppm: 1.49(9H,s), 1.51–2.20(9H,m), 2.20–3.10(2H,m), 3.74(3H,s), 3.74(1H,m), 4.63(1H,m).

A mixture of Compound 161 (3.04 g), hydroxylamine hydrochloride (0.623 g), sodium carbonate (0.103 g) and ethanol (66 ml) was refluxed with heating for 2 hours. The reaction mixture was filtered through celite and the filtrate was concentrated. The residue was subjected to a silica gel column chromatography (2.5× 60 cm; ethyl acetate→ethyl acetate:methanol=9:1) to obtain Compound 156 (1.71 g, 54%) as pale yellow oil.

IR$\nu_{max}^{neat}$cm$^{-1}$: 3350, 2960, 1740, 1710, 1690, 1610, 1500, 1440.

$^1$H-NMR(CDCl$_3$)δ ppm: 1.42(9H,s), 1.30-2.21(8H,m), 2.73(2H,m), 2.98(1H,m), 3.73(1H,s), 4.48(1H,m), 5.93(1H,m).

To Compound 156 (1.48 g) was added 0.5N sodium hydroxide solution (25 ml), and the resultant was stirred for 2 hours at room temperature. After the reaction mixture was washed with ethyl acetate, the aqueous layer was acidified to pH 2.7 with 1N hydrochloride acid, saturated with sodium chloric and then extracted with ethyl acetate. The extract was washed with a saturated NaCl solution, dried over sodium sulfate and distilled off to remove the solvent to obtain Compound 157 (1.31 g, 92%) as pale yellow foam.

IR$\nu_{max}^{neat}$cm$^{-1}$: 3400, 2980, 1730, 1710 1690, 1670, 1520, 1450, 1360.

$^1$H-NMR(CDCl$_3$)δ ppm: 1.43(9H,s), 1.60-2.21(8H,m), 2.76(2H,m), 3.07(1H,m), 4.44(1H,m), 6.27(1H,d,J=7.6Hz).

To Compound 157 (1.22 g) was added 4N hydrogen chloride-dioxane (16 ml). The resultant was stirred for an hour at room temperature and distilled off to remove the solvent. The residue was washed three times with ethyl ether by decantation. The residue was dried to obtain Compound 158 (hydrochloride) (1.16 g) as colorless powders.

IR$\nu_{max}^{KBr}$cm$^{-1}$ 3450, 2950, 1740, 1680, 1570, 1510, 1440.

$^1$H-NMR(D$_2$O)δ ppm: 1.50-2.20(8H,m), 2.94(2H,d,J=6.4Hz), 3.17(1H,m), 4.22(1H,t,J=6.4Hz).

SIMS(m/z): 241(M+H)+

EXAMPLE 78

A solution of lithium diisopropylamide in hexane (24.2%, 11 ml) was added to a solution of methyl (S)-N-tert-butoxycarbonylpyroglutamate (3.65 g) in tetrahydrofuran (40 ml) at −78° C. in a stream of nitrogen, followed by stirring for 10 minutes at −78° C. To the reaction mixture was added dropwise a solution of phenylacetaldehyde (1.93 ml) in tetrahydrofuran (3 ml), and the resultant was stirred for 10 minutes at −78° C. To the reaction mixture was added a saturated ammonium chloride solution and stirring was continued until the internal temperature reached room temperature. The reaction mixture was extracted with ethyl acetate. The extract was washed successively with water and a saturated NaCl solution, dried over sodium sulfate and distilled off under reduced pressure to remove the solvent. The residue was subjected to a silica gel column chromatography (2.5 x 60 cm; ethyl acetate:hexane=1:3→1:2→1:1) to obtain methyl (S)-N-tert-butoxycarbonyl-4-(1-hydroxy−2-phenyl−1-ethyl) pyroglutamate (4.09 g, 75%) as colorless oil.

IR$\nu_{max}^{neat}$cm$^{-1}$: 3500, 3030, 2990, 1780, 1750, 1720, 1500, 1480, 1450.

$^1$H-NMR(CDCl$_3$)δ ppm: 1.45(9H,s), 1.90-3.00(5H,m), 3.79(3H,s), 4.63(1H,m), 7.29(5H,s).

Oxalyl chloride (1.17 ml) and a solution of dimethyl sulfoxide (1.71 ml) in dichloromethane (3 ml) were added to dichloromethane (28 ml) at −60° C. in a stream of nitrogen, following by stirring for 2 minutes. To the reaction mixture was added dropwise over 5 minutes a solution of methyl (S)-N-tert-butoxycarbonyl-4-(1-hydroxy−2-phenyl−1-ethyl)pyroglutamate (4.09 g) in dichloromethane (10 ml) and the mixture was stirred for 15 minutes at −60° C. Triethylamine (7.8 ml) was added to the reaction mixture, and the resultant was stirred for 5 minutes and further stirred for an hour at room temperature. After addition of water to the reaction mixture, the organic layer was taken, and the aqueous layer was extracted with dichloromethane. All of the organic layers were combined and washed with a saturated NaCl solution, dried over sodium sulfate and distilled off under reduced pressure to remove the solvent. The residue was subjected to a silica gel column chromatography (2.5 cm×60 cm; ethyl acetate:hexane=1:3→1:2→1:1) to obtain Compound 162 (1.88 g, 46%) as colorless oil.

IR$\nu_{max}^{neat}$cm$^{-1}$: 2980, 1780, 1750, 1720, 1500, 1470, 1450.

$^1$H-NMR(CDCl$_3$)δ ppm: 1.51(9H,s), 2.01-2.90(2H,m), 3.53(1H,d,J=14.4Hz), 3.73(1H,d,J=14.4Hz), 3.80(1H,m), 3.81(3H,s), 4.64(1H,m).

A mixture of Compound 162 (1.45 g), hydroxylamine hydrochloride (0.279 g), sodium carbonate (0.213 g) and ethanol (33 ml) was refluxed with heating for 2 hours. The reaction mixture was filtered through celite and the filtrate was concentrated under reduced pressure. The residue was subjected to a silica gel column chromatography (2.5×40 cm; ethyl acetate→ethyl acetate:methanol=9:1) to obtain Compound 159 (0.304 g, 20%) as pale yellow oil.

IR$\nu_{max}^{neat}$cm$^{-1}$: 3350, 2990, 1740, 1700, 1680, 1510, 1430, 1370.

$^1$H-NMR(CDCl$_3$)δ ppm: 1.35(9H,s), 2.40(2H,m), 3.59(2H,s), 3.73(1H,s), 4.43(1H,m), 6.52(1H,m), 7.23(5H,s).

0.5N Sodium hydroxide solution (4.6 ml) was added to Compound 159 (0.285 g) and the mixture was stirred for 2 hours at room temperature. The reaction mixture was washed with ethyl acetate, and the aqueous layer was taken, acidified to pH 2.7 with 1N hydrochloric acid, saturated with sodium chloride and extracted with ethyl acetate. The extract was washed with a saturated NaCl solution, dried over sodium sulfate and distilled off under reduced pressure to remove the solvent to obtain Compound 160 (0.252 g, 91%) as pale yellow foam.

IR$\nu_{max}^{neat}$cm$^{-1}$: 3350, 3000, 1720-1680, 1600, 1520, 1360.

$^1$H-NMR(CDCl$_3$)δ ppm: 1.42(9H,s), 2.75(2H,m), 3.90(2H,m), 4.40(1H,m), 6.2(1H,d), 7.27(5H,s).

EXAMPLE 79

A solution of lithium diisopropylamide in hexane (30.8%, 5.3 ml) was added to a solution of methyl (S)-N-tert-butoxycarbonylpyroglutamate (2.43 g) in tetrahydrofuran (50 ml) at −78° C. in a stream of nitrogen, followed by stirring for 10 minutes at −78° C. A solution of furfural (0.91 ml) in tetrahydrofuran (3 ml) was added dropwise to the reaction mixture and stirred for 10 minutes at −78° C. To the reaction mixture was added a saturated ammonium chloride solution and stirring was continued until its internal temperature reached room temperature. The reaction mixture was extracted with ethyl acetate. The extract was washed successively with water and a saturated NaCl solution, dried over sodium sulfate and distilled off under reduced pressure. The residue was subjected to a silica gel column chromatography (2.5×40 cm; ethyl acetate:hexane=1:2 - 1:1) to obtain methyl (S)-N-tert-butoxycarbonyl-4-(o-hydroxy—2-furylmethyl)pyroglutamate (3.19 g, 94%) as colorless oil.

$IR\nu_{max}^{neat}cm^{-1}$: 3450, 3020, 1780, 1755, 1720, 1430, 1350.

$^1$H-NMR(CDCl$_3$)$\delta$ ppm: 1.51(9H,s), 1.90-1.60(3H,m), 2.90-3.20(1H,m), 3.77(1.5H,s), 3.79(1.5H,s), 4.59(1H,m), 6.35(2H,m), 7.39(1H,m).

Oxalyl chloride (1.3 ml) and a solution of dimethyl sulfoxide (1.9 ml) in dichloromethane (3 ml) were added dropwise to dichloromethane (30 ml) at $-60°$ C. in a stream of nitrogen and the resultant was stirred for 2 minutes. To the reaction mixture was added dropwise over 5 minutes a solution of methyl (S)-N-tert-butoxycarbonyl- 4-(o-hydroxy—2-furylmethyl)pyroglutamate (4.23 g) in dichloromethane (10 ml), followed by stirring for 15 minutes at $-60°$ C. Triethylamine (8.7 ml) was added to the reaction mixture and stirred for 5 minutes and further stirred for an hour at room temperature. After addition of water, the organic layer was taken, and the aqueous layer was extracted with dichloromethane. All of the organic layers were combined, washed with a saturated NaCl solution, dried over sodium sulfate and distilled off under reduced pressure to remove the solvent. The residue was subjected to a silica gel column chromatography (2.5×60 cm; ethyl acetate:hexane=1:2→1:1) to obtain Compound 163 (2.71 g, 65%) as colorless oil.

$IR\nu_{max}^{neat}cm^{-1}$: 2980, 1800, 1760, 1730, 1670, 1480, 1370.

$^1$H-NMR(CDCl$_3$)$\delta$ ppm: 1.52(9H,s), 2.10-3.00(2H,m), 3.48(1H,dd,J=14Hz,3.4Hz), 3.81(3H,s), 4.68(1H,m), 6.60(1H,dd,J=3.2Hz,1.0Hz), 7.68(1H,d,J=1.0Hz), 7.90(1H,d,J=3.2Hz).

EXAMPLES 80-87

By the method of Example 37, Compound 9, 71, 74, 77, 175, or 154 was condensed with an amino acid derivative or amine and if required, subjected to removal for protecting group to afford Compounds 165–170 and 183–188 shown in Table 13.

TABLE 13

| Example No. | Starting compound | Reagent | Product |
|---|---|---|---|
| 80 | Compound 9 (1 g) L-proline methyl ester. hydrochloride | DEPC (0.66 ml) triethylamine (0.98 ml) | Compound 165 (0.48 g) $^1$H-NMR(d$_6$-DMSO)$\delta$ ppm: 1.34(9H,s), 1.79-2.43(6H,m) 3.68-3.91(2H,m), 3.61(3H,s), 4.01-4.42(2H,m), 6.98(1H,d,J=7Hz), 7.73(1H,s). |
| | Compound 165 (0.46 g) | 0.5N sodium hydroxide solution (6.9 ml) | Compound 166 (0.25 g) $^1$H-NMR(d$_6$-DMSO)$\delta$ ppm: 1.38(9H,s), 1.81-2.48(6H,m), 3.57-3.82(2H,m), 4.21-4.45(2H,m), 6.98(1H,m), 8.20(1H,s) |
| | Compound 166 (0.23 g) | 4N hydrogen chloride-dioxane (12 ml) | Compound 167 (hydrochloride) (0.17 g) $^1$H-NMR(d$_6$-DMSO)$\delta$ ppm: 1.97-2.61(4H,m), 2.92(2H,d,J=6.2Hz), 3.55-3.88(2H,m), 4.41-4.66(2H,m), 8.33(1H,s) |
| 81 | Compound 9 (1.37 g) D-proline methyl ester. hydrochloride (1 g) | DEPC (1.08 ml) triethylamine (1.62 ml) | Compound 168 (0.56 g) $^1$H-NMR(d$_6$-DMSO)$\delta$ ppm: 1.37(9H,s), 1.71-2.42(6H,m), 3.38-3.91(3H,m), 3.58(3H,s), 4.12-4.29(1H,m), 6.86(1H,d,J=7Hz), 7.57(1H,s) |
| | Compound 168 (0.54 g) | 0.5N sodium hydroxide solution (8.1 ml) | Compound 169 (0.33 g) $^1$H-NMR(d$_6$-DMSO)$\delta$ ppm: 1.36(9H,s), 1.81-2.47(6H,m), 3.37-3.79(2H,m), 4.11-4.43(2H,m), 6.81(1H,d,J=7Hz), 8.30(1H,s) |
| | Compound 169 (0.31 g) | 4N hydrogen chloride-dioxane (15 ml) | Compound 170 (hydrochloride) (0.21 g) $^1$H-NMR(d$_6$-DMSO)$\delta$ ppm: 1.88-2.62(4H,m), 2.91(2H,d,J=6.2Hz), 3.52-3.88(2H,m), 4.42-4.65(2H,m), 8.36(1H,s) |
| 82 | Compound 9 (0.272 g) (R)-1-(1-naphthyl) ethylamine (0.165 ml) | DEPC (0.17 ml) triethylamine (0.14 ml) | Compound 183 (0.154 g) $^1$H-NMR(d$_6$-DMSO + D$_2$O) $\delta$ ppm: 1.34(9H,s), 1.47(3H,d,J=6.8Hz), 2.42(1H,dd,J=14.2, 8.3Hz), 2.49(1H,dd, J=14.2, 6.6Hz), 4.13(1H,m), 5.65(1H,q,J=6.8Hz), 7.53(1H,m), 7.57(3H,m) 7.83(1H,d,J=8Hz), 7.95(1H,d,J=8Hz), 8.07(1H,d,J=8Hz), 8.21(1H,s). The above NMR data showed that e.e. (enatiomer excess) of Compound 9 is >99%. |
| 83 | Compound 71 (0.1 g) (R)-1-(1-naphthyl) ethylamine (0.059 g) | DEPC (0.061 ml) triethylamine (0.051 ml) | Compound 184 (0.072 g) $^1$H-NMR(d$_6$-DMSO + D$_2$O) $\delta$ ppm: 1.35(9H,s), 1.49(3H,d,J=6.8Hz), 2.36(1H,dd,J=13.7, 8.5Hz), 2.49(1H,dd, J=13.7, 5.6Hz), 4.13(1H,m), 5.67(1H,q,J=6.8Hz), 7.48(1H,m), 7.55(3H,m), 7.83(1H,m), 7.94(1H,d,J=8Hz), 8.07(1H,d,J=8Hz), 8.13(0.93H,s), 8.21(0.07H,s). The above NMR data showed that e.e. of Compound 71 is 87%. |
| 84 | Compound 74 | DEPC | Compound 185 |

TABLE 13-continued

| Example No. | Starting compound | Reagent | Product |
|---|---|---|---|
| | (0.113 g) (R)-1-(1-naphtyl)-ethylamine (0.063 ml) | (0.065 ml) triethylamine (0.054 ml) | (0.111 g) $^1$H-NMR(d$_6$-DMSO + D$_2$O) δ ppm: 1.35(9H,s), 1.43(3H,d,J=6.8Hz), 1.88(3H,s), 2.34(1H,dd,J=14.4, 7.3Hz), 2.41(1H,dd, J=14.4, 5.6Hz), 4.01(1H,m), 5.62(1H,q,J=6.8Hz), 7.53(3H,m), 7.85(1H,d,J=8Hz), 7.94(1H,d,J=8Hz), 8.08(1H,d,J=8Hz), 8.29(1H,d,J=8Hz). The above NMR data showed that e.e. of Compound 74 is >99%. |
| 85 | Compound 77 (0.16 g) (R)-1-(1-naphtyl) ethylamine (0.09 ml) | DEPC (0.093 ml) triethylamine (0.078 ml) | Compound 186 (0.122 g) $^1$H-NMR(d$_6$-DMSO + D$_2$O) δ ppm: 1.34(9H,s), 1.48(3H,d,J=6.8Hz), 1.93(3H,s), 2.33(1H,dd,J=14.1, 8.3Hz), 2.46(1H,dd, J=14.1, 6.1Hz), 4.10(1H,m), 5.68(1H,q,J=6.8Hz), 7.51(3H,m), 7.82(1H,m), 7.93(1H,d,J=8Hz), 8.08(1H,d,J=8Hz), 8.41(1H,d,J=8Hz) The above NMR data showed that e.e. of Compound 77 is >99%. |
| 86 | Compound 175 (0.107 g) (R)-1-(1-naphtyl) ethylamine (0.063 ml) | DEPC (0.065 ml) triethylamine (0.054 ml) | Compound 187 (0.11 g) $^1$H-NMR(d$_6$-DMSO + D$_2$O) δ ppm: 1.37(9H,s), 1.46(2.17H,d, J=6.8Hz), 1.50(0.83H,d,J=6.8Hz), 1.85(0.83H,s), 2.10(2.17H,s), 4.82(1H,m), 5.71(1H,q,J=6.8Hz), 7.46-7.78(3H,m), 7.82(1H,m), 7.93(1H,d,J=8Hz), 8.09(1H,d,J=8Hz), 8.52(1H,d,J=8Hz). The above NMR data showed that e.e. of Compound 175 is 45%. |
| 87 | Compound 154 (0.14 g) (R)-1-(1-naphtyl) ethylamine (0.082 ml) | DEPC (0.085 ml) triethylamine (0.072 ml) | Compound 188 (0.154 g) $^1$H-NMR(d$_6$-DMSO + D$_2$O) δ ppm: 1.37(9H,s), 1.46(1.18H,d, J=6.8Hz), 1.50 (1.82H,d,J=6.8Hz), 1.85(1.82H,s), 2.10(1.18H,s), 4.82(1H,m), 5.72(1H,q,J=6.8Hz), 7.46-7.78(3H,m), 7.83(1H,m), 7.92(1H,d,J=8Hz), 8.09(1H,d,J=8Hz), 8.53(1H,d,J=8Hz). The above NMR data show that e.e. of Compound 154 is 21%. |

EXAMPLE 88

To a solution of 2.43 g of methyl (S)-N-tert-butoxycarbonylpyroglutamate in 40 ml of tetrahydrofuran was added 5.3 ml of 30.8% lithium isopropylamide-hexane at −78° C. in a stream of nitrogen, followed by stirring for 10 minutes at −78° C. Cyclopropanecarbaldehyde (1.50 g) was added dropwise to the mixture and the mixture was stirred for 10 minutes at −78° C. A saturated ammonium chloride aqueous solution was added to the mixture, which was stirred until the temperature of the mixture reached room temperature. The reaction mixture was extracted with ethyl acetate. The organic layer was washed with water and then a saturated saline solution, dried over anhydrous sodium sulfate and distilled to remove the solvent. The residue was subjected to a silica gel column (2.5×60 cm) chromatography (developed by ethyl acetate-hexane=1:3→1:2→1:1) to obtain 3.11 g (99%) of methyl (S)-N-tert-butoxycarbonyl-4-(α-hydroxycyclopropylmethyl)pyroglutamate as colorless oil.

IR$\nu_{max}^{neat}$cm$^{-1}$: 3500, 3000, 1780, 1750, 1740, 1710, 1470, 1440, 1370.

$^1$H-NMR(CDCl$_3$)δ ppm: 0.2–0.8(5H,m), 1.51(9H,s), 1.95–3.10(4H,m), 3.79(3H,s), 4.64(1H,m)

To 15 ml of dichloromethane were added 0.63 ml of oxalyl chloride and a mixture of 1.1 ml of dimethylsulfoxide and 2 ml of dichloromethane at −60° C. in a stream of nitrogen, followed by stirring for 2 minutes. A solution of 1.88 g of methyl (S)-N-tert-butoxycarbonyl-4-(α-hydroxycyclopropylmethyl)pyroglutamate in 6 ml of dichloromethane was added to the reaction solution during 5 minutes and stirred for 15 minutes at −60° C. Then, 4.18 ml of triethylamine was added to the reaction mixture, and stirred for 5 minutes and then for an hour at room temperature. The reaction mixture was diluted with water to separate the organic layer. The aqueous layer was extracted with dichloromethane. The combined organic layers were washed with a saturated saline solution, dried over sodium sulfate and distilled to remove the solvent. The residue was subjected to a silica gel column (2.5×40 cm) chromatography (ethyl acetate-hexane=1:3→1:2) to obtain 0.927 g (50%) of Compound 164 as colorless oil.

IR$\nu_{max}^{neat}$cm$^{-1}$: 3010, 2990, 1800, 1760, 1730, 1710, 1480, 1370.

$^1$H-NMR(CDCl$_3$)δ ppm: 1.0–1.3(4H,m), 1.47(1H,m), 1.49(9H,s), 2.2–2.8(3H,m), 3.75(3H,s), 4.65(1H,m).

Compound 164 (0.641 g) and 0.161 g of hydroxylamine·hydrochloride were dissolved in a mixture of 4 ml of dioxane and 0.5 ml of water, and the mixture was adjusted to pH 8 with 0.5N-sodium hydroxide and stirred for 24 hours at room temperature. The reaction mixture was adjusted to pH 2.5 with 1N-hydrochloric acid, saturated with sodium chloride and extracted with ethyl acetate. The extract was dried over anhydrous sodium sulfate and distilled under reduced pressure. The residue was subjected to a silica gel column (2.5×60 cm) chromatography (ethyl acetate ethyl acetate-methanol=9:1) to obtain 0.089 g (13%) of Compound 171 as pale yellow oil.

IRν$_{max}^{neat}$cm$^{-1}$: 3400, 3010, 2990, 1740, 1710, 1690, 1610, 1510, 1440.

$^1$H-NMR(CDCl$_3$)δ ppm: 0.8–1.2(4H,m), 1.43(9H,s), 1.85(1H,m), 2.7–2.9(2H,m), 3.75(3H,s), 4.78(1H,m), 5.82(1H,m).

A mixture of 0.89 g of Compound 171 and 1.6 ml of 0.5N-sodium hydroxide was stirred for 2 hours at room temperature and washed with ethyl acetate. The aqueous layer after acidifying to pH 2.7 with 1N-hydrochloric acid was saturated with sodium chloride and extracted with ethyl acetate. The organic layer was washed with a saturated saline solution, dried over sodium sulfate and distilled to obtain 0.066 g (78%) of Compound 172 as pale yellow foam.

IRν$_{max}^{neat}$cm$^{-1}$: 3300, 2990, 1740, 1720, 1690, 1699, 1510, 1390.

$^1$H-NMR(CDCl$_3$)δ ppm: 0.8–1.2(4H,m), 1.44(9H,s), 1.90(1H,m), 2.83(2H,m), 4.45(1H,m), 6.16(1H,d,J=7Hz).

A mixture of 0.066 g of Compound 172 and 2 ml of 4N-hydrogen chloride-dioxane was stirred for an hour at room temperature and the solvent distilled off. The residue was treated with ethyl ether and the supernatant removed three times. The residue was dried to obtain 0.054 g of Compound 173 (hydrochloride) as colorless powders.

IRν$_{max}^{KBr}$cm$^{-1}$: 3450, 2950, 1740, 1680, 1570, 1510, 1440.

$^1$H-NMR(D$_2$O)δ ppm: 0.85–1.10(4H,m), 2.01(1H,m), 3.03(2H,d,J=6.2Hz), 4.27(1H,t,J=6.2Hz).

SIMS(m/z): 213(M+H)$^+$

EXAMPLE 89

To a solution of 3.92 g (15 m mol) of dimethyl (S)-N-tert-butoxycarbonylaspartate in 70 ml of tetrahydrofuran was added 15.8 ml (33 m mol) of 30.8% lithium diisopropylaminde-hexane solution at −78° C. in a stream of nitrogen, followed by stirring for 10 minutes at −78° C. The reaction mixture was stirred for 20 minutes at −40° C. and again cooled to −78° C., to which a solution of 3.3 g (30 m mol) of acetylimmidazole in 30 ml of tetrahydrofuran was added dropwise. After stirring 10 minutes, the reaction mixture was diluted with a saturated ammonium chloride solution and then stirred at room temperature. After addition of excess water, the mixture was extracted with water and then ethyl acetate. The organic layer was washed with a saturated saline solution, dried over anhydrous sodium sulfate and distilled under reduced pressure. The residue was subjected to a silica gel column (2.5×40 cm) chromatography (ethyl acetate-hexane=1:3) to obtain 3.68 g (81%) of dimethyl (S)-N-tert-butoxy-carbonyl-3- acetylaspartate as colorless oil.

IRν$_{max}^{neat}$cm$^{-1}$: 3390, 2980, 1760–1720, 1500, 1420, 1390, 1370

$^1$H-NMR(CDCl$_3$)δ ppm: 1.43(9H,s), 2.31(1.5H,s), 2.33(1.5H,s), 3.75, 3.76(6H, s each), 4.27(1H,m), 4.97(1H,m), 5.61(1H,m).

To a solution of 3.05 g (10 m mol) of the above product in a mixture of 20 ml of 1,4-dioxane and 5 ml of water was added 0.764 g (11 m mol) of hydroxylamine-hydrochloride, followed by stirring 2 hours at room temperature. The reaction mixture was adjusted to pH 4.5 by addition of 0.5N-sodium hydroxide and stirred for an hour. Then, the mixture was acidified to pH 2.0 with 1N hydrochloric acid, saturated with sodium chloride and extracted with ethyl acetate. The extract was washed with a saturated saline solution, dried over anhydrous sodium sulfate and distilled under reduced pressure. The residue was subjected to a silica gel column (2.5×40 cm) chromatography (ethyl acetate-→ethyl acetate: methanol=9:1) to obtain 0.855 g (30%) of Compound 174 as pale yellow foam.

IRν$_{max}^{neat}$cm$^{-1}$: 3400, 2980, 1750, 1710, 1640, 1520, 1430.

$^1$H-NMR(CDCl$_3$)δ ppm: 1.39(9H,s), 1.98(3H,s), 3.65(3H,s), 4.87(1H,m), 6.30(1H,m)

A solution of 0.291 g (1.02 m mol) of compound 174 in 6.1 ml of 0.5N-sodium hydroxide was stirred for an hour at room temperature. The reaction mixture was washed with ethyl acetate. The aqueous layer was acidified to pH 2.7 with 1N-hydrochloric acid, saturated with sodium chloride and extracted with ethyl acetate. The extract was washed with a saturated saline solution, dried over sodium sulfate and distilled under reduced pressure to obtain 0.231 g (83%) of Compound 175 as pale yellow foam.

IRν$_{max}^{neat}$cm$^{-1}$: 3340, 3200, 1750, 1680, 1650, 1580, 1510, 1450.

$^1$H-NMR(d$_6$-DMSO)δ ppm: 1.40(9H,s), 2.12(3H,s), 4.79(1H,d,J=7.2Hz), 7.15(1H,d,J=7.2Hz)

A mixture of 0.91 g (0.33 m mol) of Compound 175 and 4 ml of 4N-hydrogen chloride-dioxane was stirred for an hour and the solvent was distilled off. The residue was treated three times with ethyl acetate by decantation. The precipitate was dried to obtain 0.084 g (93%) of Compound 176 as colorless powders.

IRν$_{max}^{KBr}$cm$^{-1}$: 3430, 2900, 1740, 1710, 1580, 1500.

$^1$H-NMR(D$_2$O):δ ppm: 2.32(3H,s), 4.89(1H,s).

SIMS(m/z): 173(M+H)$^+$

EXAMPLE 90

Compound 177 (hydrochloride) was obtained from dimethyl (RS)-N-tert-butoxycarbonylaspartate by the method of

EXAMPLE 89.

SIMS(m/z): 173(M+H)$^+$

EXAMPLE 91

A solution of 2.61 g (10 m mol) of dimethyl (R)-N-tert-butoxycarbonylaspartate in 10 ml of tetrahydrofuran was added dropwise to a lithium isopropylamide solution [prepared from 4.62 ml (33 m mol) of diisopropylamine and 21 ml (33 m mol) of butyllithium hexane solution, in 30 ml of tetrahydrofuran]at −78° C. in a stream of nitrogen. The mixture was stirred for 10 minutes and a solution of 2.48 g (20 m mol) of propionylimidazole in 15 ml of tetrahydrofuran was added dropwise. The reaction mixture was stirred for 10 minutes at −78° C. and further stirred in a dry ice-acetone bath of −40° C. Stirring was continued until the temperature of the mixture reached −20° C. Then a saturated ammonium chloride aqueous solution was added and the mixture was stirred at room temperature. The mixture was diluted with water and extracted with ethyl acetate. The organic layer was washed with a saturated saline solution, dried over anhydrous sodium sulfate and distilled under reduced pressure. The residue was subjected to a silica gel column (2.5×40 cm) chromatography (ethyl acetate:hexane=1:3→1:2) to obtain 2.93 g (92%) of dimethyl (R)-N-tert-butoxycarbonyl-3-propionylaspartate as colorless oil.

IRν$_{max}^{neat}$cm$^{-1}$: 3370, 2980, 1760–1720, 1500, 1430, 1370.

¹H-NMR(CDCl₃)δ ppm: 1.08(1.5H,t,J=7.2Hz), 1.09(1.5H,t,J=7.2Hz), 1.45(9H,s), 2.65(1H,q,J=7.2Hz), 2.66(1H,q,J=7.2Hz), 3.76(3H,s), 3.77(3H,s), 4.28(1H,d,J=4.6Hz), 4.95(1H,dd,J=9.2, 4.6Hz), 5.6–5.7(1H,m)

To a solution of 2.34 g (7.37 m mol) of the above product in a mixture of 15 ml of 1,4-dioxane and 5 ml of water was added 0.512 g (7.37 m mol) of hydroxylamine·hydrochloride. The mixture was adjusted to pH 5 with 0.5N-sodium hydroxide and stirred for 30 minutes at room temperature. Then, the mixture was acidified to pH 2.0 by addition of 1N-hydrochloric acid, saturated with sodium chloride and extracted with ethyl acetate. The extract was washed with a saturated saline solution, dried over anhydrous sodium sulfate and distilled under reduced pressure. The residue was subjected to a silica gel column (2.5×40 cm) chromatography (ethyl acetate→ethyl acetate: methanol=9:1) to obtain 0.256 g (12%) of Compound 178 as pale yellow foam.

IR$\nu_{max}^{neat}$cm$^{-1}$: 3320, 2980, 1740, 1720, 1710, 1620, 1500, 1430.

¹H-NMR(CDCl₃)δ ppm: 1.12(3H,t,J=7.2Hz), 1.38(9H,s), 2.38(2H,q,J=7.2Hz), 3.78(3H,s), 4.88(1H,m), 6.15(1H,br)

A mixture of 0.25 g (0.83 m mol) of Compound 178 and 5.0 ml of 0.5N-sodium hydroxide was stirred for 2 hours at room temperature. The reaction mixture was washed with ethyl acetate, acidified to pH 2.7 with 1N-hydrochloric acid, saturated with sodium chloride and then extracted with ethyl acetate. The extract was washed with a saturated saline solution, dried over sodium sulfate and distilled under reduced pressure to obtain 0.202 g (85%) of Compound 179 as pale yellow foam.

IR$\nu_{max}^{neat}$cm$^{-1}$: 3300, 3000, 1740, 1720, 1680, 1660, 1590, 1510.

¹H-NMR(d₆-DMSO)δ ppm: 1.14(3H,t,J=7.2Hz), 1.43(9H,s), 2.21(2H,q,J=7.2Hz), 5.12(1H,d,J=7.4Hz), 6.13(1H,d,J=7.4Hz)

A mixture of 0.20 g (0.70 m mol) of Compound 179 and 4 ml of 4N-hydrogen chloride-dioxane was stirred for an hour at room temperature and the solvent was distilled off. The residue was treated three times with ethyl acetate and dried to obtain 0.087 g (42%) of Compound 180 as colorless powders.

IR$\nu_{max}^{neat}$cm$^{-1}$: 3400, 3000, 1740, 1720, 1700, 1580, 1500.

¹H-NMR(D₂O)δ ppm: 1.24(3H,t,J=7.6Hz), 2.74(2H,q,J=7.6Hz), 4.90(1H,s).

SIMS(m/z): 187(M+H)⁺

EXAMPLE 92

A solution of 2.61 g (10 m mol) of dimethyl (R)-N-tert-butoxycarbonylaspartate in 10 ml of tetrahydrofuran was added dropwise to a lithium diisopropylamide solution [prepared from 4.62 ml (33 m mol) of diisopropylamine and 21 ml (33 m mol) of butyllithium-hexane solution, in 30 ml of tetrahydrofuran]at −78° C. in a stream of nitrogen, and the mixture was stirred for 10 minutes at −78° C. Then, a solution of 2.76 g (20 m mol) of isobutyrylimidazole in 15 ml of tetrahydrofuran was added dropwise to the reaction mixture, and the mixture was stirred for 10 minutes at −78° C. and further in a dry ice-acetone bath of −40° C. The mixture was further stirred until the temperature reached −20° C., to which a saturated ammonium chloride solution was added and stirred at room temperature. The reaction mixture was diluted with water and and extracted with ethyl acetate. The organic layer was washed with a saturated saline solution, dried over sodium sulfate and distilled. The residue was subjected to a silica gel column (2.5×40 cm) chromatography (ethyl acetate:hexane=1:3→1:2) to obtain 2.07 g (62%) of dimethyl (R)-N-tert-butoxycarbonyl-3-isobutyrylaspartate as colorless oil.

IR$\nu_{max}^{neat}$cm$^{-1}$: 3390, 2990, 2950, 1760–1720, 1500, 1440, 1370.

¹H-NMR(CDCl₃)δ ppm: 1.11(3H,d,J=7Hz), 1.13(3H,d,J=7Hz), 1.43(4.5H,s), 1.44(4.5H,s,), 2.84(1H,m), 3.72(1.5H,s), 3.75(3H,s), 3.76(1.5H,s), 4.49(0.5H,d,J=4.4Hz), 4.51(0.5H,d,J=3.4Hz), 4.92(1H,m), 5.57(0.5H,d,J=8.8Hz), 5.70(0.5H,d,J=8.8Hz).

To a solution of 1.44 g (4.35 m mol) of the above product in a mixture of 8.5 ml of 1,4-dioxane and 3 ml of water was added 0.302 g (4.35 m mol) of hydroxylamine·hydrochloride. The mixture was brought to pH 8 with 0.5N-sodium hydroxide and stirred for 38 hours at room temperature. Then, it was acidified to pH 2.0 with 1N-hydrochloric acid, saturated with sodium chloride and extracted with ethyl acetate. The extract was washed with a saturated saline solution, dried and distilled under reduced pressure. The residue was subjected to a silica gel column (2.5×40 cm) chromatography (ethyl acetate→ethyl acetate:methanol=9:1→8:1) to obtain 0.115 g (9%) of Compound 181 as pale yellow foam.

IR$\nu_{max}^{neat}$cm$^{-1}$: 3320, 2980, 1740, 1720, 1710, 1620, 1500, 1430.

¹H-NMR(CDCl₃)δ ppm: 1.16(6H,d,J=6.6Hz), 1.38(9H,s), 2.79(1H,m), 4.57(1H,d,J=7.6Hz), 6.80(1H,m).

A mixture of 0.098 g (0.33 m mol) of Compound 181 and 2 ml of 4N-hydrogen chloride-dioxane was stirred for an hour at room temperature and distilled to remove the solvent. The residue was washed three times with ethyl acetate and dried to obtain 0.093 g of Compound 182 as colorless powders.

IR$\nu_{max}^{KBr}$cm$^{-1}$: 3450, 3000, 1700, 1630, 1580, 1500.

¹H-NMR(D₂O)δ ppm: 1.28(3H,d,J=7Hz), 1.30(3H,d,J=7Hz), 3.17(1H,m), 4.90(1H,s).

SIMS(m/z): 201(M+H)⁺

EXAMPLE 93

To a solution of 534 mg of methyl (cis)-2-aminocyclopentanecarboxylate hydrochloride and 1.15 g of Compound 20 in 17.8 ml of dimethylformamide were added 0.53 ml of triethylamine, 418 mg of 1-hydroxybenzotriazole and 592 mg of 1-ethyl-3-(3-dimethylaminopropyl) carbodiimide hydrochloride and stirred for 16 hours. After removing dimethylformamide under reduced pressure, the residue was diluted with 25ml of ethyl acetate and washed with 25 ml of water. The aqueous washing was extrated with 20 ml of ethyl acetate and further 20 ml of ethyl acetate and hexane (2:1). The resulting organic layers were combined, washed with 25 ml of water twice and 20 ml of a saturated saline solution, dried by passing through a column of sodium sulfate and concentrated under reduced pressure to obtain 1.34 g of colorless oil. The resultant oil was purified by a column chromatography (column: silica gel 60 of Merck & Co.; eluent: ethyl acetate→hexane). The fractions showing a single spot were collected and concentrated to dryness to obtain 568 mg of Compound 189 as white powders.

Elemental analysis (C₂₃H₃₅N₃O₉·0.5H₂O) calculated: C, 54.54; H, 7.16; N, 8.29; found: C, 54.46; H, 6.93; N, 8.25

¹H-NMR(300 MHz, CDCl₃) δ ppm: 1.44(9H,s), 1.58(9H,s), 1.60(1H,m), 1.80(1H,m), 2.00(4H,m), 2.75(2H,m), 2.96(1H,q,J=7.2Hz), 3.67(3H,s), 4.30(1H,br.q, J=6Hz), 4.41(1H,quint,J=7.5Hz), 5.60(1H,br.d), 7.00(1H,br.d), 8.14(1H,s)

¹³C-NMR (75 MHz, CDCl₃) δ ppm: 22.07(t), 25.74(t), 27.97(t), 28.02(q), 28.27(q), 31.85(t), 46.29(d), 51.86(q), 52.19(d), 53.83(d), 77.26(s), 80.33(s), 86.86(s), 103.26(s), 142.70(d), 144.24(s), 155.56(s), 170.09(s), 174.60(s)

SIMS(m/z): 498 (M+H)⁺

IR (KBr, cm⁻¹): 3320, 2980, 1760, 1740, 1660, 1510, 1390, 1370, 1320, 1260, 1210, 1150, 1100, 1020, 830, 740

EXAMPLE 94

To a solution of 380 mg of Compound 189 as powders in 7 ml of methanol was added 504 mg of potassium hydroxide (purity of 85%), followed by stirring for 6 hours at room temperature. After removing methanol, the reaction mixture was diluted with 15 ml of water, adjusted to pH 7.2 and washed twice with 15 ml of ethyl acetate. The aqueous layer was adjusted to pH 2.7 with hydrochloric acid, extracted twice with 15 ml of ethyl acetate. The resulting aqueous layer was saturated with sodium chloride and re-extracted with 10 ml of ethyl acetate. The combined extracts were washed with successive 10 ml of a saturated ammonium chloride solution (twice) and 20 ml of a saturated saline solution, dried by passing through a column of anhydrous sodium sulfate and concentrated under reduced pressure to obtain 259 mg of Compound 190 as white powders.

Elemental analysis (C₁₇H₂₅N₃O₇·H₂O) calculated: C, 50.87; H, 6.78; N, 10.47; found: C, 50.81; H, 6.75; N, 10.18

SIMS: M+H 384, M+Na 406

¹H-NMR(300 MHz actone-d₆)δ ppm: 1.40(9H,s), 1.67(2H,m), 1.95(1H,m), 2.60(1H,ddd,J=15, 7.5, 3Hz), 2.71(1H,dd,J=15, 5.5Hz), 2.78 and 2.99(1H,q,J=7Hz), 4.27(1H,m), 4.48(br), 6.27(1H,m), 7.48 and 7.87(1H,m), 8.19 & 8.24(1H,brs)

¹³C-NMR (75 MHz, acetone-d₆)δ ppm: 24.49(CH₂), 27.80/27.84(CH₂), 28.22(CH₃), 28.91(CH₂), 32.98/33.03(CH₂), 47.03/47.22(CH), 51.66/52.68(CH), 55.28/55.40(CH), 78.82/79.30(q), 150.66/152.75(CH), 155.93(q), 172.33(q), 172.96/173.14(q), 175.03/175.13(q)

IR (KBr, cm⁻¹): 3300, 3090, 2980, 1700, 1510, 1390, 1370, 1270, 1250, 1160, 1040, 1020, 860, 760

EXAMPLE 95

Compound 190 (white powders, 225 mg) was dissolved in trifluoroacetic acid (0.5 ml) and allowed to stand for 30 minutes at room temperature. After removing trifluoroacetic acid under reduced pressure, 15 ml of diethyl ether was added to the reaction mixture. The resulting precipitate was collected by filtration, washed with dimethyl ether, dissolved in water (150 ml). The resultant (100 ml) was adjusted to pH 6.7 and passed through a column of QAE-Sephadex (A-25, Cl type, 12 ml), which was eluted by water and three kinds of 0.1M, 0.2M and 0.3M saline solution successively, to collect each 10 ml of fractions. By analyzing each of fractions on HPLC (YMC A-312, 4% acetonitrile/0.01M phosphate buffer, pH 3.0), the fractions showing a single peak of the object compound were collected and concentrated to 15 ml. The concentrate was desalted by Microacilyzer G-1 (made by Asahi Chemical Industry Co., Ltd., in Japan) using Aciplex Cartridge AC-110-10 (made by Asahi Chemical Industry Co., Ltd., in Japan), concentrated and lyophilized to obtain 115 mg of Compound 191 as white powders.

Elemental analysis (C₁₂H₁₇N₃O₅·3.2H₂O) calculated: C; 42.28, H; 6.92, N; 12.33; found: C; 42.20, H; 5.69, N; 11.71

SIMS M+H 284, M+Na 306

IR (KBr, cm⁻¹): 3240, 3080, 2960, 2870, 1670, 1570, 1520, 1400, 1320, 1290, 1200, 1180, 1130, 1080, 920, 830, 800, 740, 720

¹H-NMR(300 MHz, D₂O)δ ppm: 1.51-2.00(4H,m), 2.04(2H,m), 2.54(1H,m), 2.73(1H,m), 2.86(1H,m), 3.98(½H,dd,J=7, 6.5Hz), 4.06(½H,dd,J=8.5, 4Hz), 4.31(2H,m), 6.90, 7.48, 7.49, 7.50(1H, s×4), 7.97 and 8.00(1H,s×2) (equilibrium mixture)

¹³C-NMR(75 MHz, D₂O)δ ppm: 24.80/25.03(CH₂), 25.72/21.96(CH₂), 27.56/27.70(CH₂), 30.53/30.85(CH₂), 32.15/32.40(CH₂), 32.73/32.84(CH₂), 34.55/34.80(CH₂), 34.93(CH₂), 52.72/52.95(CH), 55.55/55.82(CH), 56.00/56.13(CH), 56.59/56.80(CH), 57.98(CH), 58.42(CH), 82.00(q), 151.19(q), 152.59/152.73(q), 158.53(q), 171.47(q), 176.33/176.56(q), 180.32(q), 185.98/186.15(q)

COMPOSITION EXAMPLE 1

A composition for capsule

| | |
|---|---|
| (1) Compound 72 (sodium salt) | 100 mg |
| (2) lactose | 28 mg |
| (3) cornstarch | 58 mg |
| (4) hydroxypropylcellulose | 12 mg |
| (5) magnesium stearate | 2 mg |
| | 200 mg per capsule |

The above ingredients (1), (2), (3) and (4) were mixed and granulated by a conventional method. To the resultant was added the ingredient (5), and the composition was encapsulated into gelatin capsules to obtain capsules.

COMPOSITION EXAMPLE 2

A composition for injection

A solution of Compound 72 (sodium salt, 100 g) in distilled water (1 l) was dissolved in mannitol (100 g) and the solution was sterilely filtered and its 0.5 ml portions were injected into ampoules. They were dried in a lyophilizer and sealed to obtain ampoules for a reconstruction use. Upon the use of said ampoule, its seal is broken and the solution in the ampoule is dissolved in 1 ml of an isotonic sodium chloride solution to obtain an injection for subcutaneous, intravenous or intramuscular administration.

What we claim is:

1. A compound of the formula (I')

or a pharmaceutically acceptable salt thereof wherein $R^1$ is a hydrogen atom, or a $C_{1-6}$ alkyl, $C_{2-6}$ alkenyl, $C_{2-6}$ alkynyl, $C_{3-7}$ cycloalkyl, phenyl, 1-naphthyl, 2-naphthyl, biphenyl, anthryl, indenyl, phenyl-$C_{1-4}$ alkyl; pyridyl, pyrrolyl, furyl, pyranyl or thienyl;

$R^2$ is a hydrogen atom, or an N-protecting group;

—$COR^3$ is an optionally esterified or amidated carboxyl group;

$R^4$ and $R^5$ are the same or different and respectively a hydrogen atom, an acyl group A selected from benzoyl, nitrobenzoyl, $C_{1-4}$ alkylbenzoyl, benzenesulfonyl, $C_{1-4}$ alkylbenzenesulfonyl, $C_{1-4}$ alkanoyl which can be substituted with 1-3 chlorine atoms, $C_{1-4}$ alkylsulfonyl, phenyl-$C_{1-4}$ alkoxycarbonyl and $C_{1-4}$ alkoxycarbonyl, or an amino acid residue of the group consisting of phenylalanyl, α-alanyl, β-alanyl, glycyl, histidyl, isoleucyl, leucyl, lysyl, methionyl, norleucyl, norvalyl, ornityl, prolyl, sarcosyl, seryl, tyrosyl, valyl, triptophyl, α-aspartyl, β-aspartyl, asparaginyl, α-glutamyl, τ-glutamyl, glutaminyl, β-aminoalanyl, 4-thialysyl, 3-(2-aminoethyl) sulfinylalanyl and 4-oxalysyl wherein the carboxyl group may be esterified and the amino group acylated by an acyl group A as defined above; or a $C_{1-6}$ alkyl, $C_{2-6}$ alkenyl, $C_{2-6}$ alkynyl, $C_{3-7}$ cycloalkyl, or a phenyl-$C_{1-4}$ alkyl each of which may be substituted by phenyl, 1-naphthyl, 2-naphthyl, biphenyl, anthryl or indenyl; and n′ is an integer of 0 to 3; or $R^4$ and $R^5$ together with the adjacent nitrogen atom may form a phthalimido, succinimido, maleinimido, benzylidenamino or p-nitrobenzylidenamino group provided that when $R^1$, $R^2$, $R^4$ and $R^5$ are hydrogen atoms, —$COR^3$ is carboxyl group and the steric configuration of the asymmetric carbon atom to which the α-amino group is bonded is S, n′ is 0, 2 or 3.

2. A compound of claim 1 in which $R^3$ with respect to —$COR^3$ is hydroxy, a $C_{1-6}$ alkoxy or a benzyloxy which is unsubstituted or substituted by nitro or methoxy.

3. A compound of claim 1 in which $R^3$ is amino, benzylamino, phenethylamino, α-methylbenzylamino, 3-phenylpropylamino. 1-(1-naphthyl)ethylamino, morpholino, piperidino, 4-phenyl-1-piperazinyl or an amino acid residue selected from alanino, β-alanino, glycino, Nα-histidino, isoleucino, leucino, lysino, methionino, norleucino, norvalino, ornitino, prolino, sarcosino, serino, tyrosino, valino, tryptophano, asparto, asparagino, glutamino, glutamo, β-aminoalanino, α-amino-β-alanino, thialysino, 4-oxyalysino, 3-carboxypropylamino, 4-carboxybutylamino, 4-carboxybenzylamino, 4-carboxypiperidino, 3-carboxypiperidino and 2-carboxypiperidino or 1-carobxycyclopentyl-2-amino.

4. A compound of claim 1 in which $R^3$ is a β-amino acid residue selected from β-alanino, β-aminoalanino, α-amino-β-alanino and 1-carboxycyclopentyl-2-amino.

5. A compound of claim 1 in which both of $R^4$ and $R^5$ are hydrogen atom.

6. A compound of claim 1 in which the acyl radicals of $R^4$ and $R^5$ are an amino acid residue selected from phenylalanyl, alanyl, β-alanyl, glycyl, histidyl, isoleucyl, leucyl, lysyl, methionyl, norleucyl, norvalyl, ornityl, prolyl, sarcosyl, seryl, tyrosyl, valyl, triptophyl, α-aspartyl, β-aspartyl, asparaginyl, α-glutamyl, τ-glutamyl, glutaminyl, β-aminoalanyl, 4-thialysyl, 3-(2-aminoethyl)sulfinylalanyl and 4-oxalysyl wherein in case where the amino acid residues contain a carboxyl group, said carboxyl group may be esterified and an amino group may be acylated by an acyl group selected from the acyl groups A defined in claim 1.

7. A composition for treating senile dementia and memory dysfunction which comprises an effective amount of a compound as defined in claim 1 and a pharmaceutically acceptable carrier or diluent.

8. A compound of claim 1 in which $R^1$, $R^2$, $R^4$ and $R^5$ are hydrogen and $R^3$ is β-alanino.

9. A compound of claim 1 in which $R^1$ is methyl, $R^2$, $R^4$, and $R^5$ are hydrogen and $R^3$ is hydroxy.

10. A compound of claim 1 in which $R^1$, $R^2$, $R^4$ and $R^5$ are hydrogen and $R^3$ is 3-carboxypropylamino.

11. A compound of claim 1 in which $R^1$, $R^2$, $R^4$ and $R^5$ are hydrogen and $R^3$ is 2-carboxypiperidino.

12. A compound of claim 1 in which $R^1$ is cyclopropyl; $R^2$, $R^4$ and $R^5$ are hydrogen and $R^3$ is hydroxy.

13. A compound of claim 1 in which $R^1$, $R^2$, $R^4$ and $R^5$ are hydrogen and $R^3$ is 2-carboxylcyclopentylamino.

14. A compound of claim 1 in which $R^1$ is cyclopentyl, $R^2$, $R^4$ and $R^5$ are hydrogen and $R^3$ is hydroxy.

15. A method of treating senile dementia and memory dysfunction which comprises administration to a mammal in need thereof of an effective amount of a compound having the formula:

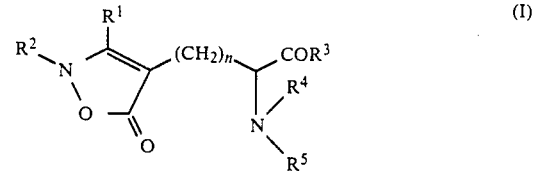

or a pharmaceutically acceptable salt thereof, wherein $R^1$ is a hydrogen atom, a $C_{1-6}$ alkyl, $C_{2-6}$ alkenyl, $C_{2-6}$ alkynyl, $C_{3-7}$ cycloalkyl, phenyl, 1-naphthyl, 2-naphthyl, biphenyl, anthryl, indenyl, phenyl-$C_{1-4}$ alkyl; pyridyl, pyrrolyl, furyl, pyranyl and thienyl; $R^2$ is a hydrogen atom, or an N-protecting group —$COR^3$ is an optionally esterified or amidated carboxyl group; $R^4$ and $R^5$ are the same or different and respectively a hydrogen atom, an acyl group selected from benzoyl, nitrobenzoyl, $C_{1-3}$ alkylbenzoyl, benzenesulfonyl, $C_{1-4}$ alkylbenzenesulfonyl, $C_{1-4}$ alkanoyl which can be substituted with 1-3 chlorine atoms, $C_{1-4}$ alkylsulfonyl, phenyl-$C_{1-4}$ alkoxycarbonyl and $C_{1-4}$ alkoxycarbonyl, or an amino acid residue of the group consisting of phenylalanyl, α-alanyl, β-alanyl, glycyl, histidyl, isoleucyl, leucyl, lysyl, methionyl, norleucyl, norvalyl, ornityl, prolyl, sarcosyl, seryl, tyrosyl, valyl, triptophyl, α-aspartyl, β-aspartyl, asparaginyl, α-glutamyl, τ-glutamyl, glutaminyl, β-aminoalanyl, 4-thialysyl, 3-(2-aminoethyl)sulfinylalanyl and 4-oxalysyl wherein the carboxyl group may be esterified and the amino group acylated by an acyl group A as defined above;

or a $C_{1-6}$ alkyl, $C_{2-6}$ alkenyl, $C_{2-6}$ alkynyl, $C_{3-7}$ cycloalkyl, or a phenyl-$C_{1-4}$ alkyl each of which may be substituted by phenyl, 1-naphthyl, 2-naphthyl, biphenyl, anthryl or indenyl; and n is an integer of 0 to 3; or $R^4$ and $R^5$ together with the adjacent nitrogen atom may form a phthalimido, succinimido, maleinimido, benzylidenamino or p-nitrobenzylidenamino group.

* * * * *